US011643636B2

(12) United States Patent
Shusta et al.

(10) Patent No.: US 11,643,636 B2
(45) Date of Patent: May 9, 2023

(54) METHOD OF CREATING HUMAN PLURIPOTENT STEM CELL DERIVED BRAIN PERICYTE-LIKE CELLS

(71) Applicant: Wisconsin Alumni Research Foundation, Madison, WI (US)

(72) Inventors: Eric V. Shusta, Madison, WI (US); Sean P. Palecek, Verona, WI (US); Matthew Stebbins, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 584 days.

(21) Appl. No.: 16/507,586

(22) Filed: Jul. 10, 2019

(65) Prior Publication Data
US 2020/0017827 A1 Jan. 16, 2020

Related U.S. Application Data

(60) Provisional application No. 62/696,230, filed on Jul. 10, 2018.

(51) Int. Cl.
*C12N 5/079* (2010.01)

(52) U.S. Cl.
CPC ........ *C12N 5/0618* (2013.01); *C12N 2506/02* (2013.01); *C12N 2506/45* (2013.01)

(58) Field of Classification Search
CPC .............. C12N 5/0618; C12N 2506/02; C12N 2506/45; C12N 5/069; C12N 2501/115; C12N 2501/15; C12N 2501/155; C12N 2501/16; C12N 2501/415
See application file for complete search history.

(56) References Cited

U.S. PATENT DOCUMENTS

2014/0127800 A1 5/2014 Shusta

FOREIGN PATENT DOCUMENTS

WO 2017176747 10/2017

OTHER PUBLICATIONS

Chambers et al., Nature Biotechnology, vol. 27, No. 3, 275-281, published online Mar. 1, 2009 (Year: 2009).*
Gibco, Essential 6 Medium, published online 2013. Retrieved from <https://assets.thermofisher.com/TFS-Assets/LSG/manuals/essential_6_medium_man.pdf> Retrieved on Nov. 23, 2021. (Year: 2013).*
Wu et al., Experimental Cell Research, 319:2682699, 2013 (Year: 2013).*
Noisa et al., Stem Cells International, Article ID 647437, vol. 2015; Manent et al., Journal of Neuroscience Methods, 123:167-173, 2003 (Year: 2003).*
Manent et al., Journal of Neuroscience Methods, 123:167-173, 2003 (Year: 2003).*
Greenwood-Goodwin et al., Scientific Reports, 6:24403, Apr. 25, 2016 (Year: 2016).*
Nakagawa, S. et al. A new blood-brain barrier model using primary rat brain endothelial cells, pericytes and astrocytes. Neurochem. Int. 54, 253-263 (2009).
Nakagawa, S. et al. Pericytes from Brain Microvessels Strengthen the Barrier Integrity in Primary Cultures of Rat Brain Endothelial Cells. Cell. Mol. Neurobiol. 27, 687-694 (2007).
Nakagawa, S., et al. Infection of human pericytes by HIV-1 disrupts the integrity of the blood-brain barrier. J. Cell. Mol. Med. 16, 2950-2957 (2012).
Nakagomi, T. et al. Brain Vascular Pericytes Following Ischemia Have Multipotential Stem Cell Activity to Differentiate Into Neural and Vascular Lineage Cells. Stem Cells 33, 1962-1974 (2015).
Niewoehner, J. et al. Increased brain penetration and potency of a therapeutic antibody using a monovalent molecular shuttle. Neuron 81, 49-60 (2014).
Nitta, T. et al. Size-selective loosening of the blood-brain barrier in claudin-5-deficient mice. J Cell Biol 161, 653-660 (2003).
Obermeier, B., et al. Development, maintenance and disruption of the blood-brain barrier. Nat. Med. 19, 1584-96 (2013).
Oceguera-Yanez, F. et al. Engineering the AAVS1 locus for consistent and scalable transgene expression in human iPSCs and their differentiated derivatives. Methods 101, 43-55 (2016).
Olsson, A.-K., et al. VEGF receptor signalling—in control of vascular function. Nat. Rev. Mol. Cell Biol. 7, 359-371 (2006).
Omidi, Y. et al. Evaluation of the immortalised mouse brain capillary endothelial cell line, b.End3, as an in vitro blood-brain barrier model for drug uptake and transport studies. Brain Res. 990, 95-112 (2003).
Orlova, V. V et al. Functionality of endothelial cells and pericytes from human pluripotent stem cells demonstrated in cultured vascular plexus and zebrafish xenografts. Arterioscler. Thromb. Vasc. Biol. 34, 177-186 (2014).
Orlova, Valeria V., et al. "Generation, expansion and functional analysis of endothelial cells and pericytes derived from human pluripotent stem cells." Nature protocols 9.6 (2014): 1514.
Pangalos, M. N. et al. "Drug development for CNS disorders: strategies for balancing risk and reducing attrition." Nature Reviews Drug Discovery 6.7 (2007): 521.
Pardridge, W. M. Molecular Trojan horses for blood-brain barrier drug delivery. Curr. Opin. Pharmacol. 6, 494-500 (2006).
Pardridge, W. M. The blood-brain barrier: bottleneck in brain drug development. NeuroRx 2, 3-14 (2005).
Pardridge, W. M., et al. Brain-type glucose transporter (GLUT-1) is selectively localized to the blood-brain barrier. Studies with quantitative western blotting and in situ hybridization. J Biol Chem 265, 18035-18040 (1990).
Parihar, M. S. et al. Alzheimer's disease pathogenesis and therapeutic interventions. J. Clin. Neurosci. 11, 456-467 (2004).
Park et al., Hypoxia-enhanced Blood-Brain Barrier Chip recapitulates human barrier function, drug penetration, and antibody shuttling properties. bioRxiv (2018), doi:10.1101/482463.

(Continued)

*Primary Examiner* — Stacey N MacFarlane
(74) *Attorney, Agent, or Firm* — Quarles & Brady LLP

(57) ABSTRACT

A population of brain pericyte-like cells, wherein the cells express pericyte markers but do not express ACTA2 and wherein the cells are generated from hPSCs, is disclosed herein.

4 Claims, 13 Drawing Sheets
(12 of 13 Drawing Sheet(s) Filed in Color)
Specification includes a Sequence Listing.

(56) References Cited

OTHER PUBLICATIONS

Peppiatt, C. M., et al. Bidirectional control of CNS capillary diameter by pericytes. Nature 443, 700-704 (2006).
Pi, X. et al. Sequential roles for myosin-X in BMP6-dependent filopodial extension, migration, and activation of BMP receptors. J. Cell Biol. 179, 1569-1582 (2007).
Poduslo, J. F. et al. Polyamine modification increases the permeability of proteins at the blood-nerve and blood-brain barriers. J. Neurochem. 66, 1599-1609 (1996).
Preston, J. E., et al. "Transcytosis of macromolecules at the blood-brain barrier." Advances in pharmacology. vol. 71. Academic Press, 2014. 147-163.
Regan, J. N. et al. Building a vessel wall with notch signaling. Circulation research 104, 419-421 (2009).
Reyahi et al., Foxf2 Is Required for Brain Pericyte Differentiation and Development and Maintenance of the Blood-Brain Barrier. Dev. Cell. 34, 19-32 (2015).
Ribecco-Lutkiewicz et al., A novel human induced pluripotent stem cell blood-brain barrier model: Applicability to study antibody-triggered receptor-mediated transcytosis. Sci. Rep. 8, 1-17 (2018).
Roux, F. S. et al. Lipid synthesis by rat brain microvessel endothelial cells in tissue culture. J. Neuropathol. Exp. Neurol. 48, 437-447 (1989).
Roy, B., et al. Synergistic activation of retinoic acid (RA)-responsive genes and induction of embryonal carcinoma cell differentiation by an RA receptor alpha (RAR alpha)-, RAR beta-, or RAR gamma-selective ligand in combination with a retinoid X receptor-specific ligan. Mol. Cell. Biol. 15, 6481-6487 (1995).
Sagar, D. et al. Mechanisms of dendritic cell trafficking across the blood-brain barrier. J. Neuroimmune Pharmacol. 7, 74-94 (2012).
Sagare, A. P. et al. Pericyte loss influences Alzheimer-like neurodegeneration in mice. Nat. Commun. 4, (2013).
Sagare, A. P., et al. Neurovascular Dysfunction and Faulty Amyloid β-Peptide Clearance in Alzheimer Disease. Cold Spring Harb. Perspect. Med. 2, a011452 (2012).
Saharinen, P. et al. Angiopoietins assemble distinct Tie2 signalling complexes in endothelial cell-cell and cell-matrix contacts. Nat. Cell Biol. 10, 527-537 (2008).
Sakuma, R. et al. Brain pericytes serve as microglia-generating multipotent vascular stem cells following ischemic stroke. J. Neuroinflammation 13, 57 (2016).
Savettieri, G. et al. Neurons and ECM regulate occludin localization in brain endothelial cells. Neuroreport 11, 1081-1084 (2000).
Schiera, G. et al. Permeability properties of a three-cell type in vitro model of blood-brain barrier. J. Cell. Mol. Med. 9, 373-9 (2005).
Schiera, G. et al. Synergistic effects of neurons and astrocytes on the differentiation of brain capillary endothelial cells in culture. J. Cell. Mol. Med. 7, 165-70 (2003).
Schlageter, K. E., et al. Microvessel organization and structure in experimental brain tumors: microvessel populations with distinctive structural and functional properties. Microvasc. Res. 58, 312-328 (1999).
Sharma, G. et al. Cell penetrating peptide tethered bi-ligand liposomes for delivery to brain in vivo: biodistribution and transfection. J. Control. Release 167, 1-10 (2013).
Shlosberg, D., et al., A. Blood-brain barrier breakdown as a therapeutic target in traumatic brain injury. Nat Rev Neurol 6, 393-403 (2010).
Sieczkiewicz, G. J. et al. TGF-beta 1 signaling controls retinal pericyte contractile protein expression. Microvasc. Res. 66, 190-196 (2003).
Skripka-Serry, J. The great neuro-pipeline brain drain (and why Big Pharma hasn't given up on CNS disorders) Fall 13. Drug Discovery World (2013). Available at: http://www.ddw-online.com/therapeutics/p216813-the-great-neuro-pipeline-brain-drain-(and-why-big-pharma-hasn-t-given-up-on-cns-disorders)-fall-13.html. (Accessed: Jun. 11, 2016).
Sofroniew, M. V. et al. Astrocytes: Biology and pathology. Acta Neuropathol. 119, 7-35 (2010).
Stamatovic, S. M., et al, Potential role of MCP-1 in endothelial cell tight junction 'opening': signaling via Rho and Rho kinase. J. Cell Sci. 116, 4615-4628 (2003).
Staquicini, F. I. et al. Systemic combinatorial peptide selection yields a non-canonical iron-mimicry mechanism for targeting tumors in a mouse model of human glioblastoma. J. Clin. Invest. 121, 161-173 (2011).
Stebbins et al., Activation of RARa, RAR?, or RXRa Increases Barrier Tightness in Human Induced Pluripotent Stem Cell-Derived Brain Endothelial Cells. Biotechnol. J. 1700093, 1700093 (2017).
Stebbins, M. J. et al. Differentiation and characterization of human pluripotent stem cell-derived brain microvascular endothelial cells. Methods 101, 93-102 (2016).
Stebbins, M.J. Investigating blood-brain barrier (BBB) signaling cues through a human pluripotent stem cell (hPSC)-derived tissue model of the BBB. Diss. University of Wisconsin-Madison, 2017.
Stenman, J. M. et al. Canonical Wnt signaling regulates organ-specific assembly and differentiation of CNS vasculature. Science 322, 1247-50 (2008).
Stins, et al, Bacterial invasion and transcytosis in transfected human brain microvascular endothelial cells, 19-28 (2001).
Stratman, A. N., et al. Pericyte recruitment during vasculogenic tube assembly stimulates endothelial basement membrane matrix formation. Blood 114, 5091-5101 (2009).
Strong, L. H. The Early Embryonic Pattern of Internal Vascularization of the Mammalian Cerebral Cortex. J. Comp. Neurol. 123, 121-138 (1964).
Zlokovic, B. V. Neurovascular pathways to neurodegeneration in Alzheimer's disease and other disorders. Nat. Rev. Neurosci. 12, 723-38 (2011).
Zlokovic, B. V. The Blood-Brain Barrier in Health and Chronic Neurodegenerative Disorders. Neuron 57, 178-201 (2008).
Stewart, K. S., et al. Delta-like ligand 4-Notch signaling regulates bone marrow-derived pericyte/vascular smooth muscle cell formation. Blood 117, 719-726 (2011).
Stewart, P. A. et al. Developing nervous tissue induces formation of blood-brain barrier characteristics in invading endothelial cells: a study using quail-chick transplantation chimeras. Dev. Biol. 84, 183-92 (1981).
Korn, J., et al. Neuroectodermal origin of brain pericytes and vascular smooth muscle cells. J. Comp. Neurol. 442, 78-88 (2002).
Krencik, R., et al. "Specification of transplantable astroglial subtypes from human pluripotent stem cells." Nature biotechnology 29.6 (2011): 528.
Kuhnert, F. et al. Essential Regulation of CNS Angiogenesis by the Orphan G Protein-Coupled Receptor GPR124. Science (80-.). 330, 985-989 (2010).
Kumar et al., Specification and Diversification of Pericytes and Smooth Muscle Cells from Mesenchymoangioblasts. Cell Rep. 19, 1902-1916 (2017).
Kurokawa, R. et al. Regulation of retinoid signalling by receptor polarity and allosteric control of ligand binding. Nature 371, 528-531 (1994).
Kusuma, S. et al. Self-organized vascular networks from human pluripotent stem cells in a synthetic matrix. Proc. Natl. Acad. Sci. U. S. A. 110, 12601-6 (2013).
Lajoie, J. M. et al. Targeting receptor-mediated transport for delivery of biologies across the blood-brain barrier. Annu. Rev. Pharmacol. Toxicol. 55, 613-31 (2015).
Lebrin, F., et al. TGF-beta receptor function in the endothelium. Cardiovasc. Res. 65, 599-608 (2005).
Lechardeur, D., et al. Induction of blood-brain barrier differentiation in a rat brain-derived endothelial cell line. Exp Cell Res 220, 161-170 (1995).
Lee, G. et al. Isolation and directed differentiation of neural crest stem cells derived from human embryonic stem cells. Nat. Biotechnol. 25, 1468-1475 (2007).
Lee, Gabsang, et al. "Derivation of neural crest cells from human pluripotent stem cells." Nature protocols 5.4 (2010): 688.
Lee, S.-W. et al. SSeCKS regulates angiogenesis and tight junction formation in blood-brain barrier. Nat Med 9, 900-906 (2003).

(56) References Cited

OTHER PUBLICATIONS

Leid, M. et al. Purification, cloning, and RXR identity of the HeLa cell factor with which RAR or TR heterodimerizes to bind target sequences efficiently. Cell 68, 377-395 (1992).

Li, F. F. et al. Endothelial Smad4 Maintains Cerebrovascular Integrity by Activating N-Cadherin through Cooperation with Notch. Dev Cell 20, 291-302 (2011).

Liebner, S. et al. Wnt/beta-catenin signaling controls development of the blood-brain barrier. J. Cell Biol. 183, 409-417 (2008).

Lim et al., Huntington's Disease iPSC-Derived Brain Microvascular Endothelial Cells Reveal WNT-Mediated Angiogenic and Blood-Brain Barrier Deficits. Cell Rep. 19, 1365-1377 (2017).

Lippmann ES et al. (2012). Derivation of blood-brain barrier endothelial cells from human pluripotent stem cells. Nat Biotechnol 30:783-91.

Lippmann, E. S. et al. "Deterministic HOX patterning in human pluripotent stem cell-derived neuroectoderm." Stem cell reports 4.4 (2015): 632-644.

Lippmann, E. S., et al Defined human pluripotent stem cell culture enables highly efficient neuroepithelium derivation without small molecule inhibitors. Stem Cells 32, 1032-42 (2014).

Lippmann, E. S., et al. A retinoic acid-enhanced, multicellular human blood-brain barrier model derived from stem cell sources. Sci. Rep. 4, 4160 (2014).

Lippmann, E. S., et al. Blood-brain barrier modeling with co-cultured neural progenitor cell-derived astrocytes and neurons. J. Neurochem. 119, 507-520 (2011).

Lippoldt, A. et al. Structural alterations of tight junctions are associated with loss of polarity in stroke-prone spontaneously hypertensive rat blood-brain barrier endothelial cells. Brain Res. 885, 251-261 (2000).

Liu, H., et al. NOTCH3 Expression Is Induced in Mural Cells Through an Autoregulatory Loop That Requires Endothelial-Expressed JAGGED1. Circ. Res. 104, 466-U97 (2009).

Loscher, W. et al. Role of drug efflux transporters in the brain for drug disposition and treatment of brain diseases. Prog. Neurobiol. 76, 22-76 (2005).

Lutolf, M. P., et al. Designing materials to direct stem-cell fate. Nature 462, 433-41 (2009).

Ma, S., et al. Radial glial neural progenitors regulate nascent brain vascular network stabilization via inhibition of Wnt signaling. PLoS Biol. 11, e1001469 (2013).

Macdonald, B. K., et al. "The incidence and lifetime prevalence of neurological disorders in a prospective community-based study in the UK." Brain 123.4 (2000): 665-676.

Maddaluno, L. et al. EndMT contributes to the onset and progression of cerebral cavernous malformations. Nature 498, 492-496 (2013).

Maden, M. Retinoic acid in the development, regeneration and maintenance of the nervous system. Nat. Rev. Neurosci. 8, 755-65 (2007).

Maden, M. Retinoid signalling in the development of the central nervous system. Nat. Rev. Neurosci. 3, 843-53 (2002).

Man, Shumei, et al. "Human brain microvascular endothelial cells and umbilical vein endothelial cells differentially facilitate leukocyte recruitment and utilize chemokines for T cell migration." Clinical and Developmental Immunology 2008 (2008).

Mantle, et al, Minimum Transendothelial Electrical Resistance Thresholds for the Study of Small and Large Molecule Drug Transport in a Human in Vitro Blood-Brain Barrier Model. Mol. Pharm. 13, 4191-4198 (2016).

Mark, M., et al. Function of retinoic acid receptors during embryonic development. Nucl Recept Signal 7, e002 (2009).

Mcgonigle, P. Animal models of CNS disorders. Biochem. Pharmacol. 87, 140-149 (2014).

Megard, I. et al. A co-culture-based model of human blood-brain barrier: Application to active transport of indinavir and in vivo-in vitro correlation. Brain Res. 927, 153-167 (2002).

Mendelsohn, C. et al. Function of the retinoic acid receptors (RARs) during development (II). Multiple abnormalities at various stages of organogenesis in RAR double mutants. Development 120, 2749-71 (1994).

Menendez et al., Wnt signaling and a Smad pathway blockade direct the differentiation of human pluripotent stem cells to multipotent neural crest cells. Proc. Natl. Acad. Sci. 109, 9220-9220 (2012).

Menendez L, et al. Directed differentiation of human pluripotent cells to neural crest stem cells. Nat Protoc. Jan. 2013;8(1):203-12. doi: 10.1038/nprot.2012.156. Epub Jan. 3, 2013.

Menendez, Laura, et al. "Wnt signaling and a Smad pathway blockade direct the differentiation of human pluripotent stem cells to multipotent neural crest cells." Proceedings of the National Academy of Sciences 108.48 (2011): 19240-19245.

Mi et al., PANTHER version 11: Expanded annotation data from Gene Ontology and Reactome pathways, and data analysis tool enhancements. Nucleic Acids Res. 45, D183-D189 (2017).

Milesi et al., Redistribution of PDGFRβ cells and NG2DsRed pericytes at the cerebrovasculature after status epilepticus. Neurobiol. Dis. 71, 151-158 (2014).

Miller, D. S., et al. Modulation of P-Glycoprotein at the Blood-Brain Barrier: Opportunities to Improve Central Nervous System Pharmacotherapy. Pharmacol. Rev. 60, 196-209 (2008).

Mizee, M. R. et al. Astrocyte-derived retinoic acid: a novel regulator of blood-brain barrier function in multiple sclerosis. Acta Neuropathol. 128, 691-703 (2014).

Mizee, M. R. et al. Retinoic Acid Induces Blood-Brain Barrier Development. J Neurosci 33, 1660-1671 (2013).

Morita, K., et al. Endothelial claudin: claudin-5/TMVCF constitutes tight junction strands in endothelial cells. J. Cell Biol. 147, 185-194 (1999).

Mueller, T. D. et al. Promiscuity and specificity in BMP receptor activation. FEBS Lett. 586, 1846-1859 (2012).

Muramatsu et al., Prostacyclin prevents pericyte loss and demyelination induced by lysophosphatidylcholine in the central nervous system. J. Biol. Chem. 290, 11515-11525 (2015).

Nag, S. et al. in Pathology and Genetics: Cerebrovascular Diseases (ed. Kalimo, H.) pp. 22-29 (ISN Neuropath Press, 2005).

Nagaoka, M., et al. Culture of human pluripotent stem cells using completely defined conditions on a recombinant E-cadherin substratum. BMC Dev. Biol. 10, 60 (2010).

Nagaoka, M., et al. Design of a vitronectin-based recombinant protein as a defined substrate for differentiation of human pluripotent stem cells into hepatocyte-like cells. PLoS One 10, 1-17 (2015).

Syvanen, S. et al. Species differences in blood-brain barrier transport of three positron emission tomography radioligands with emphasis on P-glycoprotein transport. Drug Metab. Dispos. 37, 635-643 (2009).

Takahashi, K. et al. Induction of Pluripotent Stem Cells from Adult Human Fibroblasts by Defined Factors. Cell 131, 861-872 (2007).

Takahashi, K. et al. Induction of Pluripotent Stem Cells from Mouse Embryonic and Adult Fibroblast Cultures by Defined Factors. Cell 126, 663-676 (2006).

Tam, S. J. et al. Death receptors DR6 and TROY regulate brain vascular development. Dev. Cell 22, 403-17 (2012).

Thomson, J. A. et al. Embryonic stem cell lines derived from human blastocysts. Science 282, 1145-1147 (1998).

Tiscornia, G., et al. Diseases in a dish: modeling human genetic disorders using induced pluripotent cells. Nature Medicine 1570-1576 (2011). doi:10.1038/nm.2504.

Tran, N. D., et al. Transforming growth factor-beta mediates astrocyte-specific regulation of brain endothelial anticoagulant factors. Stroke 30, 1671-1678 (1999).

Triguero, D., et al. Blood-brain barrier transport of cationized immunoglobulin G: enhanced delivery compared to native protein. Proc. Natl. Acad. Sci. U. S. A. 86, 4761-4765 (1989).

Urich, E., et al. Transcriptional profiling of human brain endothelial cells reveals key properties crucial for predictive in vitro blood-brain barrier models. PLoS One 7, e38149 (2012).

Van Doorn, R. et al. Sphingosine 1-phosphate receptor 5 mediates the immune quiescence of the human brain endothelial barrier. J. Neuroinflammation 9, 133 (2012).

(56) References Cited

OTHER PUBLICATIONS

Van Geest, R. J., et al. Differential TGF-beta signaling in retinal vascular cells: a role in diabetic retinopathy? Invest. Ophthalmol. Vis. Sci. 51, 1857-1865 (2010).
Vanlandewijck et al., A molecular atlas of cell types and zonation in the brain vasculature. Nature. 554, 475-480 (2018).
Vatine GD et al. (2017). Modeling psychomotor retardation using iPSCs from MCT8-deficient patients indicates a prominent role for the blood-brain barrier. Cell Stem Cell 20:831-43.
Verkman, A. S. Aquaporin water channels and endothelial cell function. J. Anat. 200, 617-627 (2002).
Von Tell, D., et al. Pericytes and vascular stability. Exp. Cell Res. 312, 623-629 (2006).
Wakui, S. et al. Localization of Ang-1, -2, Tie-2, and VEGF expression at endothelial-pericyte interdigitation in rat angiogenesis. Lab. Investig. 86, 1172-1184 (2006).
Walshe, T. E. et al. Microvascular retinal endothelial and pericyte cell apoptosis in vitro: role of hedgehog and Notch signaling. Invest. Ophthalmol. Vis. Sci. 52, 4472-4483 (2011).
Wang et al., Derivation of Smooth Muscle Cells with Neural Crest Origin from Human Induced Pluripotent Stem Cells. Cells Tissues Organs. 195, 5-14 (2012).
Wang, et al, Microfluidic blood-brain barrier model provides in vivo-like barrier properties for drug permeability screening. Biotechnol. Bioeng. 114, 184-194 (2017).
Wang, R. N. et al. Bone Morphogenetic Protein (BMP) signaling in development and human diseases. Genes Dis. 1, 87-105 (2014).
Warren, M. S. et al. Comparative gene expression profiles of ABC transporters in brain microvessel endothelial cells and brain in five species including human. Pharmacol. Res. 59, 404-413 (2009).
Wei et al., Erythrocytes Are Oxygen-Sensing Regulators of the Cerebral Microcirculation. Neuron. 91, 851-862 (2016).
Weidenfeller, C. et al. "Differentiating embryonic neural progenitor cells induce blood-brain barrier properties." Journal of neurochemistry 101.2 (2007): 555-565.
Weidenfeller, C., et al. Murine brain capillary endothelial cells exhibit improved barrier properties under the influence of hydrocortisone. Brain Res. 1053, 162-174 (2005).
Weksler, B. B. et al. Blood-brain barrier-specific properties of a human adult brain endothelial cell line. FASEB J. 19, 1872-1874 (2005).
Wilson, H. K., et al. Cryopreservation of Brain Endothelial Cells Derived from Human Induced Pluripotent Stem Cells Is Enhanced by Rho-Associated Coiled Coil-Containing Kinase Inhibition. Tissue Eng. Part C Methods 22, 1085-1094 (2016).
Wilson, H.K. et al. Exploring the effects of cell seeding density on the differentiation of human pluripotent stem cells to brain microvascular endothelial cells. Fluids Barriers CNS 12, 13 (2015).
Winkler, E. a et al. GLUT1 reductions exacerbate Alzheimer's disease vasculo-neuronal dysfunction and degeneration. Nat. Neurosci. 18, 521-530 (2015).
Winkler, E. a, et al. Central nervous system pericytes in health and disease. Nat. Neurosci. 14, 1398-1405 (2011).
Wohlfart, S., et al. Transport of drugs across the blood-brain barrier by nanoparticles. J. Control. Release 161, 264-73 (2012).
Wolburg, H. et al. Localization of claudin-3 in tight junctions of the blood-brain barrier is selectively lost during experimental autoimmune encephalomyelitis and human glioblastoma multiforme. Acta Neuropathol 105, 586-592 (2003).
Wolburg, H. et al. Tight junctions of the blood-brain barrier: Development, composition and regulation. Vascular Pharmacology 38, 323-337 (2002).
Yamamizu, Kohei, et al. "In Vitro Modeling of Blood-Brain Barrier with Human iPSC-Derived Endothelial Cells, Pericytes, Neurons, and Astrocytes via Notch Signaling." Stem Cell Reports 8.3 (2017): 634.
Yao, Y., et al. Astrocytic laminin regulates pericyte differentiation and maintains blood brain barrier integrity. 1. Yao, Y., Chen, Z.-L., Norris, E. H. & Strickland, S. Astrocytic laminin regulates pericyte differentiation and maintains blood brain barrier integrity. Na. Nat. Commun. 5, 3413 (2014).
Yemisci, M. et al. Pericyte contraction induced by oxidative-nitrative stress impairs capillary reflow despite successful opening of an occluded cerebral artery. Nat. Med. 15, 1031-1037 (2009).
Yu, A. S. L. et al. Knockdown of occludin expression leads to diverse phenotypic alterations in epithelial cells. Am. J. Physiol. Cell Physiol. 288, C1231-41 (2005).
Yu, J. et al. Human induced pluripotent stem cells free of vector and transgene sequences. Science 324, 797-801 (2009).
Yu, J. et al. Induced pluripotent stem cell lines derived from human somatic cells. Science 318, 1917-1920 (2007).
Yu, V. C. et al. RXR beta: a coregulator that enhances binding of retinoic acid, thyroid hormone, and vitamin D receptors to their cognate response elements. Cell 67, 1251-1266 (1991).
Yu, Y. J. et al. Boosting brain uptake of a therapeutic antibody by reducing its affinity for a transcytosis target. Sci. Transl. Med. 3, 84ra44 (2011).
Yu, Y. J. et al. Developing therapeutic antibodies for neurodegenerative disease. Neurotherapeutics 10, 459-72 (2013).
Yu, Y. J. et al. Therapeutic bispecific antibodies cross the blood-brain barrier in nonhuman primates. Sci Transl Med 6, 261ra154 (2014).
Zhang et al., Analysis of SM22?-De cient Mice Reveals Unanticipated Insights into Smooth Muscle Cell Differentiation and Function. Society. 21, 1336-1344 (2001).
Zhang, L., et al. The neurovascular unit and combination treatment strategies for stroke. TRENDS Pharmacol. Sci. 33, 415-422 (2012).
Zhao, Z. et al. Central role for PICALM in amyloid-β blood-brain barrier transcytosis and clearance. Nat. Neurosci. 18, 978-87 (2015).
Zhao, Z., et al. "Establishment and dysfunction of the blood-brain barrier." Cell 163.5 (2015): 1064-1078.
Zheng, X. et al. Proteomic analysis for the assessment of different lots of fetal bovine serum as a raw material for cell culture. Part IV. Application of proteomics to the manufacture of biological drugs. Biotechnol. Prog. 22, 1294-1300 (2006).
Zhou, Y. et al. Gpr124 controls CNS angiogenesis and blood-brain barrier integrity by promoting ligand-specific canonical Wnt signaling. Dev. Cell 31, 248-256 (2014).
Ziegler, N. et al. beta-Catenin Is Required for Endothelial Cyp1b1 Regulation Influencing Metabolic Barrier Function. J. Neurosci. 36, 8921-8935 (2016).
Zlokovic, B. V, et al. Low-density lipoprotein receptor-related protein-1: a serial clearance homeostatic mechanism controlling Alzheimer's amyloid beta-peptide elimination from the brain. J. Neurochem. 15, 1077-1089 (2010).
Abbott, N. J., et al. Astrocyte-endothelial interactions at the blood-brain barrier. Nat. Rev. Neurosci. 7, 41-53 (2006).
Abbott, N. Joan, et al. "Structure and function of the blood-brain barrier." Neurobiology of disease 37.1 (2010): 13-25.
Abbott, N. Joan. "Blood-brain barrier structure and function and the challenges for CNS drug delivery." Journal of inherited metabolic disease 36.3 (2013): 437-449.
Afonso, P. V et al. Alteration of Blood-Brain Barrier Integrity by Retroviral Infection. PLoS Pathog 4, 1-11 (2008).
Akkaya, B. G. et al. The multidrug resistance pump ABCB1 is a substrate for the ubiquitin ligase NEDD4-1. Molecular membrane biology 32, 39-45 (2015).
Al Tanoury, Z., et al. Vitamin A and retinoid signaling: genomic and nongenomic effects. J. Lipid Res. 54, 1761-75 (2013).
Alarcon-Martinez et al., Capillary pericytes express a-smooth muscle actin, which requires prevention of filamentous-actin depolymerization for detection. Elife. 7, 1-17 (2018).
Alvarez, J. I. et al. The Hedgehog pathway promotes blood-brain barrier integrity and CNS immune quiescence. Science 334, 1727-31 (2011).
Anderson, K. D. et al. Angiogenic sprouting into neural tissue requires Gpr124, an orphan G protein-coupled receptor. Proc Natl Acad Sci U S A 108, 2807-2812 (2011).

(56) References Cited

OTHER PUBLICATIONS

Appelt-Menzel et al., Establishment of a Human Blood-Brain Barrier Co-culture Model Mimicking the Neurovascular Unit Using Induced Pluri- and Multipotent Stem Cells. Stem Cell Reports. 8, 894-906 (2017).
Armulik A et al. (2010). Pericytes regulate the blood-brain barrier. Nature 468:557-61.
Armulik, A. et al. "Endothelial/pericyte interactions." Circulation research 97.6 (2005): 512-523.
Armulik, A. et al. "Pericytes: developmental, physiological, and pathological perspectives, problems, and promises." Developmental cell 21.2 (2011): 193-215.
Azevedo, F. A. C. et al. Equal numbers of neuronal and nonneuronal cells make the human brain an isometrically scaled-up primate brain. J. Comp. Neurol. 513, 532-541 (2009).
Banks, W. A. From blood-brain barrier to blood-brain interface: new opportunities for CNS drug delivery. Nat. Rev. Drug Discov. 15, 275-292 (2016).
Bar, T. Patterns of vascularization in the developing cerebral cortex. Ciba Found. Symp. 100, 20-36 (1983).
Bell, R. D. et al. Pericytes control key neurovascular functions and neuronal phenotype in the adult brain and during brain aging. Neuron 68, 409-427 (2010).
Ben-Zvi, A. et al. Mfsd2a is critical for the formation and function of the blood-brain barrier. Nature 509, 507-11 (2014).
Bien-Ly, N. et al. Transferrin receptor (TfR) trafficking determines brain uptake of TfR antibody affinity variants. J. Exp. Med. 211, 233-44 (2014).
Boado, et al, Differential expression of alpha-actin mRNA and immunoreactive protein in brain microvascular pericytes and smooth muscle cells. J. Neurosci. Res. 39, 430-5 (1994).
Boado, R. J., et al. Engineering and expression of a chimeric transferrin receptor monoclonal antibody for blood-brain barrier delivery in the mouse. Biotechnol. Bioeng. 102, 1251-58 (2009).
Boado, R. J., et al. Selective expression of the large neutral amino acid transporter at the blood-brain barrier. Proc. Natl. Acad. Sci. U. S. A. 96, 12079-84 (1999).
Bodnar, et al, Pericyte Regulation of Vascular Remodeling Through the CXC Receptor 3. Arterioscler. Thromb. Vasc. Biol. 33, 2818-2829 (2013).
Bondjers, C. et al. Microarray analysis of blood microvessels from PDGF-B and PDGF-Rbeta mutant mice identifies novel markers for brain pericytes. FASEB J. 20, 1703-1705 (2006).
Bonney, S. et al. Diverse Functions of Retinoic Acid in Brain Vascular Development. J. Neurosci. 36, 7786-7801 (2016).
Bouillet, P. et al. Developmental expression pattern of Stra6, a retinoic acid-responsive gene encoding a new type of membrane protein. Mech. Dev. 63, 173-86 (1997).
Braam, S. R. et al. Recombinant vitronectin is a functionally defined substrate that supports human embryonic stem cell self-renewal via alphavbeta5 integrin. Stem Cells 26, 2257-2265 (2008).
Butt, A. M., et al. Electrical-Resistance Across the Blood-Brain-Barrier in Anesthetized Rats—a Developmental-Study. J. Physiol. 429, 47-62 (1990).
Calabria, et al, Puromycin-purified rat brain microvascular endothelial cell cultures exhibit improved barrier properties in response to glucocorticoid induction, 922-933 (2006).
Canfield SG et al. (2017). An isogenic blood-brain barrier model comprising brain endothelial cells, astrocytes, and neurons derived from human induced pluripotent stem cells. J Neurochem 140:874-88.
Cecchelli, R. et al. A Stable and Reproducible Human Blood-Brain Barrier Model Derived from Hematopoietic Stem Cells. PLoS One 9, e99733 (2014).
Cecchelli, R. et al. Modelling of the blood-brain barrier in drug discovery and development. Nat. Rev. Drug Discov. 6, 650-661 (2007).
Chang, W. G., et al. "A short discourse on vascular tissue engineering." NPJ Regenerative medicine 2.1 (2017): 7.

Chen, G. et al. Chemically defined conditions for human iPS cell derivation and culture. Nat. Methods 8, 424-429 (2011).
Cheung C, et al. Directed differentiation of embryonic origin-specific vascular smooth muscle subtypes from human pluripotent stem cells. Nat Protoc. Apr. 2014;9(4):929-38. doi: 10.1038/nprot.2014.059. Epub Mar. 27, 2014.
Cheung C, et al. Modeling cerebrovascular pathophysiology in amyloid-β metabolism using neural-crest-derived smooth muscle cells. Cell Rep. Oct. 9, 2014;9(1):391-401. doi: 10.1016/j.celrep.2014.08.065. Epub Oct. 2, 2014.
Cheung, C., et al. Generation of human vascular smooth muscle subtypes provides insight into embryological origin-dependent disease susceptibility. Nat. Biotechnol. 30, 165-73 (2012).
Ciumas, M. et al. Bone morphogenetic proteins protect pulmonary microvascular endothelial cells from apoptosis by upregulating a—b-crystallin. Arterioscler. Thromb. Vasc. Biol. 33, 2577-2584 (2013).
Clark et al., Analysis of cancer-targeting alkylphosphocholine analogue permeability characteristics using a human induced pluripotent stem cell blood-brain barrier model. Mol. Pharm. 13, 3341-3349 (2016).
Coisne, C. et al. Tight Junctions in Brain Barriers During Central Nervous System Inflammation. Antioxid. Redox Signal. 15, 1285-1303 (2011).
Couch, J. A. et al. Addressing safety liabilities of TfR bispecific antibodies that cross the blood-brain barrier. Sci. Transl. Med. 5, 183ra57, 1-12 (2013).
Crone, C. et al. Electrical-Resistance of a Capillary Endothelium. J. Gen. Physiol. 77, 349-371 (1981).
Cullen, M. et al. GPR124, an orphan G protein-coupled receptor, is required for CNS-specific vascularization and establishment of the blood-brain barrier. Proc Natl Acad Sci U S A 108, 5759-5764 (2011).
Cundy, K. C. et al. XP13512 [(+/−)-1-([(alpha-isobutanoyloxyethoxy)carbonyl] aminomethyl)-1-cyclohexane acetic acid], a novel gabapentin prodrug: I. Design, synthesis, enzymatic conversion to gabapentin, and transport by intestinal solute transporters. J. Pharmacol. Exp. Ther. 311, 315-323 (2004).
Dalkara, T. et al. Cerebral microvascular pericytes and neurogliovascular signaling in health and disease. Brain Res. 1623, 3-17 (2015).
Dando, S. J. et al. Pathogens penetrating the central nervous system: Infection pathways and the cellular and molecular mechanisms of invasion. Clin. Microbiol. Rev. 27, 691-726 (2014).
Daneman R et al. (2010). Pericytes are required for blood-brain barrier integrity during embryogenesis. Nature 468:562-6.
Daneman, R. et al. The Mouse Blood-Brain Barrier Transcriptome: A New Resource for Understanding the Development and Function of Brain Endothelial Cells. PLoS One 5, e13741-e13741 (2010).
Daneman, R. et al. Wnt/beta-catenin signaling is required for CNS, but not non-CNS, angiogenesis. Proc. Natl. Acad. Sci. U. S. A. 106, 641-646 (2009).
De Bock, M. et al. A new angle on blood-CNS interfaces: A role for connexins? FEBS Lett. 588, 1259-1270 (2014).
De Boer, A. G., et al. The role of drug transporters at the blood-brain barrier. Annu. Rev. Pharmacol. Toxicol. 43, 629-656 (2003).
Deane, R., et al. Clearance of amyloid-beta peptide across the blood-brain barrier: implication for therapies in Alzheimer's disease. CNS Neurol. Disord. Drug Targets 8, 16-30 (2009).
Dejana, E., et al. The control of vascular integrity by endothelial cell junctions: molecular basis and pathological implications. Dev Cell 16, 209-221 (2009).
Deli, M. A., et al. N,N-diethyl-2-[4-(phenylmethyl)phenoxy]ethanamine increases the permeability of primary mouse cerebral endothelial cell monolayers. Inflamm. Res. 52 Suppl 1, S39-40 (2003).
Deli, M. A., et al. Permeability studies on in vitro blood-brain barrier models: physiology, pathology, and pharmacology. Cell. Mol. Neurobiol. 25, 59-127 (2005).
Diaz-Flores, L. et al. Pericytes. Morphofunction, interactions and pathology in a quiescent and activated mesenchymal cell niche. Histol. Histopathol. 24, 909-969 (2009).
Dohgu, S. et al. Brain pericytes contribute to the induction and up-regulation of blood-brain barrier functions through transforming growth factor-beta production. Brain Res. 1038, 208-215 (2005).

(56) References Cited

OTHER PUBLICATIONS

Dore-Duffy, P. et al. "Morphology and properties of pericytes." The blood-brain and other neural barriers. Humana Press, 2011. 49-68.
Dyer, L. A., et al. The role of BMPs in endothelial cell function and dysfunction. Trends Endocrinol. Metab. 25, 472-480 (2014).
El Hafny, B. et al. Modulation of P-glycoprotein activity by glial factors and retinoic acid in an immortalized rat brain microvessel endothelial cell line. Neurosci Lett 236, 107-111 (1997).
Engelhardt, B. et al. Novel insights into the development and maintenance of the blood-brain barrier. Cell Tissue Res. 355, 687-699 (2014).
Erickson, M. A. et al. Blood-brain barrier dysfunction as a cause and consequence of Alzheimer's disease. J. Cereb. Blood Flow Metab. 33, 1500-13 (2013).
Etchevers, H. C., et al. The cephalic neural crest provides pericytes and smooth muscle cells to all blood vessels of the face and forebrain. Development 128, 1059-68 (2001).
Feeney, J. F. J. et al. The development of the vascular pattern within the walls of the central nervous system of the chick embryo. J. Morphol. 78, 231-303 (1946).
Fossati, S. et al. Differential activation of mitochondrial apoptotic pathways by vasculotropic amyloid-beta variants in cells composing the cerebral vessel walls. FASEB J. 24, 229-41 (2010).
Friden, P. M. et al. Anti-transferrin receptor antibody and antibody-drug conjugates cross the blood-brain barrier. Proceedings of the National Academy of Sciences of the United States of America 88, 4771-4775 (1991).
Garbelli et al., PDGFRβ+cells in human and experimental neurovascular dysplasia and seizures. Neuroscience. 306, 18-27 (2015).
GE, W.-P. P., et al. Local generation of glia is a major astrocyte source in postnatal cortex. Nature 484, 376-80 (2012).
Gingrich, M. B. et al. Serine proteases and brain damage—is there a link? Trends Neurosci 23, 399-407 (2000).
Gomes, P. et al. L-DOPA transport properties in an immortalised cell line of rat capillary cerebral endothelial cells, RBE 4. Brain Res. 829, 143-150 (1999).
Gonul et al., Early pericyte response to brain hypoxia in cats: An ultrastructural study. Microvasc. Res. 64, 116-119 (2002).
Goumans, M.-J. et al. Balancing the activation state of the endothelium via two distinct TGF-beta type I receptors. EMBO J. 21, 1743-1753 (2002).
Graesser, D. et al. Altered vascular permeability and early onset of experimental autoimmune encephalomyelitis in PECAM-1-deficient mice. J Clin Invest 109, 383-392 (2002).
Griffin, R. Bajpai, Neural crest-derived human cranial pericytes model primary forebrain pericytes and predict disease-specific cranial vasculature defects. SSRN (2018).
Guimaraes-Camboa et al., Pericytes of Multiple Organs Do Not Behave as Mesenchymal Stem Cells In Vivo. Cell Stem Cell. 20, 345-359.e5 (2017).
Haj-Yasein, N. N. et al. Glial-conditional deletion of aquaporin-4 (Aqp4) reduces blood-brain water uptake and confers barrier function on perivascular astrocyte endfeet. Proc. Natl. Acad. Sci. U. S. A. 108, 17815-20 (2011).
Hall, C. N. et al. Capillary pericytes regulate cerebral blood flow in health and disease. Nature 508, 55-60 (2014).
Halliday MR et al. (2015). Accelerated pericyte degeneration and blood-brain barrier breakdown in apolipoprotein E4 carriers with Alzheimer's disease. J Cereb Blood Flow Metab 36:1-9.
Hamilton, N. B., et al. Pericyte-mediated regulation of capillary diameter: a component of neurovascular coupling in health and disease. Front. Neuroenergetics 2, 1-14 (2010).
Hatherell, K., et al. Development of a three-dimensional, all-human in vitro model of the blood-brain barrier using mono-, co-, and tri-cultivation Transwell models. J. Neurosci. Methods 199, 223-229 (2011).
He et al., Analysis of the brain mural cell transcriptome. Sci. Rep. 6, 35108 (2016).
Helbing, T. et al. BMP activity controlled by BMPER regulates the proinflammatory phenotype of endothelium. Blood 118, 5040-5049 (2011).
Hellstrom, M. et al. Dll4 signalling through Notch1 regulates formation of tip cells during angiogenesis. Nature 445, 776-780 (2007).
Helms, H. C. et al. In vitro models of the blood-brain barrier: An overview of commonly used brain endothelial cell culture models and guidelines for their use. J. Cereb. Blood Flow Metab. 36, 862-890 (2016).
Herve, F. et al. "CNS delivery via adsorptive transcytosis." The AAPS journal 10.3 (2008): 455-472.
Hill et al., Regional Blood Flow in the Normal and Ischemic Brain Is Controlled by Arteriolar Smooth Muscle Cell Contractility and Not by Capillary Pericytes. Neuron. 87, 95-110 (2015).
Hill, J., et al. Emerging Roles of Pericytes in the Regulation of the Neurovascular Unit in Health and Disease. J. Neuroimmune Pharmacol. 591-605 (2014). doi:10.1007/s11481-014-9557-x.
Hobson, B. et al. Endothelial proliferation in tumours and normal tissues: continuous labelling studies. Br. J. Cancer 49, 405-413 (1984).
Hogan, K. A., et al. The neural tube patterns vessels developmentally using the VEGF signaling pathway. Development 131, 1503-1513 (2004).
Huang, X. et al. Induction of the neural crest and the opportunities of life on the edge. Dev. Biol. 275, 1-11 (2004).
Igarashi, Y. et al. Glial cell line-derived neurotrophic factor induces barrier function of endothelial cells forming the blood-brain barrier. Biochem. Biophys. Res. Commun. 261, 108-112 (1999).
Ikeda, E., et al. Developing brain cells produce factors capable of inducing the HT7 antigen, a blood-brain barrier-specific molecule, in chick endothelial cells. Neurosci. Lett. 209, 149-152 (1996).
Iorio, A. L. et al. Blood-Brain Barrier and Breast Cancer Resistance Protein: A Limit to the Therapy of CNS Tumors and Neurodegenerative Diseases. Anticancer. Agents Med. Chem. 16, 810-815 (2016).
Jones, A. R. et al. Blood-brain barrier transport of therapeutics via receptor-mediation. Pharm. Res. 24, 1759-1771 (2007).
Kamouchi, M., et al. The Possible Roles of Brain Pericytes in Brain Ischemia and Stroke. Cell. Mol. Neurobiol. 32, 159-165 (2012).
Kearney, J. B., et al. The VEGF receptor flt-1 (VEGFR-1) is a positive modulator of vascular sprout formation and branching morphogenesis. Blood 103, 4527-4535 (2004).
Kesselheim, A. S. et al. "Two decades of new drug development for central nervous system disorders." Nat. Rev. Drug Discov. 14, 815-816 (2015).
Kim BJ et al. (2017). Modeling Group B *Streptococcus* and blood-brain barrier interaction using induced pluripotent stem cell-derived brain endothelial cells. mSphere 2:e00398-17.
Kim, C. W. et al. Anti-inflammatory and antiatherogenic role of bmp receptor ii in endothelial cells. Arterioscler. Thromb. Vasc. Biol. 33, 1350-1359 (2013).
Knowland, D. et al. "Stepwise recruitment of transcellular and paracellular pathways underlies blood-brain barrier breakdown in stroke." Neuron 82.3 (2014): 603-617.

\* cited by examiner

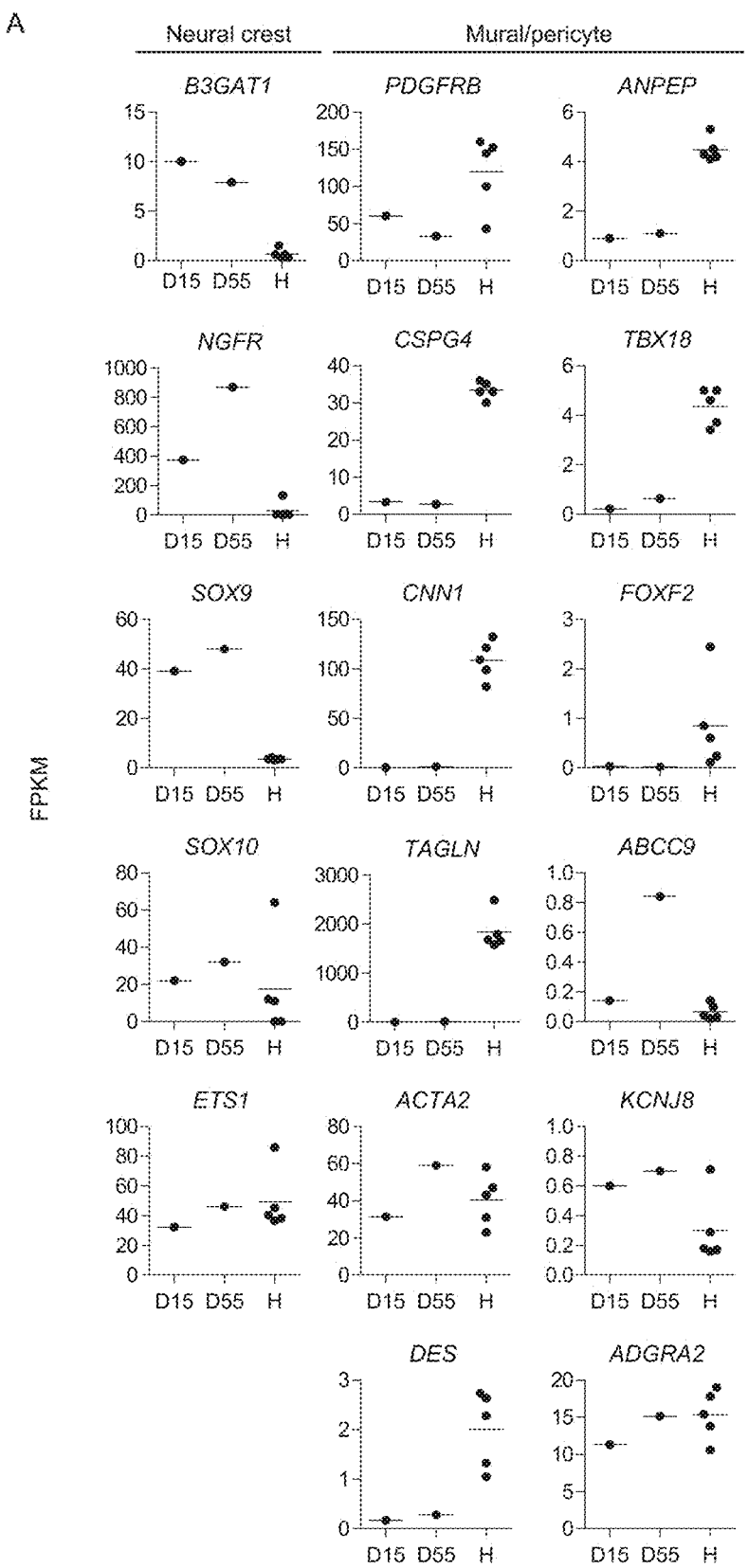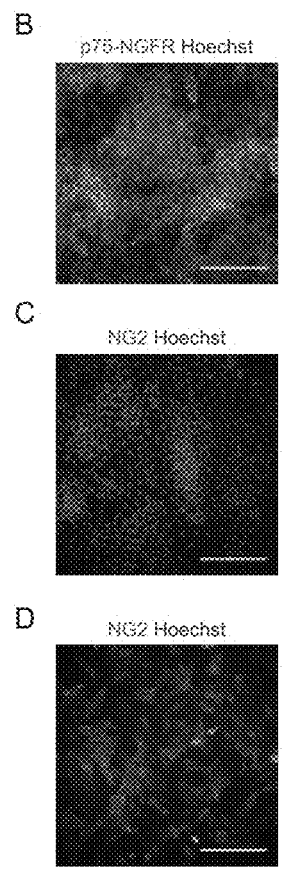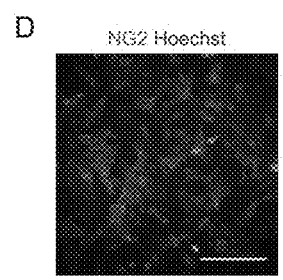
FIGS. 12A-12D.

SEQUENCE LISTING

```
<160> NUMBER OF SEQ ID NOS: 36

<210> SEQ ID NO 1
<211> LENGTH: 21
<212> TYPE: DNA
<213> ORGANISM: Artificial Sequence
<220> FEATURE:
<223> OTHER INFORMATION: synthetic

<400> SEQUENCE: 1
tcaacctggt ccctcatgtc t                                            21

<210> SEQ ID NO 2
<211> LENGTH: 23
<212> TYPE: DNA
<213> ORGANISM: Artificial Sequence
<220> FEATURE:
<223> OTHER INFORMATION: synthetic

<400> SEQUENCE: 2
caggagagcg aatgtaagaa tcc                                          23
```

```
<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
tgttccagcc atccttcatc                                               20

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
gcaatgccag ggtacatagt                                               20

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
gaagagaact ggaggaagat tcag                                          24

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
ccaggttgaa ggcgtcatta                                               20

<210> SEQ ID NO 7
<211> LENGTH: 20
<212> TYPE: DNA
<213> ORGANISM: Artificial Sequence
<220> FEATURE:
<223> OTHER INFORMATION: synthetic

<400> SEQUENCE: 7
tcgcctggac tggactgggg                                               20

<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
tggccttggc ctccctcctc                                               20

<210> SEQ ID NO 9
<211> LENGTH: 18
<212> TYPE: DNA
<213> ORGANISM: Artificial Sequence
<220> FEATURE:
<223> OTHER INFORMATION: synthetic
```

```
<400> SEQUENCE: 9
gtccaccctc ctggcttt                                                 18

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
aaacttgttg gtgcccatct                                               20

<210> SEQ ID NO 11
<211> LENGTH: 23
<212> TYPE: DNA
<213> ORGANISM: Artificial Sequence
<220> FEATURE:
<223> OTHER INFORMATION: synthetic

<400> SEQUENCE: 11
accagagcgt ctgtcaggat att                                           23

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
gtgacttgaa tccgtcccag tttc                                          24

<210> SEQ ID NO 13
<211> LENGTH: 23
<212> TYPE: DNA
<213> ORGANISM: Artificial Sequence
<220> FEATURE:
<223> OTHER INFORMATION: synthetic

<400> SEQUENCE: 13
gaaggtgaag gtcggagtca acg                                           23

<210> SEQ ID NO 14
<211> LENGTH: 22
<212> TYPE: DNA
<213> ORGANISM: Artificial Sequence
<220> FEATURE:
<223> OTHER INFORMATION: synthetic

<400> SEQUENCE: 14
tcctggaaga tggtgatggg at                                            22

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
gtgattgccg tccgaaatgg                                               20

<210> SEQ ID NO 16
```

```
<211> LENGTH: 22
<212> TYPE: DNA
<213> ORGANISM: Artificial Sequence
<220> FEATURE:
<223> OTHER INFORMATION: synthetic

<400> SEQUENCE: 16
agttggtgaa taggaaccac ct                                             22

<210> SEQ ID NO 17
<211> LENGTH: 23
<212> TYPE: DNA
<213> ORGANISM: Artificial Sequence
<220> FEATURE:
<223> OTHER INFORMATION: synthetic

<400> SEQUENCE: 17
cgaagaatag caatggtgtg acg                                            23

<210> SEQ ID NO 18
<211> LENGTH: 21
<212> TYPE: DNA
<213> ORGANISM: Artificial Sequence
<220> FEATURE:
<223> OTHER INFORMATION: synthetic

<400> SEQUENCE: 18
ttccaaagca gcctccaagt c                                              21

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
gtgggacaga gtctgggtgt                                                20

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
aaggagggga ggtgatagga                                                20

<210> SEQ ID NO 21
<211> LENGTH: 22
<212> TYPE: DNA
<213> ORGANISM: Artificial Sequence
<220> FEATURE:
<223> OTHER INFORMATION: synthetic

<400> SEQUENCE: 21
gctcaccatc atctccctta tc                                             22

<210> SEQ ID NO 22
<211> LENGTH: 22
<212> TYPE: DNA
<213> ORGANISM: Artificial Sequence
<220> FEATURE:
<223> OTHER INFORMATION: synthetic

<400> SEQUENCE: 22
```

```
ctcacagact caatcacctt cc                                          22

<210> SEQ ID NO 23
<211> LENGTH: 19
<212> TYPE: DNA
<213> ORGANISM: Artificial Sequence
<220> FEATURE:
<223> OTHER INFORMATION: synthetic

<400> SEQUENCE: 23
cagtgcccga aacccacac                                              19

<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24
ggagacccag cagcctcaaa                                             20

<210> SEQ ID NO 25
<211> LENGTH: 24
<212> TYPE: DNA
<213> ORGANISM: Artificial Sequence
<220> FEATURE:
<223> OTHER INFORMATION: synthetic

<400> SEQUENCE: 25
atacgacact gtcccggccc taaa                                        24

<210> SEQ ID NO 26
<211> LENGTH: 24
<212> TYPE: DNA
<213> ORGANISM: Artificial Sequence
<220> FEATURE:
<223> OTHER INFORMATION: synthetic

<400> SEQUENCE: 26
ttctcctctg tccagcctgt tctc                                        24

<210> SEQ ID NO 27
<211> LENGTH: 20
<212> TYPE: DNA
<213> ORGANISM: Artificial Sequence
<220> FEATURE:
<223> OTHER INFORMATION: synthetic

<400> SEQUENCE: 27
agcgaacgca acatcaagac                                             20

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
ctgtaggcga tctgttgggg                                             20

<210> SEQ ID NO 29
<211> LENGTH: 21
<212> TYPE: DNA
```

<213> ORGANISM: Artificial Sequence
<220> FEATURE:
<223> OTHER INFORMATION: synthetic

<400> SEQUENCE: 29
tctttgaagg caaagacatg g                                                    21

<210> SEQ ID NO 30
<211> LENGTH: 20
<212> TYPE: DNA
<213> ORGANISM: Artificial Sequence
<220> FEATURE:
<223> OTHER INFORMATION: synthetic

<400> SEQUENCE: 30
ttatgctcct gcgctttctt                                                      20

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
cccaggactc cctcctatgt                                                      20

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
taggaaccct gatgggtctg                                                      20

<210> SEQ ID NO 33
<211> LENGTH: 24
<212> TYPE: DNA
<213> ORGANISM: Artificial Sequence
<220> FEATURE:
<223> OTHER INFORMATION: synthetic

<400> SEQUENCE: 33
tccctgtcca agtccaacag caat                                                 24

<210> SEQ ID NO 34
<211> LENGTH: 24
<212> TYPE: DNA
<213> ORGANISM: Artificial Sequence
<220> FEATURE:
<223> OTHER INFORMATION: synthetic

<400> SEQUENCE: 34
aaattcggtt tcgcacacgt accc                                                 24

<210> SEQ ID NO 35
<211> LENGTH: 19
<212> TYPE: DNA
<213> ORGANISM: Artificial Sequence
<220> FEATURE:
<223> OTHER INFORMATION: synthetic

<400> SEQUENCE: 35
tggcccggag cagagtaat                                                       19

```
<210> SEQ ID NO 36
<211> LENGTH: 19
<212> TYPE: DNA
<213> ORGANISM: Artificial Sequence
<220> FEATURE:
<223> OTHER INFORMATION: synthetic

<400> SEQUENCE: 36
ccctgtgtgc gtcctttg                                                   19
```

METHOD OF CREATING HUMAN PLURIPOTENT STEM CELL DERIVED BRAIN PERICYTE-LIKE CELLS

CROSS-REFERENCE TO RELATED APPLICATIONS

This application claims priority to U.S. Provisional Application No. 62/696,230 filed on Jul. 10, 2018, the contents of which are incorporated by reference in its entirety.

STATEMENT REGARDING FEDERALLY SPONSORED RESEARCH

This invention was made with government support under HDTRA1-15-1-0012 awarded by the DOD/DTRA and NS083688 awarded by the National Institutes of Health. The government has certain rights in the invention.

BACKGROUND

The blood-brain barrier (BBB) is comprised of specialized brain microvascular endothelial cells (BMECs) that line the vasculature of the central nervous system (CNS). BMECs allow for the selective passage of essential nutrients and metabolites into the brain and help prevent the entry of damaging substances. While the BBB plays an important role in CNS homeostasis, it also creates a bottleneck for the delivery of therapeutics[1-3]. In addition, BBB dysfunction has been observed in many CNS pathologies including Alzheimer's disease, multiple sclerosis, and stroke, and increasing evidence demonstrates treating BBB contribution to CNS disorders may improve disease outcomes[4-12]. Importantly, BMECs gain their unique properties as a result of coordinated signaling cues from other brain cells surrounding CNS microvessels, including CNS pericytes, astrocytes, and neurons that together with BMECs form the neurovascular unit (NVU)[13-18]. Recently, brain pericyte contributions to BBB development and function have begun to be elucidated, and potential pericyte roles in CNS disease have been suggested. CNS pericytes associate with BMECs early in embryonic development as nascent blood vessels invade the developing neural tube. The emergence of pericytes corresponds to BBB formation through reduction of transcytosis, decreased immune cell adhesion molecule expression, and reduced ultrastructural tight junction abnormalities[13]. In the adult, pericytes regulate vascular stability and diameter[5,19-21], contribute to the BMEC basement membrane[20,22-24,] regulate BMEC molecular phenotype[14,25] and reduce non-specific molecular transcytosis[14].

As a result of the emerging importance of brain pericytes in brain health and disease, they have been increasingly incorporated into in vitro models of the BBB. For example, co-culture with pericytes can improve BMEC phenotype in co-culture systems, stabilize endothelial cell cord formation in vitro[26], and induce BMEC properties in primary and hematopoietic stem cell-derived endothelial cells[27-29]. We also reported that primary brain pericytes could be combined with human pluripotent stem cell derived BMECs (hPSC-derived BMECs) and enhance their functionality[30]. Such hPSC-derived BBB models offer the capability for screening of CNS-penetrant therapeutics[31] and can be used to investigate BBB contributions to human disease using patient-derived induced pluripotent stem cells (iPSCs)[32,33]. While we and others have recently demonstrated the combination of iPSC-derived BMECs with iPSC-derived astrocytes and neurons to form high fidelity multicellular BBB models[34-36], the inclusion of pericytes, to date, has largely been limited to primary human sources[30,35]. Unfortunately, primary sources do not scale with high fidelity[37,38], and unlike iPSC sources, do not reflect the genetic contributions that can be important to modeling human disease. Thus, for patient-specific modeling of the healthy and diseased BBB, it is paramount to generate brain pericyte-like cells from human iPSCs.

Vascular mural cells include both smooth muscle cells, which line arterioles and venules, and pericytes, which are associated with smaller microvessels and capillaries. Until very recently, it has been difficult to distinguish smooth muscle cells from pericytes based on marker expression[39]. Moreover, hPSC-derived mural cells from different embryonic origins display functionally distinct phenotypes and respond differentially to disease pathways[40,41]. While most mural cells originate from mesoderm, CNS forebrain mural cells arise from neural crest stem cells (NCSCs)[42,43], a multipotent stem cell population capable of forming peripheral neurons and mesenchymal derivatives including adipocytes, osteocytes, and chondrocytes[44,45], among other cell types. Previous studies have described processes to differentiate hPSCs to NCSCs and demonstrated their potential to form vascular smooth muscle cells[41,45,46.] However, it is unknown whether NCSCs can generate pericyte-like cells that enhance BBB phenotypes in BMECs. Here, we describe a facile protocol for generating multipotent NCSCs from hPSCs by canonical WNT signaling activation with simultaneous inhibition of BMP and activin/nodal signaling as previously described[45,47]. These hPSC-derived NCSCs can be further differentiated to mural cells that express pericyte markers by 9 days of culture in serum-containing medium. These pericyte-like cells associated with vascular cord networks and induced key pericyte-driven phenotypes in BMECs including the enhancement of barrier properties and reduction of transcytosis. Finally, an isogenic model of the NVU comprised of iPSC-derived pericytes, BMECs, astrocytes, and neurons, exhibited elevated barrier properties compared to a model lacking pericytes, suggesting future applications of iPSC-derived pericytes in CNS drug screening, BBB development studies and disease modeling applications.

Needed in the art is an improved method of creating iPSC-derived pericytes.

SUMMARAY OF THE INVENTION

In one aspect, the present invention provides a population of brain pericyte-like cells, wherein the cells express pericyte markers but do not express ACTA2 and wherein the cells are generated from hPSCs. Further aspects provide methods of producing such cells. In one aspect, the suitable pericyte markers include CNN1, NG2, and PDGFRB. Further aspects comprise blood brain barrier models comprising the brain pericyte-like cells.

In another aspect, the disclosure provides a method of creating a population of brain pericyte-like cells, wherein the cells express pericyte markers but do not express ACTA2 and wherein the cells are generated from human pluripotent stem cells (hPSC), comprising the steps of a. culturing hPSC in E6-CSFD medium for about 15 days to produced p75-NGFR+HNK+NCSC cells, b. sorting p75-NGFR⁺ cells and re-plating the p75-NGFR⁺ cells to produce an enriched population of p75-NGFR⁺ NCSCs, and c. culturing the cells of step (b) in E6 media with an addition of serum for about 11 days, wherein a brain pericyte-like population of cells that express pericyte markers but do not express ACTA2 is produced.

In another aspect, the disclosure provides a method of creating a population of p75-NGFR+HNK+NSCs from human pluripotent stem cells, the method comprising: a. culturing hPSC in E6-CSFD medium for about 15 days to produced p75-NGFR+HNK+NCSC cells, and b. sorting p75-NGFR+ cells and re-plating the p75-NGFR+ cells of step (a) to produce a population of p75-NGFR+ NCSCs.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 6: IMR90C4-derived pericyte-like cells integrate into a complete isogenic NVU model. A) Schematic of IMR90C4-derived BMEC co-culture set up with IMR90C4-derived NVU cell types. B) Maximum TEER achieved in IMR90C4-derived BMECs following monoculture or co-culture. Plotted are the means ±SD from 3 Transwells. Results are representative of 3 independent differentiations. *P<0.05 vs. monoculture; # P<0.05 vs. pericyte-like cell co-culture; % P<0.05 vs. astrocyte/neuron co-culture; ANOVA followed by Tukey's HSD test. C) Sodium fluorescein permeability in IMR90C4-derived BMECs following 48-hours of monoculture or co-culture. Plotted are the means ±SD from 3 Transwells. Results are representative of 3 independent differentiations. *P<0.05 vs. monoculture; ANOVA followed by Tukey's HSD test.

FIG. 12A-12D. NCSCs maintained in E6-CSFD retain neural crest marker expression and do not develop pericyte marker expression. A) Expression (FPKM) of selected transcripts in D15 NCSCs, D55 NCSCs (maintained in E6-CSFD for an additional 40 days), and all D25 pericyte-like cell samples ("H"). B) p75-NGFR immunocytochemistry analysis of NCSCs maintained in E6-CSFD for 3 months. Hoechst nuclear counter stain (blue) is also included. Scale bar: 200 µm. C) NG2 immunocytochemistry analysis of NCSCs maintained in E6-CSFD for 3 months. Hoechst nuclear counter stain (blue) is also included. Scale bar: 200 µm. D) NG2 immunocytochemistry analysis of H9-derived D22 pericyte-like cells, processed alongside and identically to the NCSC sample above. Hoechst nuclear counter stain (blue) is also included. Scale bar: 200 µm.

DETAILED DESCRIPTION OF THE INVENTION

Figures 1A, 1B, 1C, 1D, 1E, 1F, 1G, 1H, 1I, 1J:
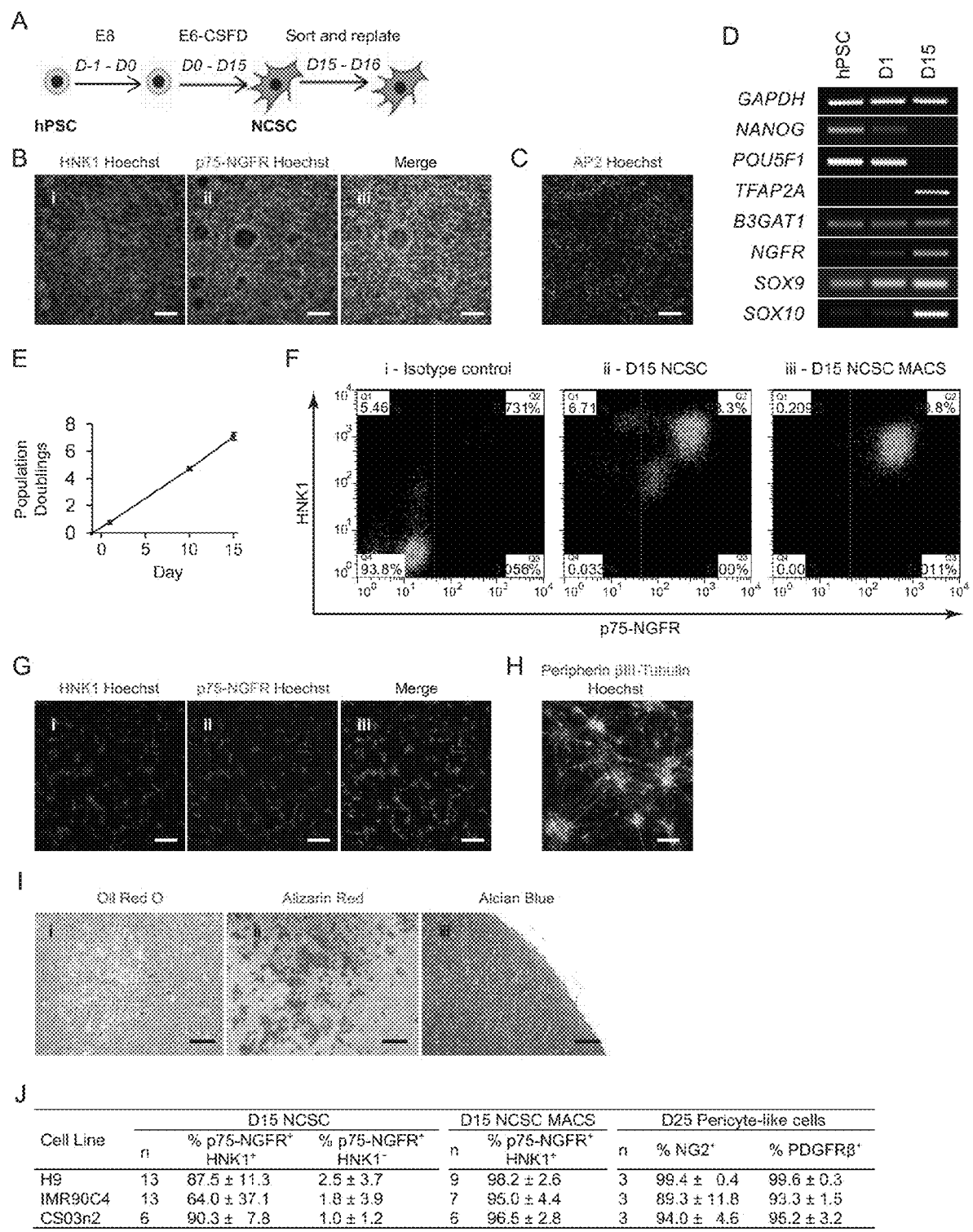
FIGS. 1A-1J. Generation of multipotent NCSC populations. A) NCSC differentiation timeline. Small molecule activation of canonical Wnt signaling and small molecule inhibition of Activin/Nodal/TGFβ/BMP signaling in minimal medium produces H9-derived NCSCs over a 15 day treatment window. NCSCs are then magnetically sorted and replated for subsequent mural cell differentiation. B) Immunocytochemistry images of H9 hESCs differentiated in E6-CSFD probed for the presence of HNK1 and p75-NGFR at D15. NCSCs are HNK1$^+$/p75-NGFR$^+$ cells. Hoechst nuclear counter stain (blue) is also included. Scale bar: 100 µm. C) AP-2 immunocytochemistry images for H9-derived NCSCs at D15. Hoechst nuclear counter stain (blue) is also included. Scale bar: 100 µm. D) Temporal PCR analysis of pluripotency (NANOG, POU5F1) and NCSC (TFAP2A, B3GAT1, NGFR, SOX9, SOX10) transcripts. E) Quantification of NCSC expansion in population doublings over the 15 days of NCSC differentiation. Plotted are the mean±SD of three technical replicates of a representative differentiation. F) Flow cytometry analysis of H9-derived NCSCs. Panels include isotype controls (panel i), NCSC (HNK1$^+$/p75-NGFR$^+$) purity prior to MACS (panel ii), and NCSC purity following MACS (panel iii). Inset percentages are included in each quadrant. Quantitation is shown in FIG. 1J. G) Immunocytochemistry analysis of D16 NCSCs following MACS and replating. NCSCs maintained HNK1 and p75-NGFR expression. Hoechst nuclear counter stain (blue) is also included. Scale bar: 100 µm. H) Immunocytochemistry analysis of H9-derived NCSCs subsequently differentiated in peripheral neuron medium. Resultant cells were positive for βIII-tubulin and peripherin expression. Hoechst nuclear counter stain (blue) is also included. Scale bar: 200 µm. I) H9-derived NCSCs could be differentiated into mesenchymal derivatives, including Oil Red O stained adipocytes (panel i, red), Alizarin red stained osteocytes (panel ii, red), and Alcian blue stained chondrocytes (panel ii, blue). Scale bar: 200 µm. J) NCSC and pericyte-like cell differentiation efficiencies. J) NCSC and pericyte-like cell differentiation efficiencies for three hPSC lines.

Abbreviations: blood-brain barrier, BBB; brain microvascular endothelial cells, BMECs; central nervous system, CNS; E6 medium supplemented with CHIR99021, SB431542, FGF2, and dorsomorphin, E6-CSFD; endothelial growth factor medium 2, EGM-2; human embryonic stem cells, hESCs; human pluripotent stem cells, hPSCs; induced pluripotent stem cells, iPSCs; neural crest stem cells, NCSC; neurovascular unit, NVU; vascular smooth muscle cells, vSMCs In General As discussed above, brain pericytes play an important role in the formation and maintenance of the neurovascular unit (NVU), and their dysfunction has been implicated in central nervous system (CNS) disorders. While human pluripotent stem cells (hPSCs) have been used to model other components of the NVU including brain microvascular endothelial cells (BMECs), astrocytes, and neurons, cells having brain pericyte-like phenotypes have not been described.

In the work supporting the present application, we generated neural crest stem cells (NCSCs), the embryonic precursor to forebrain pericytes, from human pluripotent stem cells (hPSCs) and subsequently differentiated NCSCs into brain pericyte-like cells. The brain pericyte-like cells expressed marker profiles that closely resembled primary human brain pericytes but lack the ACTA2 marker, which is found in primary pericytes. As disclosed below in the Examples, the brain pericyte-like cells self-assembled with endothelial cells to support vascular tube formation. Importantly, the brain pericyte-like cells also induced blood-brain barrier (BBB) properties in BMECs by at least 20%, preferably at least 30% or 50%, including barrier enhancement and reduction of transcytosis. Finally, brain pericyte-like cells were incorporated with iPSC-derived BMECs, astrocytes, and neurons to form an isogenic human NVU model that should prove useful for the study of the BBB in CNS health, disease, and therapy.

U.S. Ser. No. 13/793,466 (Publication US2017/025935), Ser. No. 13/218,123 (U.S. Pat. No. 8,293,495) and Ser. No. 16/092,450 (Publication US2019/0093084) are drawn to related technology and should be incorporated by reference herein. U.S. Ser. No. 13/218,123 discloses a preferred method of creating an isogenic BBB model (i.e., all of the cell types present are derived for a single patient iPSC line), which comprises BMECs, neurons, and astrocytes. At the time Ser. No. 13/218,123 was filed, the inventors had not finalized their pericyte differentiation protocol, nor had they shown that the addition of pericytes to the BBB resulted in a functional improvement. U.S. Ser. No. 13/793,466 discloses an improved BBB model that incorporates retinoic acid (RA). Both of these disclosures provide context for the use of the pericyte-like cells of the present invention.

The present invention also provides methods for obtaining a brain pericyte-like cell population and populations of the cells, including progenitor cells. The disclosure also include isogenic BBB models.

Cell Populations

In one embodiment, the present invention is a population of brain pericyte-like cells, wherein the cells expresses pericyte markers but do not express ACTA2 and wherein the cells are generated from hPSC.

Figures 2A, 2B, 2C, 2D, 2E, 2F, 2G, 2H, 2I, 2J:
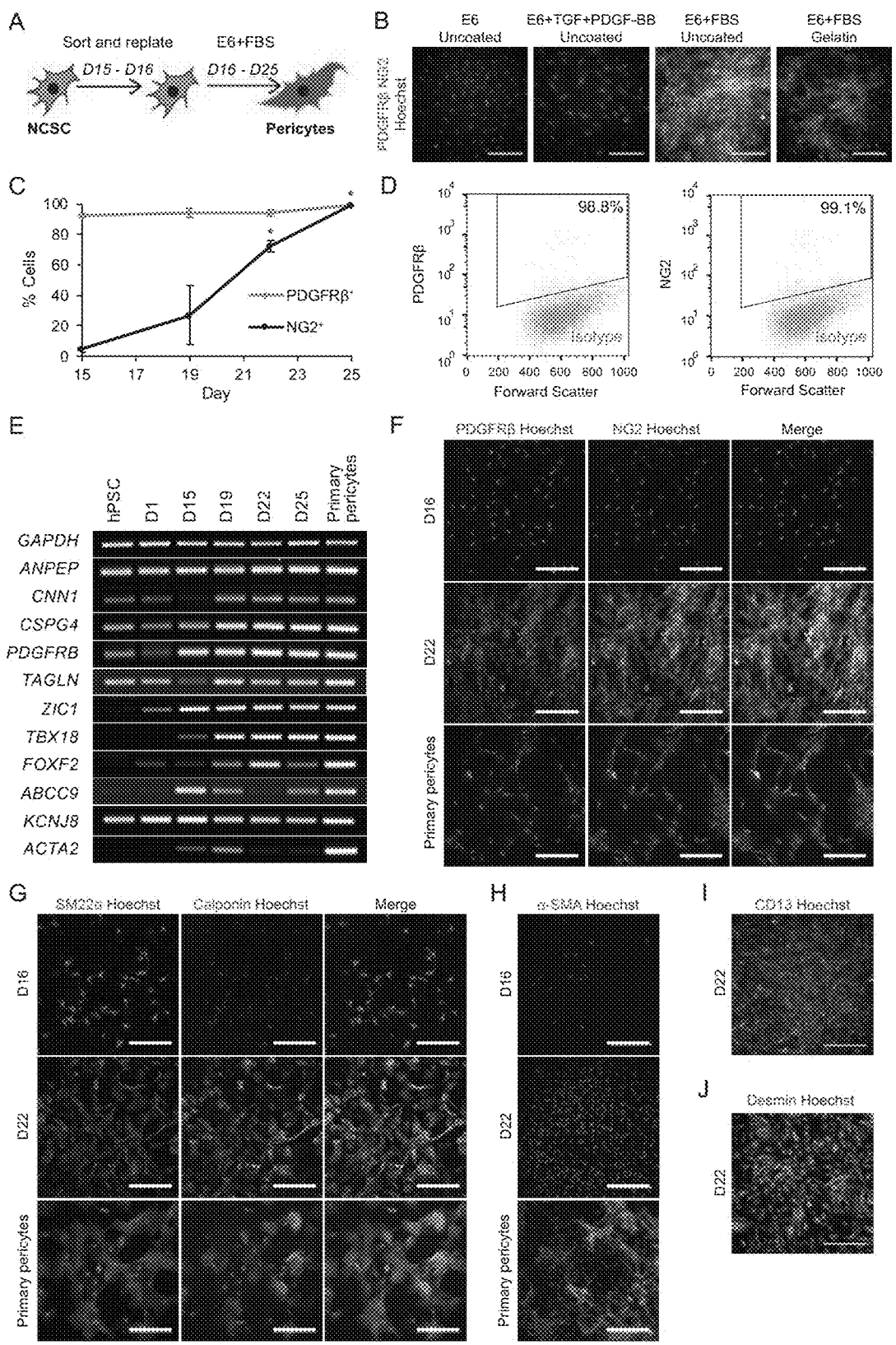
FIGS. 2A-2J. Serum treatment directs H9-derived NCSCs towards mural cells. A) Differentiation timeline for mural cell differentiation. Replated NCSCs are differentiated to mural cells in E6 medium plus 10% FBS for 9 days. B) PDGFRβ and NG2 immunocytochemistry of cells obtained after treating replated H9-derived NCSCs for 6 days in E6, E6+TGFβ1+PDGF-BB, or E6+10% FBS on uncoated tissue culture polystyrene, or E6+10% FBS on gelatin-coated tissue culture polystyrene. C) Temporal flow cytometry analysis for PDGFRβ and NG2 positive cells in H9-derived NCSCs treated with E6+10% FBS. Depicted are the means±SEM of at least two independent differentiations at each time point, *P<0.05 vs. D15 NCSC using ANOVA followed by Dunnett's test. D) Representative PDGFRβ and NG2 flow cytometry plots for H9-derived NCSC treated 9 days with E6+10% FBS medium. Quantitative data can be found in FIG. 1J. E) Temporal PCR analysis of mural and pericyte transcripts for the differentiating H9 hESCs. F) PDGFRβ and NG2 immunocytochemistry of H9-derived NCSCs (D16), mural cells (D22), and primary pericytes. Hoechst nuclear counter stain (blue) is also included. Scale bar: 200 µm. G) Calponin and SM22α immunocytochemistry of H9-derived NCSCs (D16), mural cells (D22) and primary pericytes. Hoechst nuclear counter stain (blue) is also included. Scale bar: 200 µm. H) α-SMA immunocytochemistry of H9-derived NCSCs (D16), mural cells (D22) and primary pericytes. Hoechst nuclear counter stain (blue) is also included. Scale bar: 200 µm. CD13 immunocytochemistry of H9-derived mural cells (D22). Hoechst nuclear counter stain (blue) is also included. Scale bar: 200 µm. J) Desmin immunocytochemistry of H9-derived mural cells (D22). Hoechst nuclear counter stain (blue) is also included. Scale bar: 200 µm.

By "pericyte markers," we mean the markers listed in the Examples below, including FIG. 2 (e.g., 2E and 2B). Note that the brain pericyte-like cells of the present invention do not express detectable ACTA2 (see FIG. 2B). Exemplary pericyte markers include CNN1, NG2, and PDGFRB. For example, the brain pericyte-like cells of the present invention are NG2$^+$ PDGFRB$^+$ ACTA2$^-$ cells. Exemplary pericyte markers that are expressed on the brain pericyte-like cells of the invention demonstrated in FIG. 2E and FIG. 9A include expression of one or more transcripts of pericyte markers selected from the group consisting of CSPG4, PDGFRB, CNN1, TAGLN, ANPEP, TBX18, ABCC9 and KCNJ8. In one suitable example, the brain pericyte-like cells express the transcripts of at least ABCC9 and KCNJ8.

Any appropriate method can be used to detect expression of biological markers characteristic of cell types described herein. For example, the presence or absence of one or more biological markers can be detected using, for example, RNA sequencing, immunohistochemistry, polymerase chain reaction, qRT-PCR, or other technique that detects or measures gene expression. Suitable methods for evaluating the above-markers are well known in the art and include, e.g., qRT-PCR, RNA-sequencing, and the like for evaluating gene expression at the RNA level. Quantitative methods for evaluating expression of markers at the protein level in cell populations are also known in the art. For example, flow cytometry is typically used to determine the fraction of cells in a given cell population that express (or do not express) a protein marker of interest (e.g., NG2, PDGFRB). In some cases, cell populations obtained by the differentiation methods of this disclosure comprise at least 80%, 85%, 90%, 95% and preferably at least 98% NG2+PDGFRB+ACTA2- brain pericyte-like cells.

The Examples below describe suitable hPSC lines. The human pluripotent stem cells may be embryonic stem cells or induced pluripotent stem cells (iPSCs). The present invention is also meant to employ iPSC lines are that developed from individual patients or disease models.

As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem cells (iPSCs). As used herein, "embryonic stem cells" or "ESCs" mean a pluripotent cell or population of pluripotent cells derived from an inner cell mass of a blastocyst. See Thomson et al., Science 282:1145-1147 (1998). These cells express Oct-4, SSEA-3, SSEA-4, TRA-1-60 and TRA-1-81, and appear as compact colonies having a high nucleus to cytoplasm ratio and prominent nucleolus. ESCs are commercially available from sources such as WiCell Research Institute (Madison, Wis.). As used herein, "induced pluripotent stem cells" or "iPSCs" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs. See, e.g., Yu et al., Science 318:1917-1920 (2007), incorporated by reference in its entirety. Induced pluripotent stem cells exhibit morphological properties (e.g., round shape, large nucleoli and scant cytoplasm) and growth properties (e.g., doubling time of about seventeen to eighteen hours) akin to ESCs. In addition, iPSCs express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPSCs is a non-pluripotent cell, such as a multipotent cell or terminally differentiated cell, such as somatic cells obtained from a post-natal individual.

The present invention provides an in vitro population of brain pericyte-like cells derived from human pluripotent stem cells, wherein the brain pericyte-like express pericyte markers but do not express ACTA2. In one embodiment, the pericyte markers include one or more of the following markers CNN1, NG2, and PDGFRB. In a preferred example, the in vitro derived population is NG2$^+$PDGFRB$^+$ brain pericyte-like cells. Alternatively, the in vitro derived population is NG2$^+$PDGFRB$^+$ACTA2$^-$ population of cells. The methods described below for generating the brain pericyte-like cells provide a substantially pure population of cells, for example, the methods provides a population that is at least 90% NG2$^+$PDGFRB$^+$.

As described more in the examples below, the brain pericyte-like cells further express calponin and SM22α but do not express α-SMA, distinguishing the cells from smooth muscle and other cell types. The hPSC-derived brain pericyte-like cells generated by the methods described herein express one or more transcripts of pericyte markers selected from the group consisting of CSPG4, PDGFRB, CNN1, TAGLN, ANPEP, TBX18, ABCC9 and KCNJ8. These hPSC-derived brain pericyte-like cells are capable of inducing pericyte-driven phenomena in BMEC, including the enhancement of barrier properties (e.g., increased TEER for the BMECs) and reduction of transcytosis (e.g., reduction in the ability to transport molecules across the in vitro made BMEC barrier).

The brain pericyte-like cells of the present invention typically are capable of associating with vascular networks. In the Example and as demonstrated in FIG. 4, the brain pericyte-like cells can self-assemble with HUVECs to form vascular cords and a method of measuring this phenomenon. This is an important component of pericyte function. In one embodiment, the present disclosure provides in vitro vascular tubes comprising $NG2^+PDGFRB^+ACTA2^-$ brain pericyte-like cells derived from PSCs and human umbilical vein endothelial cells (HUVECs) or immortalized human BMECs (hBMECs).

Figures 4A, 4B, 4C, 4D, 4E, 4F:
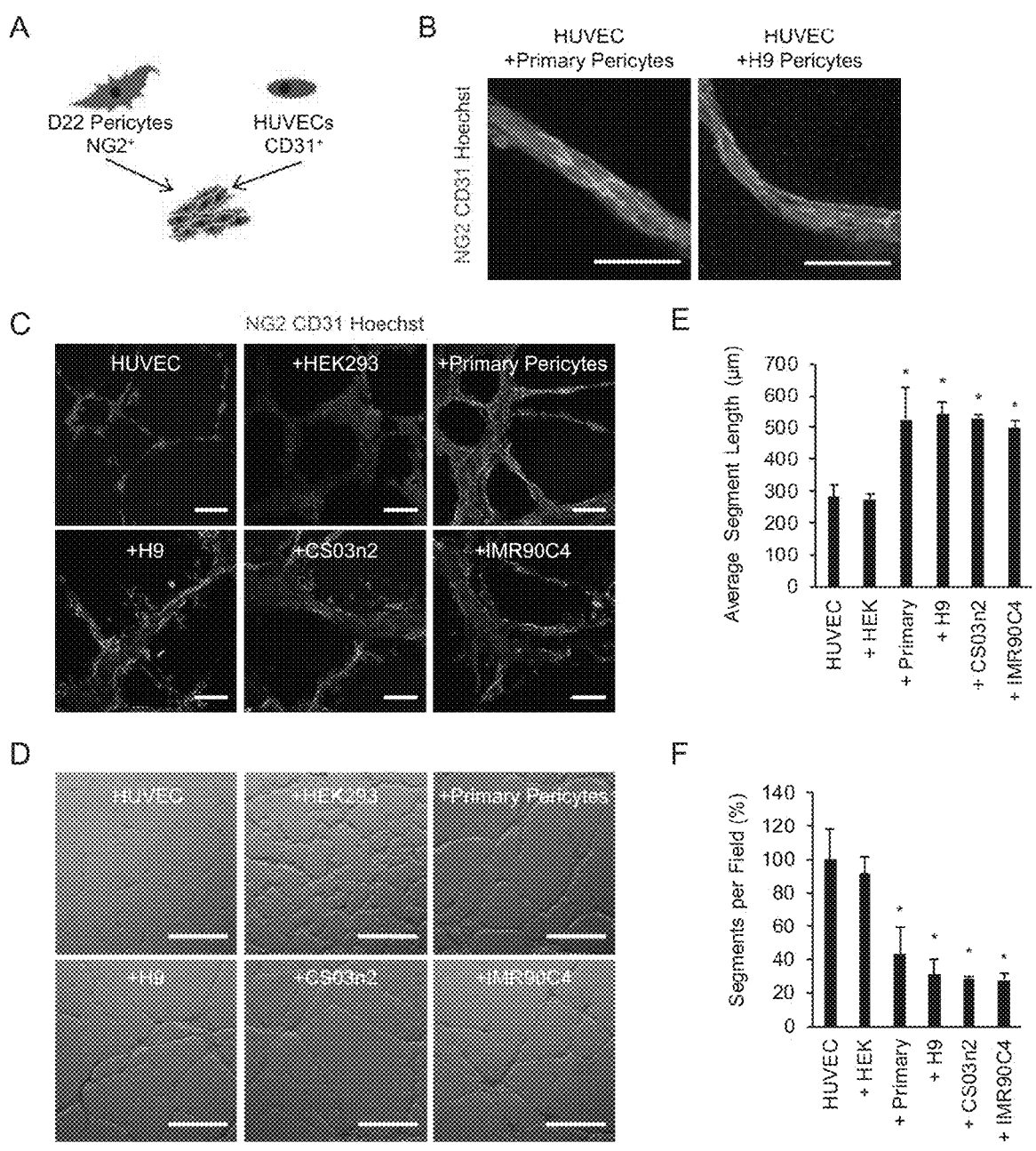
FIGS. 4A-4F. hPSC-derived pericyte-like cell assembly with endothelial cells. A) Self-assembly schematic. hPSC-derived pericyte-like cells self-assemble with HUVECs to form vascular cords. B) Confocal immunocytochemistry images of primary pericytes and H9-derived pericyte-like cells (NG2) aligning with and extending processes along HUVEC cords (CD31). Hoechst nuclear counter stain (blue) is also included. Scale bars: 50 µm. C) Immunocytochemistry images of HUVECs alone or cultured with HEK293 fibroblasts (+HEK293), primary human brain pericytes (+Primary Pericytes), CS03n2-derived pericyte-like cells (+CS03n2), H9-derived pericyte-like cells (+H9), or IMR90C4-derived pericyte-like cells (+IMR90C4). Hoechst nuclear counter stain (blue) is also included. Scale bars: 100 µm. D) Representative bright field images of HUVECs alone or cultured with the various cell types. Scale bars: 300 µm. E) Quantification of the average segment lengths from bright field images in panel D. Plotted are means±SEM of three independent pericyte-like cell differentiations. *P<0.05 vs. HUVEC monoculture; ANOVA followed by Dunnett's test. F) Quantification of the number of segments per field normalized to HUVEC monoculture from bright field images in panel D. Plotted are means±SEM of three independent pericyte-like cell differentiations. *P<0.05 vs. HUVEC monoculture; ANOVA followed by Dunnett's test.
Figures 13A, 13B, 13C, 13D, 13E:
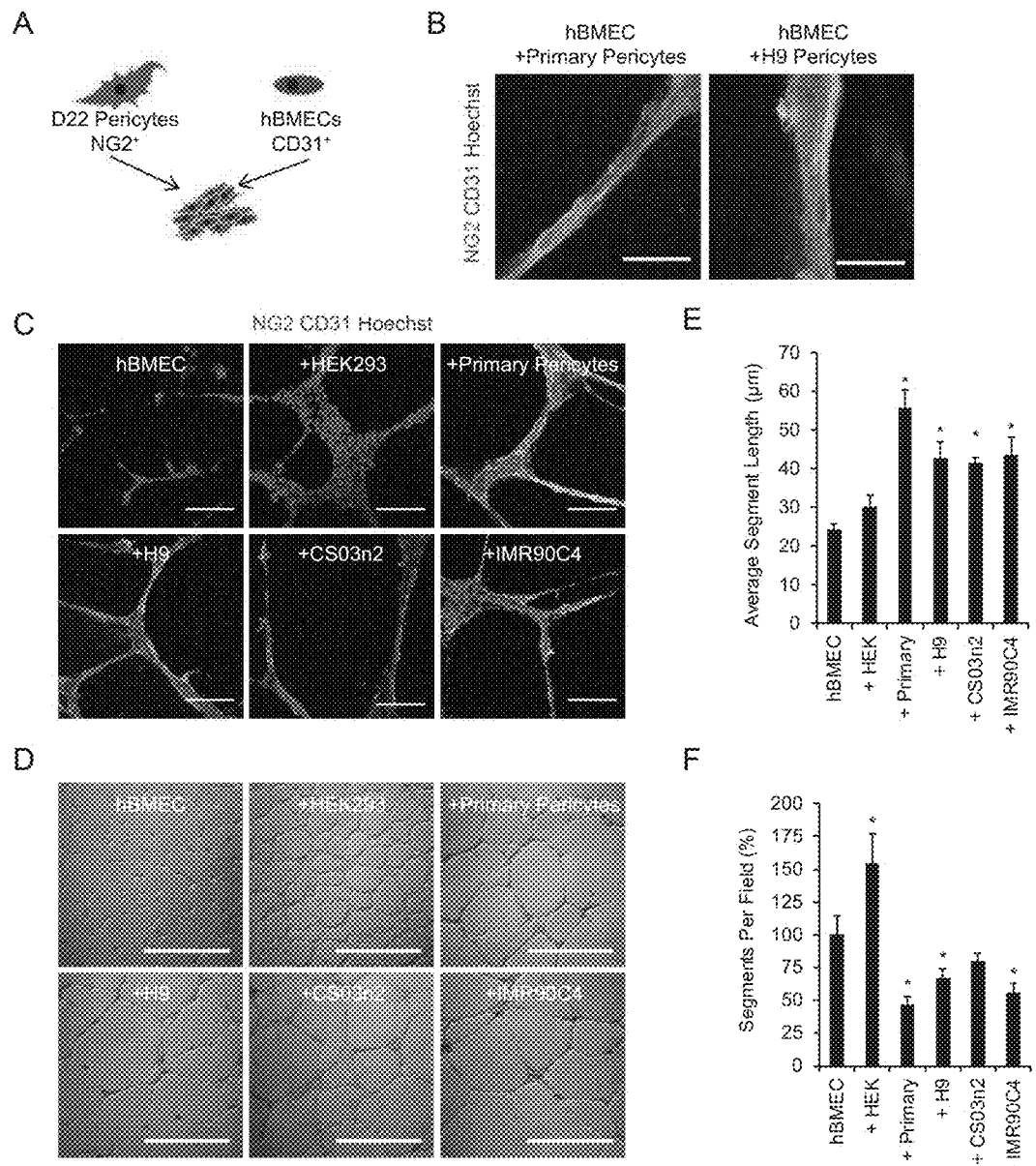
FIGS. 13A-13E: hPSC-derived pericyte-like cell assembly with brain endothelial cells. A) Self-assembly schematic. hPSC-derived pericyte-like cells self-assemble with hBMECs to form vascular cords. B) Confocal immunocytochemistry images of primary pericytes and H9-derived pericyte-like cells (NG2) aligning with and extending processes along hBMEC cords (CD31). Hoechst nuclear counter stain (blue) is also included. Scale bars: 50 µm. C) Immunocytochemistry images of hBMECs alone or cultured with HEK293 fibroblasts (+HEK293), primary human brain pericytes (+Primary Pericytes), CS03n2-derived pericyte-like cells (+CS03n2), H9-derived pericyte-like cells (+H9), or IMR90C4-derived pericyte-like cells (+IMR90C4). Hoechst nuclear counter stain (blue) is also included. Scale bars: 200 µm. D) Representative bright field images of HUVECs alone or cultured with the various cell types. Scale bars: 200 µm. E) Quantification of the average segment lengths from bright field images in panel D. Plotted are means ±SD of three imaging fields from one well. *P<0.05 vs. hBMEC monoculture; ANOVA followed by Dunnett's test. F) Quantification of the number of segments per field normalized to hBMEC monoculture from bright field images in panel D. Plotted are means ±SD of three imaging fields from one well. *P<0.05 vs. HUVEC monoculture; ANOVA followed by Dunnett's test.

The present invention provides methods of in vitro producing vascular cords for study. The hPSC-derived brain pericyte-like cells are plated on coated plates (e.g., MATRIGEL™, vitronectin, a vitronectin fragment, or a vitronectin peptide, or Synthemax® coated plates, preferably MATRIGEL™) with human umbilical vein endothelial cells (HUVECs, e.g., CD31+HUVECs) or immortalized human BMECs (hBMECs) self-associated with HUVECs and hBMECs much like primary human brain pericytes (FIG. 4B-C; FIG. 13B-C). After 24 hours in co-culture, hPSC-derived pericyte-like cells exhibited high NG2 expression and aligned along the $CD31^+$ endothelial cell cord perimeter and developed pericyte-like morphology with stellate-shaped bodies and extended cell processes (FIG. 4B-C). The hPSC-derived brain pericyte-like cells cocultured with which HUVECs or hBMECs yielded fewer yet longer and more developed cord networks (FIG. 4C-F, 13C-F) when compared to HUVECs or hBMECs alone and HUVECs or hBMECs in co-culture with control HEK293 cells (which yielded many small branching cords). Culture conditions include plating the hPSC-derived brain pericyte-like cells at a ratio of 3:1 (suitable ratios range from 4:1 to 2.5:1), in EGM-2 medium for at least 24 hours.

Figures 5A, 5B, 5C, 5D, 5E, 5F, 5G, 5H, 5I:
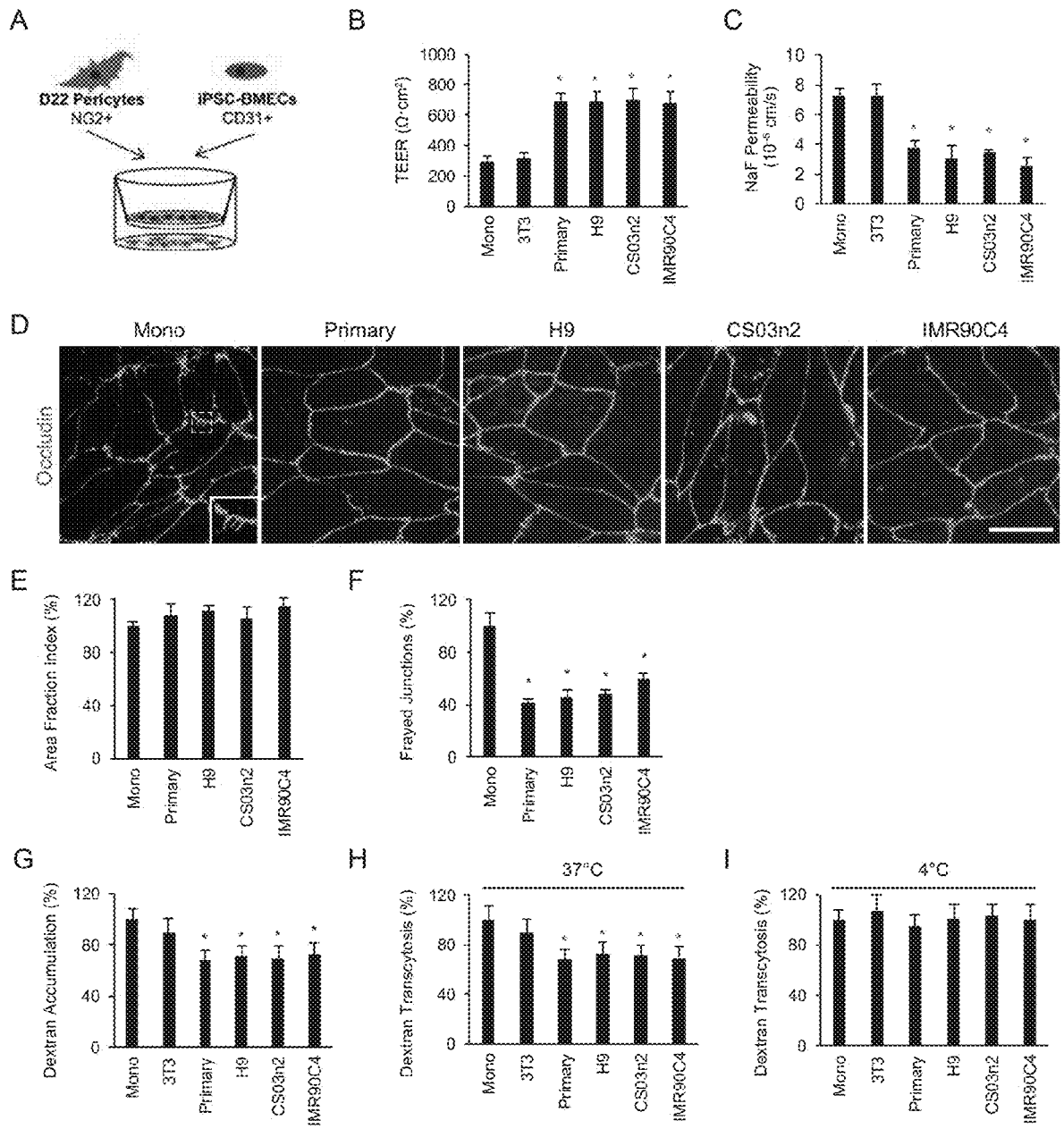
FIGS. 5A-5I. Measurement of the effects of hPSC-derived pericyte-like cells on BBB phenotypes. A) Schematic of Transwell setup for co-culture assays. B) Maximum TEER achieved by IMR90C4-derived BMEC monoculture or co-culture with 3T3 mouse fibroblasts, primary human brain pericytes, H9-derived pericyte-like cells, CS03n2-derived pericyte-like cells, or IMR90C4-derived pericyte-like cells. Plotted are the means±SEM of at least 3 independent differentiations per condition. *P<0.05 vs. monoculture; ANOVA followed by Dunnett's test. C) Sodium fluorescein permeability for IMR90C4-derived BMECs in monoculture or co-culture with cell types as described in B. Plotted are the means±SEM of at least 3 independent differentiations per condition, *P<0.05 vs. monoculture; ANOVA followed by Dunnett's test. D) Representative images of occludin immunocytochemistry of BMECs cultured for 48 h in EC medium (Mono) or EC medium conditioned by the cell types described in B. Enlarged example of a frayed junction is inset in the monoculture panel. Scale bar: 25 E) Quantification of occludin area fraction index for the samples described in D. Plotted are the means±SEM of 3 independent differentiations. No significant difference by ANOVA. F) Quantification of frayed junctions visualized by occludin immunocytochemistry for the samples described in D. Plotted are the means±SEM of 3 independent differentiations. *P<0.05 vs. monoculture; ANOVA followed by Dunnett's test. G) Accumulation of Alexa-488-tagged 10 kDa dextran in IMR90C4-derived BMECs following 48 hours of co-culture with cell types as described in B. All results are normalized to BMEC monoculture control. Plotted are the means ±SD of 3 Transwells. Results are representative of 3 independent differentiations. *P<0.05 vs. monoculture; ANOVA followed by Dunnett's test. H,I) Transcytosis of Alexa-488-tagged 10 kDa dextran at 37° C. (H) or 4° C. (I) across IMR90C4-derived BMECs following 48 hours co-culture with the cell types as described in B. All results are normalized to BMEC monoculture control. Plotted are the means ±SD from 3 Transwells. Results are representative of 3 independent differentiations. *P<0.05 vs. monoculture; ANOVA followed by Dunnett's test. No significant differences at 4° C. by ANOVA.

Additionally, the brain pericyte-like cells of the present invention typically are capable of inducing pericyte-driven phenomenon in BMEC. Most importantly, this would include the enhancement of barrier properties and reduction of transcytosis. For example, FIG. 5 shows the measurement of the effects of the brain pericyte-like cells of the present invention on BBB phenotypes. Briefly, hPSC-derived brain pericyte-like cells are co-cultured in a transwell system (e.g., polystyrene transwell filters with a 0.4 µm pore size) with iPSC-derived BMECs in endothelial cell (EC) medium without FGF2. The transwell coculture system is depicted in FIG. 5A, showing an upper compartment separated by a transwell insert containing a microporous semi-permeable membrane that separates the cells in the upper compartment (e.g., CD31+iPSC-derived BMECs) from the cells in the lower compartment (e.g., the NG2+PDGFRB+hPSC-derived brain pericyte-like cells of the present invention). Suitable EC medium are known in the art and commercially available (e.g., available from Promocell, R&D Systems, Sigma-Aldrich, ScienCell Research Laboratories, Lonza, among others), In one embodiment, the present invention is a population of NCSC cells prepared by the method described below.

Methods

In another embodiment, the present invention is a method of creating a population of brain pericyte-like cells, wherein the cells express pericyte markers but do not express ACTA2 and wherein the cells are generated from hPSC. In general, the method comprises the steps described below in the Examples. Typically, the method begins with culturing or maintaining hPSC in E8 medium. In some embodiments, this culture step is on coated plates, for example, Matrigel™ coated plates. The Examples below contain a description of E8 medium and a typical method of media preparation. The Examples below disclose a preferred method of singularizing the cells using Accutase and preferred seeding densities. As used herein, the terms "E8 culture medium" and "E8" are used interchangeably and refer to a chemically defined culture medium comprising or consisting essentially of DF3S supplemented by the addition of insulin (20 µg/mL), transferrin (10.67 ng/mL), human FGF2 (100 ng/mL), and human TGFβ1 (Transforming Growth Factor Beta 1) (1.75 ng/mL). The medium can be prepared based on the formula in previous publication (Chen et al., (2011) Nature Methods. 8(4), 424-429). As an alternative, the medium is also available from ThermoFisher/Life Technologies Inc. as Essential 8, or from Stem Cell Technologies as TeSR-E8.

Further differentiation steps include using E6 medium that is described herein and in U.S. Patent Publication No. 2014/0134732. Preferably, the chemically defined medium comprises DMEM/F-12. E6 medium contains DMEM/F12; L-ascorbic acid-2-phosphate magnesium (64 mg/1); sodium selenium (14 µg/1); insulin (20 mg/1); $NaHCO_3$ (543 mg/1); and transferrin (10.7 mg/1). E6-CSFD is E6 medium supplemented with CHIR99021, SB431542, FGF2, and dorsomorphin. Suitable ranges of the factors are for inclusion in E6 medium to produce E6-CSFD media includes, for example, about 0.5-5 µM CHIR99021 (preferably 1 µM), a GSK3β inhibitor to promote WNT signaling; 5-20 µM SB431543 (preferably 10 µM), an ALK5 antagonist to inhibit Activin/Nodal/TGFβ signaling; 5-100 ng/ml FGF2 (preferably 10 ng/mL); and about 0.5-2 µM dorsomorphin (preferable 1 µM), a BMP type I receptor inhibitor. One exemplary formulation of E6-CSFD is 1 µM CHIR99021; 10 µM SB431543; 10 ng/mL FGF2 (E6-CSF); and 1 µM CHIR99021, and 1 µM dorsomorphin.

One would then culture the in vitro hPSCs described above in E6-CSFD medium for about 15 days to produce a population comprising NCSCs. Suitable, the cells can be cultured for at least 15 days, and can be maintained in culture to about 60 days.

One would then typically sort and re-plate the NCSC cells, which express HNK1 and p75-NGFR (e.g., p75-$NGFR^+HNK1^+$ NCSCs) and can be differentiated to various mesenchymal derivatives such as osteocytes, adipocytes and chondrocytes under different culturing conditions as described in the Examples below.

One would then culture the NCSC cells (e.g., p75-$NGFR^+$ $HNK1^+$ NCSCs) in E6 medium with an addition of serum (preferably 1-10%) for about 11 days, wherein a population of PSC-derived brain pericyte-like cells that express pericyte markers but do not express ACTA2 can be isolated, this cell population is described in more detail above. These could be further cultured as brain pericyte-like cells for about 30 additional days (e.g., from 11 to 41 days).

In one embodiment, a method of creating a population of p75-$NGFR^+HNK^+NSCs$ from human pluripotent stem cells is provided. The method comprises culturing hPSC in E6-CSFD medium for about 15 days to produced p75-$NGFR^+HNK^+NCSC$ cells, subsequently sorting p75-$NGFR^+$ cells from the population and re-plating the p75-

NGFR+ cells of step to produce a population of p75-NGFR+ NCSCs. Methods of sorting the p75-NGFR+ cells are known to one skilled in the art and include, but are not limited to, fluorescence activated cell sorting (FACS) and magnetic-activated cell sorting (MACS), among others. A preferred method of sorting the cells is MACS.

The population of cells produced from PSCs is a p75-NGFR+HNK+AP-2+NCSCs which are able to be maintained in culture, e.g., the cells are able to double at least 5 times in culture and still maintain expression p75-NGFR+·HNK+, and AP-2+ within the cells. These NCSCs are able to be maintained in culture for at least five passages and maintain NGFRIINK+AP-2+ marker expression and do not express pericyte markers (e.g., NG2−, PDBGFR−, etc). These NCSCs produced by the method described herein are able to maintain the potential to differentiate into neurons and mesenchymal cells, as demonstrated in the Examples below.

In vitro derived hPSC-derived brain pericyte-like cells can be produced from these NCSC cells. The method of producing hPSC-derived brain pericyte-like cells (e.g., NG2+PDGFRB+ hPSC-derived brain pericyte-like cells) comprises culturing the NCSC cells (e.g., p75-NGFR+HNK+AP-2+NCSCs) in E6 media with an addition of 1-10% serum for about 11 days, wherein the NCSCs produce a population of brain pericyte-like cells that express NG2, and PDGFRB but do not express ACTA2.

In another embodiment, the disclosure provides a method of creating a population of hPSC-derived brain pericyte-like cells comprising the steps of (a) culturing hPSC in E6-CSFD medium for about 15 days to produced p75-NGFR+HNK+ NCSC cells, (b) sorting p75-NGFR+ cells and re-plating the p75-NGFR+ cells to produce a population of p75-NGFR+ NCSCs, and (c) culturing the cells of step (b) in E6 media with an addition of 1-10% serum for about 11 days to generate a population of brain pericyte-like cells that express pericyte markers but do not express ACTA2 is produced. The population of hPSC-derived brain pericyte-like cells express one or more marker selected from the group consisting of CNN1, NG2, and PDGFRB, e.g., NG2+PDGFRB+ hPSC-derived brain pericyte-like cells. The population of brain pericyte-like cells can be further characterized by the express one or more transcripts of pericyte markers selected from the group consisting of CSPG4, PDGFRB, CNN1, TAGLN, ANPEP, TBX18, ABCC9 and KCNJ8. This method produces an hPSC-derived brain pericyte-like cell population that is at least 90% NG2+PDGFRB+.

As discussed above, these hPSC-derived brain pericyte-like cells can be used in a variety of assays and models, including an isogenic human NVU model and an isogenic BBB model.

An Isogenic BBB Model

In another embodiment, the present invention is a BBB model created by the method disclosed in U.S. Ser. No. 13/793,466 (US2017/025935) or any other method of using pericytes in the creation of a BBB model (multicellular BBB model). Most preferably, the model is an isogenic model. The term "isogenic" as used herein, refers to cells originating or differentiated from the same subject or same line of human pluripotent stem cells (hPSCs). The cells are not exposed to cells of an alternate genetic origin as the model is being prepared. In the present invention, hPSC derived brain pericyte-like cells are co-cultured with BMECs derived from the same hPSC source to create an isogenic blood brain barrier model.

In a previous U.S. patent application (Ser. No. 13/155,435, U.S. Patent Publication No. 2012/0015395, incorporated herein by reference), Applicants demonstrated that human pluripotent stem cells could be differentiated into brain microvascular endothelial cells (BMECs). In another previous U.S. patent application (Ser. No. 13/793,466, U.S. Patent Publication No. 2014/0127800, incorporated herein by reference).

The BBB model contemplated herein would be entirely derived from in vitro hPSC-derived cells. The hPSC-derived brain pericyte-like cells described herein can be used in the BBB model using a transwell system to coculture BMECS and supporting cells (e.g., pericytes,) mimic a blood brain barrier using in vitro iPSC-derived BMECs (CD31+ BMECs). This model is described in US that provide Ser. No. 13/793,466. BBB models can be used to help elucidate the role of the BBB in brain development, function, and disease, and to develop potential therapeutic approaches. However, BBB models using primary and transformed BMECs tend to de-differentiate and lose their barrier properties once they are removed from the brain microenvironment and often exhibit sub-par BBB phenotypes (Weksler et al. 2005, Förster et al. 2008, Man et al. 2008, Calabria & Shusta 2008). The brain pericyte-cells of the present invention would allow for the use of a fully in vitro derived BBB from hPSCs.

Examples

Directed Differentiation of hPSCs to NCSCs in Low Protein Medium

Figures 7A, 7B, 7C, 7D, 7E, 7F, 7G, 7H, 7I, 7J:
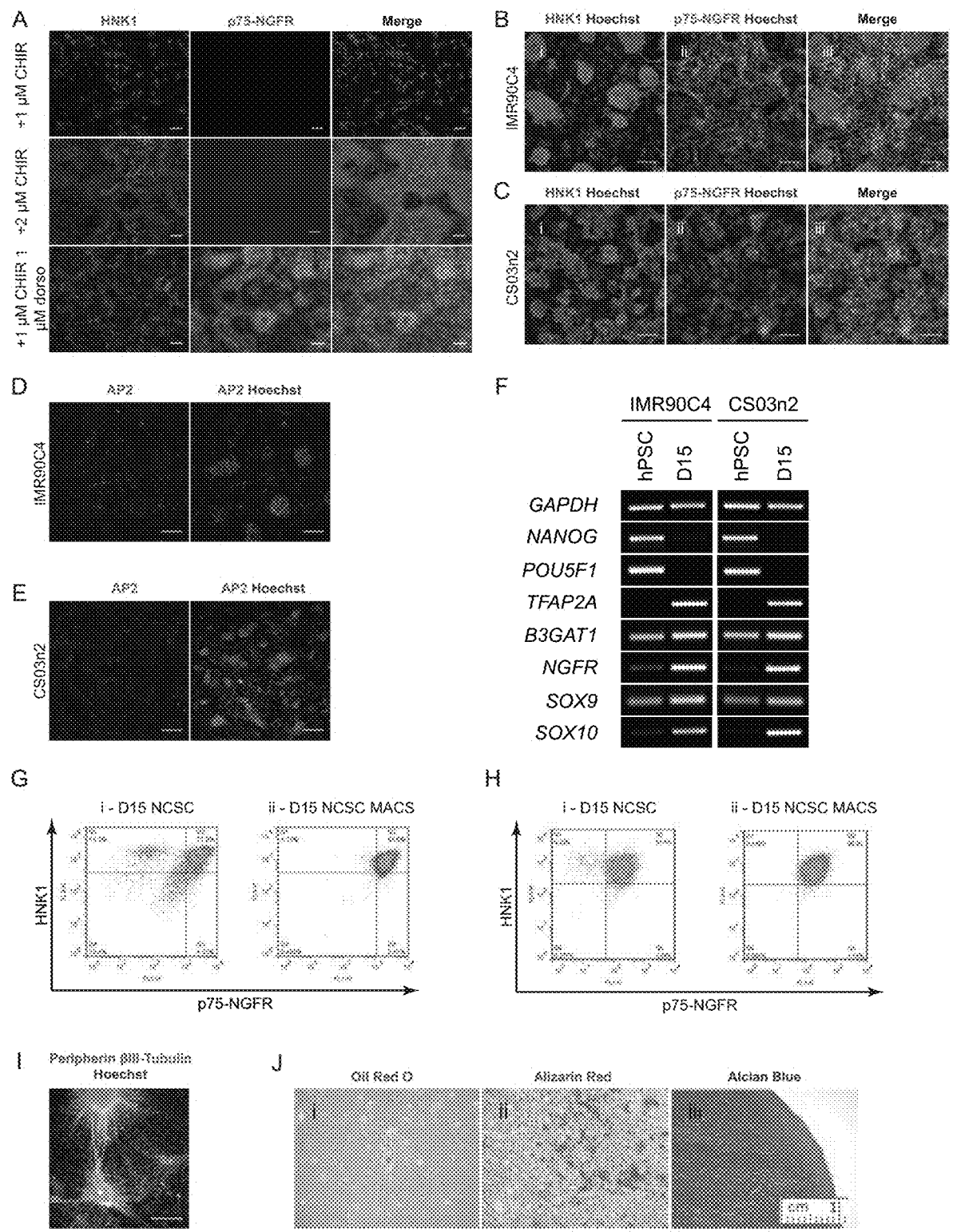
FIGS. 7A-7J: Generation of multipotent NCSC populations from multiple hPSC lines. A) Immunocytochemistry images of small molecule screen (n=1) on HNK1 and p75-NGFR expression in cells differentiated from H9 hESCs. Cells were cultured fifteen days in E6+10 ng/mL FGF2+22.5 µg/mL heparin+10 µM SB431542+CHIR99012±dorsomorphin at the indicated concentrations. Hoechst nuclear counter stain (blue) is also included. Scale bars: 100 µm. B) Immunocytochemistry images of IMR90C4 iPSCs differentiated in E6-CSFD probed for the presence of HNK1 and p75-NGFR at D15. Hoechst nuclear counter stain (blue) is also included. Scale bars: 100 µm. C) Immunocytochemistry images of CS03n2 iPSCs differentiated in E6-CSFD probed for the presence of HNK1 and p75-NGFR at D15. Hoechst nuclear counter stain (blue) is also included. Scale bars: 100 µm. D) AP-2 immunocytochemistry images for IMR90C4-derived NCSCs at D15. Hoechst nuclear counter stain (blue) is also included. Scale bar: 100 µm. E) AP-2 immunocytochemistry images for CS03n2-derived NCSCs at D15. Hoechst DNA nuclear stain (blue) is also included. Scale bar: 100 µm. F) Temporal PCR analysis of pluripotency (NANOG, POU5F1) and NCSC (TFAP2A, B3GAT1, NGFR, SOX9, SOX10) transcripts in IMR90C4 and CS03n2 iPSCs and NCSC progeny. G) Flow cytometry analysis of IMR90C4-derived NCSCs. Panels include NCSC (HNK1$^+$/p75-NGFR$^+$) purity prior to MACS (panel i), and NCSC purity following MACS (panel ii). Inset percentages are included in each quadrant. Quantitation is shown in Table 1. H) Flow cytometry analysis of CS03n2-derived NCSCs. Panels include NCSC (HNK1$^+$/p75-NGFR$^+$) purity prior to MACS (panel i), and NCSC purity following MACS (panel ii). Inset percentages are included in each quadrant. Quantitation is shown in Table 1. I) Immunocytochemistry analysis of IMR90C4-derived NCSCs subsequently differentiated in peripheral neuron medium. Resultant cells were positive for βIII-tubulin and peripherin expression. Hoechst nuclear counter stain (blue) is also included. Scale bar: 100 µm. J) IMR90C4-derived NCSCs could be differentiated into mesenchymal derivatives, including Oil Red O stained adipocytes (panel i, red), Alizarin red stained osteocytes (panel ii, red), and Alcian blue stained chondrocytes (panel ii, blue).
Figures 8A, 8R:
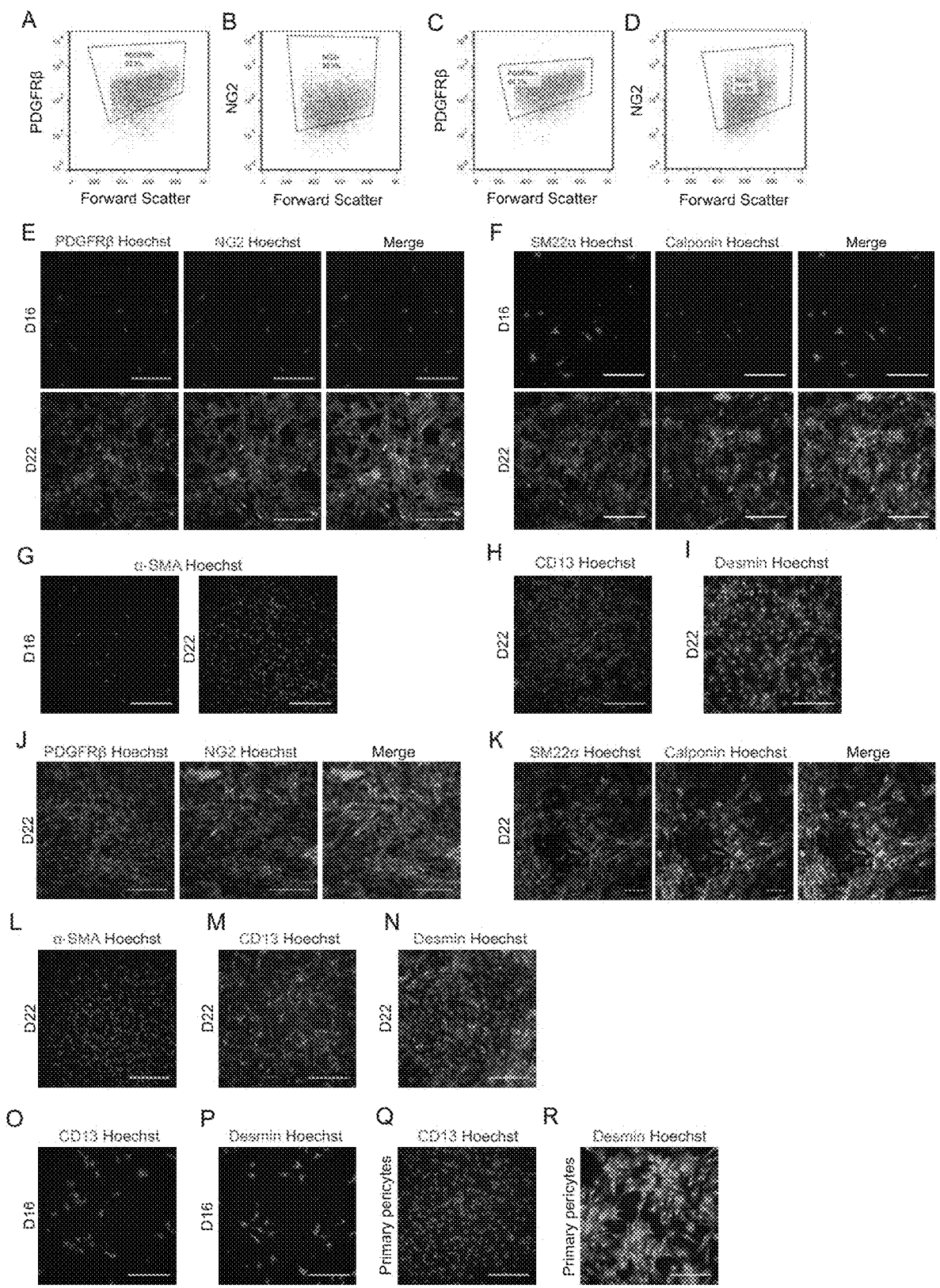
FIGS. 8A-8R: Serum treatment directs C-derived NCSCs towards mural cells. A, B) Representative PDGFRβ and NG2 flow cytometry plots for IMR90C4-derived NCSCs treated for 9 days with E6+10% FBS medium. C, D) Representative PDGFRβ and NG2 flow cytometry plots for CS03n2-derived NCSCs treated for 9 days with E6+10% FBS medium. Quantitative results can be found in FIG. 1J. E) PDGFRβ and NG2 immunocytochemistry of IMR90C4-derived NCSCs (D16) and mural cells (D22). Hoechst nuclear counter stain (blue) is also included. Scale bar: 200 µm. F) Calponin and SM22α immunocytochemistry of IMR90C4-derived NCSCs (D16) and mural cells (D22). Hoechst nuclear counter stain (blue) is also included. Scale bar: 200 µm. G) α-SMA immunocytochemistry of IMR90C4-derived NCSCs (D16) and mural cells (D22). Hoechst nuclear counter stain (blue) is also included. Scale bars: 200 µm. H,I) CD13 and desmin immunocytochemistry of IMR90C4-derived mural cells (D22). Hoechst nuclear counter stain (blue) is also included. Scale bars: 200 µm. J) PDGFRβ and NG2 immunocytochemistry of CS03n2-derived mural cells (D22). Hoechst nuclear counter stain (blue) is also included. Scale bar: 200 µm. K) Calponin and SM22α immunocytochemistry of CS03n2-derived mural cells (D22). Hoechst nuclear counter stain (blue) is also included. Scale bar: 200 µm. L) α-SMA immunocytochemistry of CS03n2-derived mural cells (D22). Hoechst DNA nuclear stain (blue) is also included. Scale bars: 200 µm. M,N) CD13 and desmin immunocytochemistry of CS03n2-derived pericyte-like cells (D22). Hoechst nuclear counter stain (blue) is also included. Scale bars: 200 µm. O,P) CD13 and desmin immunocytochemistry of H9-derived NCSCs (D16). Hoechst nuclear counter stain (blue) is also included. Scale bars: 200 µm. Q,R) CD13 and desmin immunocytochemistry of primary brain pericytes. Hoechst nuclear counter stain (blue) is also included. Scale bars: 200 µm.

We first assessed the capability of E6, a reduced factor medium, to support differentiation of H9 human embryonic stem cells (hESCs) and IMR90C4 and CS03n2 induced pluripotent stem cells (iPSCs) to NCSCs. H9 hESCs were cultured for 15 days in E6 medium supplemented with heparin and pathway modulators previously implicated in hPSC differentiation to NCSCs (48): 1 µM CHIR99021, a GSK3β inhibitor to promote WNT signaling; 10 µM SB431543, an ALK5 antagonist to inhibit Activin/Nodal/TGFβ signaling; and 10 ng/mL FGF2 (E6-CSF). However, E6-CSF failed to produce p75-NGFR+/HNK1+ NCSCs, and increasing CHIR99021 concentration (2 µM) did not aid in inducing p75-NGFR expression (FIG. 7A).

BMP signaling during hPSC differentiation to NCSC can inhibit NCSC formation, and WNT signaling activation can induce downstream BMP signaling in hPSCs (46); however, the requirement of BMP inhibition in NCSC differentiation has been variable (42, 46). To examine the effects of BMP inhibition on hPSC differentiation to NCSCs in minimal medium, E6-CSF medium was supplemented with 1 µM dorsomorphin, a BMP type I receptor inhibitor, to generate E6-CSFD. With BMP inhibition, H9 hESCs progressed to p75-NGFR+/HNK1+ NCSCs that also expressed AP-2 after 15 days of E6-CSFD treatment (FIG. 1A-C,J; FIG. 7D,E). E6-CSFD also drove NCSC formation in IMR90C4 and CS03n2 iPSC lines (FIG. 1J; FIG. 7B-E). H9 and CS03n2 hPSCs yielded cultures comprising ~90% NCSCs, while purity of IMR90C4-derived NCSCs was frequently lower (FIG. 1J). Temporal mRNA analysis confirmed loss of pluripotency by D15 of E6-CSFD treatment, as indicated by loss of NANOG and POU5F1 pluripotency transcripts (FIG. 1D; FIG. 7F). In addition, after 15 days of E6-CSFD treatment, the differentiation mixture expressed NCSC-associated transcripts, including TFAP2A, SOX9, SOX10, B3GAT1 (HNK1) and NGFR (FIG. 1D; FIG. 7F). At D15 of E6-CSFD treatment, cells had undergone approximately 7 population doublings (FIG. 1E), corresponding to over 100 NCSCs per input hPSC.

To purify NCSCs from the differentiation cultures, day 15 NCSCs were positively selected using anti-p75-NGFR magnetic activated cell sorting (MACS). MACS enriched p'75-NGFR$^+$HNK1$^+$ NCSC populations above 95% for all three hPSC lines tested (FIG. 1F,J; FIG. 7G,H). Sorted NCSCs retained p75-NGFR and HNK1 expression following replating (FIG. 1G). In addition, treating NCSCs with N2 medium supplemented with BDNF, GDNF, NT-3, and NGF-β yielded βIII-tubulin$^+$/peripherin$^+$ peripheral neurons (FIG. 1H; FIG. 7I). We additionally expanded sorted NCSCs for 11 days and then differentiated these cells to mesenchymal derivatives: Oil Red O$^+$ adipocytes were obtained by treating NCSCs with insulin, IBMX, and dexamethasone, Alcian blue$^+$ chondrocytes using pellet culture and TGFβ1-containing chondrogenic medium, and Alizarin red$^+$ osteocytes using dexamethasone, glycerophosphate, and ascorbic acid (FIG. 1I; FIG. 7J). Taken together, these data demonstrate that reduced factor, low protein E6-CSFD medium directs hPSCs to NCSCs over a 15-day differentiation period, and that MACS-purified NCSCs retain the potential to form NCSC derivatives.

Serum Treatment Directs hPSC-Derived NCSCs to Mural Cell Lineages

We subsequently identified differentiation conditions capable of driving NCSCs to mural cell lineages (FIG. 2A), as defined by coexpression of PDGFRβ and NG2 (40, 49). PDGFRβ was expressed in D15 NC SCs (FIG. 2C) and in replated cells one day following MACS (D16), but NG2 expression was absent in both of these cell populations (FIG. 2C,F). Given the importance of platelet-derived growth factor-BB (PDGF-BB) and TGFβ1 in mural cell development (50, 51), we first tested if these factors could induce NG2 expression in NCSCs while also maintaining PDGFRβ expression. Culture of NCSCs for six days in E6 medium generated cells that were PDGFRβ positive but NG2 expression was not observed (FIG. 2B). Supplementation of E6 medium with PDGF-BB and TGFβ1 did not induce NG2 expression. However, when E6 medium was supplemented with 10% FBS, resultant cells expressed both PDGFRβ and NG2 (FIG. 2B). Comparing differentiation in E6+10% FBS on uncoated tissue culture polystyrene (TCPS) to gelatin-coated TCPS, which has previously been reported as conducive to mural cell differentiation (52), the uncoated substrate yielded a qualitatively larger fraction of cells that expressed PDGFRβ and NG2 (FIG. 2B). Given the capacity for E6+10% FBS on uncoated substrate to direct hPSC-derived NCSCs to PDGFRβ$^+$/NG2$^+$ mural cells, we further evaluated these cells.

The temporal evolution of hPSC-derived NCSCs to PDGFRβ$^+$/NG2$^+$ mural cells using E6+10% FBS was examined over a 9 day period (D16-D25). At D15 of differentiation, 92.4±1.1% of H9-derived NCSCs expressed PDGFRβ, and after 9 days of serum treatment, nearly all cells were PDGFRβ$^+$ (99.6±0.2%) (FIG. 2C-D), with expression of PDGFRB transcript present in D15 NCSCs and throughout the differentiation in serum (FIG. 2E). In contrast, despite the fact that the NG2-encoding CSPG4 transcript was expressed in D15 NCSCs (FIG. 2E), NG2 protein was not detected at this time point by flow cytometry (FIG. 2C). However, the percentage of cells expressing NG2 increased over the 9 day differentiation period, with nearly all cells becoming NG2$^+$ (99.4±0.3% at D25, P<0.05 vs. D15) (FIG. 2C-D). The E6+10% FBS differentiation scheme also generated at least ~90% PDGFRI$^+$ and NG2$^+$ cells in IMR90C4- and CS03n2-derived NCSCs following nine days of E6+10% FBS treatment (D25; FIG. 1J; FIG. 8A-D). At D22, this procedure yielded a roughly ten-fold expansion in mural cells (9.5±1.3 mural cells per sorted NCSC for six independent differentiations).

Figures 9A, 9B, 9C, 9D, 9E, 9F:
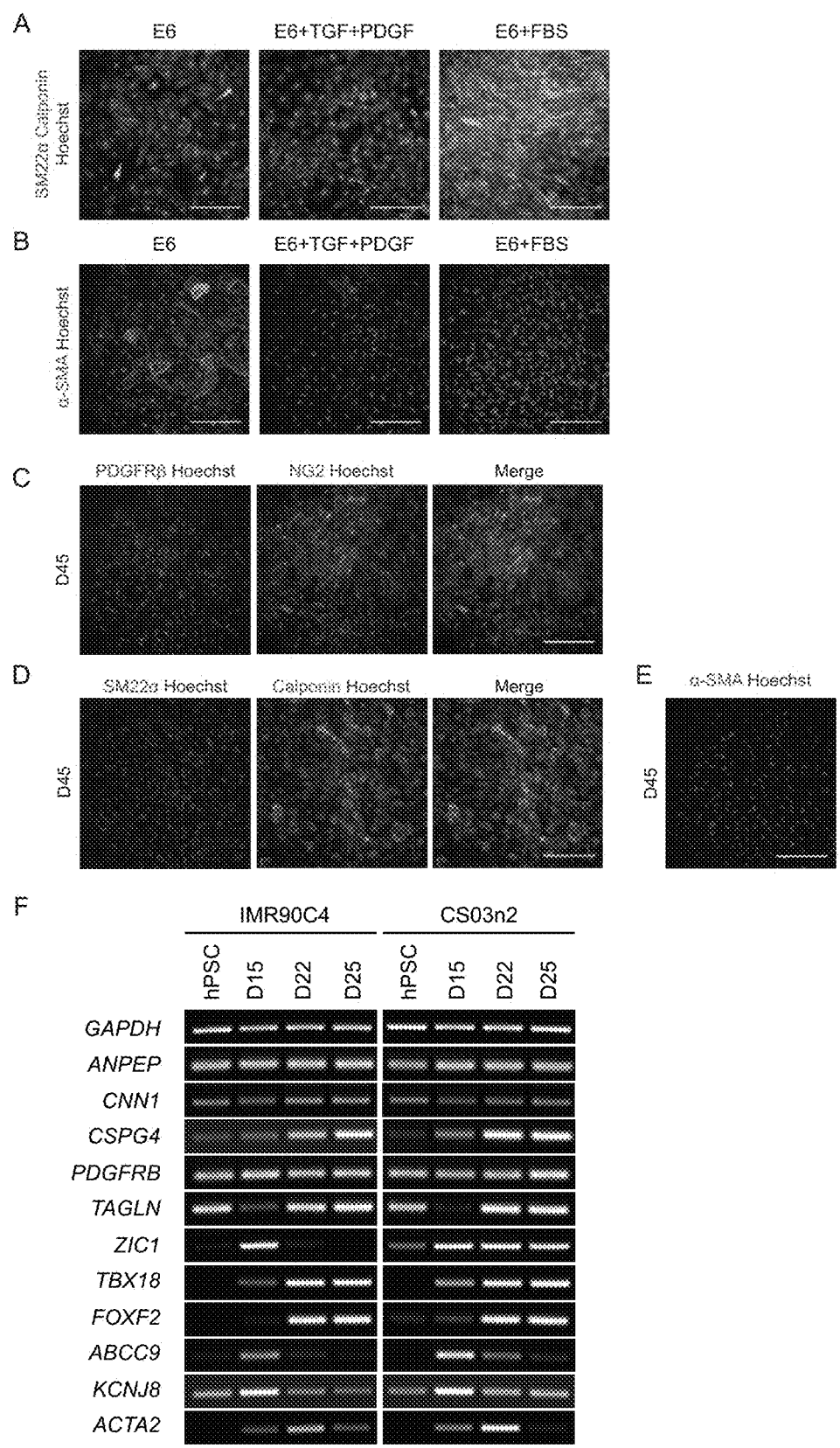
FIGS. 9A-9F: Supplemental analysis of hPSC-derived pericyte-like cells. A,B) Analysis of cells obtained by culturing NCSCs in E6, E6+TGFβ1+PDGF-BB, or E6+10% FBS for 6 days. Calponin, SM22α, and α-SMA immunocytochemistry. Hoechst nuclear counter stain (blue) is also included. Scale bars: 200 µm. C,D,E) Long-term maintenance of hPSC-derived pericyte-like cells. PDGFRβ, NG2, calponin, SM22α, and α-SMA immunocytochemistry of H9-derived pericyte-like cells maintained in E6+10% FBS to D45. Hoechst nuclear counter stain (blue) is also included. Scale bars: 200 µm. F) Temporal PCR analysis of mural and pericyte transcripts for the differentiating IMR90C4 and CS03n2 iPSC lines.

To further probe the transition of hPSC-derived NCSCs to pericyte-like cells, we examined the temporal evolution of transcripts that have been associated with pericytes and other mural cells. H9 hESCs expressed CNN1 (calponin) and TAGLN (SM22α), which encode contractile proteins implicated in early mural cell differentiation (41), as did NCSCs and mural cells (FIG. 2E). At D16, replated hPSC-derived NCSCs expressed SM22α but calponin expression was not observed (FIG. 2G; FIG. 8F,K). By D22, differentiating hPSC-derived NCSCs exhibited calponin/SM22α coexpression with cellular localization to contractile fibers (FIG. 2G; FIG. 8F,K). Interestingly, smooth muscle actin (α-SMA) was not detected in D22 cells treated with E6+10% FBS, although serum transiently increased abundance of the transcript (ACTA2) before downregulation (FIG. 2E,H; FIG. 8G,L; FIG. 9F). In contrast, NCSCs treated with E6 alone or E6 plus PDGF-BB and TGFβ1 expressed α-SMA in addition to calponin and SM22α (FIG. 9A,B). In addition, these cells exhibited a morphology similar to smooth muscle cells, with large cell bodies and distinct cell borders, whereas the cells differentiated in E6+10% FBS were smaller with numerous projections reminiscent of cultured primary brain pericytes (FIG. 2G,H). After extended culture in E6+10% FBS (D45), the resultant cells continued to be PDGFRβ$^+$/NG2$^+$ and expressed calponin and SM22α while α-SMA was still absent (FIG. 9C-E). Primary human brain pericytes expressed all three contractile proteins, and had a morphology similar to the serum treated NCSC-derived mural cells (FIG. 2F-H). CD13 and desmin were expressed both in D16 NCSCs and D22 mural cells, while primary brain pericytes expressed desmin but CD13 expression was weak (FIG. 2I,J; FIG. 8H,I,M-R).

Additional transcript analysis was used to further characterize the differentiation process. The mural cell marker, ANPEP (CD13), was expressed throughout the differentiation process. While PDGFRB, CSPG4 (NG2), CNN1, TAGLN, ANPEP, and TBX18 are mural cell markers expressed throughout the body, FOXF2 and ZIC1 have been suggested as being selectively expressed in brain mural cells (53-55). Accordingly, given the NCSC origin of the mural cells, FOXF2 and ZIC1 were induced during the differentiation (FIG. 2E; FIG. 9F). Until recently, it had been difficult to use markers to distinguish pericytes from smooth muscle cells in brain; however, it has been suggested that ABCC9 and KCNJ8 are two transcripts having selective expression in brain pericytes as compared to smooth muscle (40, 49). ABCC9 levels were biphasic with strong expression in D15 NCSC and then a re-induction in D25 mural cells. KCNJ8 was expressed fairly uniformly throughout the differentiation process (FIG. 2E). Similar results were observed for mural cells derived from IMR90C4- and CS03n2-derived NCSCs, although the IMR90C4 mural cells had weaker ZIC1 and ABCC9 signatures (FIG. 9F). Overall, the transcript profile of mural and pericyte-associated genes in the NCSC-derived mural cells was qualitatively very similar to that of primary human brain pericytes (FIG. 2E).

Figures 3A, 3B, 3C, 3D:
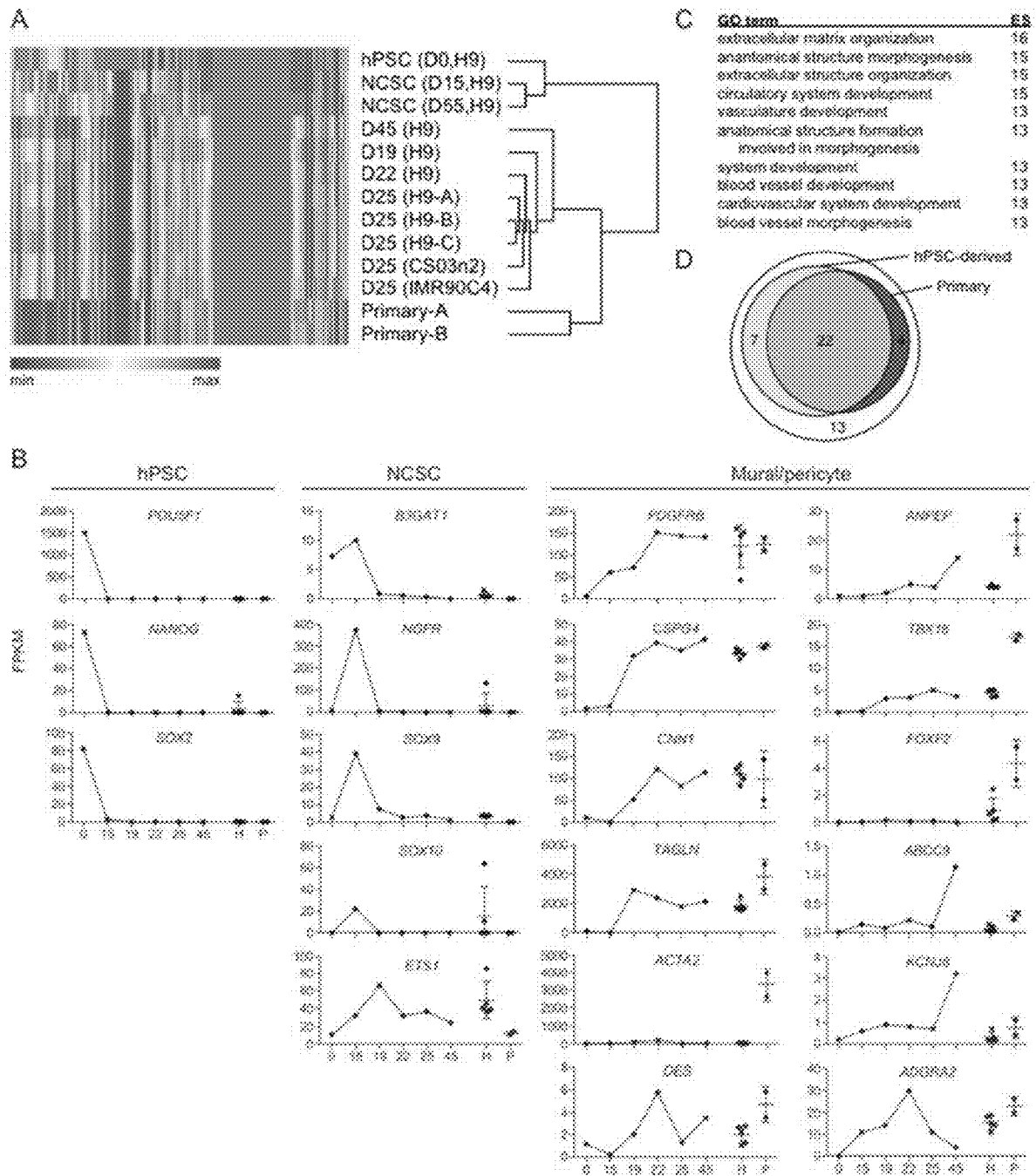
FIGS. 3A-3D. RNA-sequencing of pericyte-like cells and related cell types. A) Hierarchical clustering based on all transcripts of undifferentiated H9 hESCs, H9-derived NCSCs at D15 and after an additional 40 days in E6-CSFD (D55), H9-derived pericyte-like cells at D19, D22, and D25 (three independent differentiations at the D25 time point, indicated as "H9-A", "H9-B", and "H9-C"), H9-derived pericyte-like cells maintained for an additional 20 days in E6+10% FBS (D45), CS03n2- and IMR90C4-derived pericyte-like cells at D25, and primary brain pericytes (from two distinct cultures of the same cell source, indicated as "Primary-A" and "Primary-B"). B) Expression (FPKM) of selected transcripts in H9 hPSCs (day "0"), NCSCs ("15"), and during the differentiation of pericyte-like cells ("19", "22", "25", and "45"). Also shown is the mean transcript expression in all D25 hPSC-derived pericyte-like cells (H9 A-C, CS03n2 and IMR90C4, "H") and in primary brain pericytes ("P"). Error bars represent SEM of five independent differentiations ("H") or of two primary pericyte samples ("P"). C) Top 10 gene ontology (GO) terms, sorted by enrichment score (ES=−log$_{10}$(FDR)), for hPSC-derived pericyte-like cells. Genes included in the dataset were enriched in pericyte-like cells (average of all D25 samples) compared to NCSCs (average of D15 and D55 samples) (FPKM$_{pericyte-like\ cells}$/FPKM$_{NCSC}$ ≥10), and were expressed at ≥1 FPKM in pericyte-like cells. D) Expression (≥1 FPKM) of murine pericyte-enriched transcripts (46 transcripts (40)) in hPSC-derived pericyte-like cells (29 transcripts) and primary brain pericytes (26 transcripts). A detailed listing of genes and FPKM values can be found in Table 4.

We next used RNA-sequencing (RNA-seq) to quantify global gene expression in NCSC-derived mural cells and to evaluate the temporal emergence of a pericyte-like population. As expected, unbiased hierarchical clustering based on expression (fragments per kilobase of transcript per million mapped reads, FPKM) of all transcripts revealed the highest similarity between NCSC-derived mural cells generated from three independent differentiations from H9 hESCs as well as the two differentiations from IMR90C4 and CS03n2 iPSCs (FIG. 3A, D25 sample cluster). The Pearson correlation coefficients comparing transcript expression in H9-derived mural cells at D25 to the two replicate H9 differentiations were 0.99 and 0.98 (D25 H9-A versus D25 H9-B or H9-C, P<0.0001). Moreover, the Pearson correlation coefficients comparing the mural cells derived from the H9 hESC line to those derived from IMR90C4 and CS03n2 iPSCs were both 0.97 (D25 H9-A versus D25 IMR90 or CS03, P<0.0001). Collectively, these data indicate a highly reproducible differentiation procedure amongst replicated differentiations and hPSC lines. Furthermore, NCSC-derived mural cells at D25 clustered more closely with primary brain pericytes than with D15 NCSCs, D55 NCSCs that had been maintained in E6-CSFD following MACS, or hPSCs (FIG. 3A). The Pearson correlation coefficient between the average transcript expression of all D25 NCSC-derived mural cell samples and the average of the primary pericyte samples was 0.89 (P<0.0001), suggesting strong positive association between NCSC-derived mural cells and primary human pericytes. Consistent with RT-PCR experiments (FIG. 1D; FIG. 2E), temporal analysis of transcript expression demonstrated downregulation of pluripotency markers NANOG and POU5F1, and transient upregulation of NGFR, B3GAT1, SOX9, and SOX/0, as well as the cranial neural crest marker ETS1, in D15 NCSCs (FIG. 3B). We also observed gradual induction of CSPG4, PDGFRB, CNN1, TAGLN, ANPEP, TBX18, ABCC9, and KCNJ8 over the time course of E6+10% FBS treatment, and transient upregulation of ACTA2, DES, ADGRA2 (GPR124), and FOXF2 (FIG. 3B). Expression levels of CSPG4, PDGFRB, CNN1, TAGLN, FOXF2, ABCC9, KCNJ8, DES, and ADGRA2 were similar in NCSC-derived mural cells and primary brain pericytes; however, consistent with the lack of α-SMA expression (FIG. 2H; FIG. 8G,L), NCSC-derived mural cells expressed nearly 100-fold less ACTA2 transcript than primary pericytes (FIG. 3B). By D45, NCSC-derived mural cells retained expression of most markers at levels similar to D25 cells, while ANPEP, ABCC9, and KCNJ8 expression further increased, suggesting these cells may continue to mature during extended culture in E6+10% FBS (FIG. 3B). Comparison of transcripts upregulated in NCSC-derived mural cells compared to their NCSC precursors revealed several enriched Gene Ontology (GO) terms including vascular development, blood vessel morphogenesis, and extracellular matrix organization (FIG. 3C), indicating that differentiation is driving the progression from NCSCs to mural cells with vascular-associated transcript signatures. Of the 46 genes with human homologs identified as pericyte-enriched by single cell RNA-seq in mice (40), 29 were expressed at or above 1 FPKM by NCSC-derived mural cells and 26 by primary pericytes (FIG. 3D; Table 4). Finally, NCSCs maintained in E6-CSFD retained neural crest marker expression and did not develop expression of pericyte markers (FIG. 12). Collectively, these data demonstrate that differentiation of NCSCs in E6+10% FBS yielded a mural cell population that expressed pericyte-associated markers while closely mimicking primary brain pericytes at a transcriptome level. Thus, we refer to the NCSC-derived mural cells as brain pericyte-like cells throughout the remainder of the Example.

TABLE 4

Pericyte-enriched genes identified by single cell RNA-sequencing in mouse[39] with human homologs

| Gene | FPKM Primary | FPKM hPSC-derived* |
|---|---|---|
| ABCC9 | 0.3 | 0.1 |
| AGAP2 | 0.0 | 0.0 |
| ANK2 | 9.6 | 2.3 |
| ANO4 | 0.2 | 2.5 |
| APOD | 0.2 | 0.6 |
| APOE | 42.9 | 25.6 |
| ARHGAP31 | 3.4 | 7.6 |
| CORO1B | 68.4 | 56.1 |
| ECE1 | 58.7 | 31.0 |
| EMCN | 3.3 | 1.7 |
| FAM118B | 0.0 | 0.0 |
| FBLN1 | 24.7 | 112.0 |
| FLT1 | 4.7 | 7.6 |
| FOXF2 | 4.4 | 0.9 |
| GGT1 | 104.8 | 181.9 |
| GPR4 | 5.4 | 4.6 |
| IFI30 | 18.4 | 17.2 |
| IGF2 | 0.3 | 14.0 |
| ITIH5 | 2.6 | 0.2 |
| ITM2A | 0.3 | 3.9 |
| JUP | 6.4 | 20.8 |
| KCNJ8 | 0.8 | 0.3 |
| LGALS9 | 5.1 | 3.4 |
| NODAL | 0.1 | 0.1 |
| NRXN2 | 2.5 | 0.8 |
| NXPH4 | 30.3 | 0.4 |
| PCDHGC3 | 0.0 | 0.0 |
| PDE2A | 0.6 | 0.1 |
| PDE8A | 6.5 | 6.0 |
| PHC1 | 0.0 | 10.8 |
| PHLDB1 | 28.5 | 28.8 |
| PLOD1 | 189.1 | 145.8 |
| POR | 33.4 | 28.4 |
| PPP1CC | 40.7 | 82.8 |
| PREX2 | 0.0 | 0.0 |
| SEPP1 (SELENOP) | 19.8 | 1.4 |
| SFRP2 | 0.0 | 16.7 |
| SLC22A8 | 0.0 | 0.0 |
| SLC6A13 | 0.4 | 0.1 |
| SPP1 | 0.96 | 11.6 |
| ST8SIA4 | 0.0 | 0.3 |
| SYNE1.2 (SYNE1) | 16.9 | 6.0 |
| TNFRSF19 | 0.4 | 13.6 |
| TRPC3 | 0.2 | 0.1 |
| TTLL3 | 160.3 | 210.9 |
| UCHL1 | 739.1 | 415.9 |
| Number with FPKM ≥ 1 | 26 | 29 |

*Average of all D25 hPSC-derived pericyte-like cell differentiations (H9 A-C, CS03n2 and IMR90C4)

Brain Pericyte-Like Cells Assemble with Vascular Cord Networks

Pericytes associate with endothelial cells and stabilize nascent vascular networks (51). To assess the ability of brain pericyte-like cells to self-assemble with endothelial cells, an in vitro endothelial cord forming assay was performed. A 3:1 mixture of primary pericytes or hPSC-derived brain pericyte-like cells (D22) and human umbilical vein endothelial cells (HUVECs) or immortalized human BMECs (hBMECs) was plated on Matrigel (FIG. 4A; FIG. 13A). H9, CS03n2 and IMR90C4-derived brain pericyte-like cells self-associated with HUVECs and hBMECs much like primary human brain pericytes (FIG. 4B-C; FIG. 13B-C). After 24 hours, hPSC-derived pericyte-like cells exhibited high NG2 expression and aligned along the CD31+ endothelial cell cord perimeter and developed pericyte-like morphology with stellate-shaped bodies and extended cell processes (FIG. 4B-C). Whereas HUVECs or hBMECs alone and HUVECs or hBMECs in co-culture with control HEK293 cells yielded many small branching cords, co-culture with the hPSC-derived brain pericyte-like cells or primary human brain pericytes yielded fewer, appreciably longer cords (FIG. 4C-F; FIG. 13C-F). These data demonstrate that the hPSC-derived NCSC lineage mural cells exhibit pericyte-like association with endothelial cells leading to the formation of more well developed cord networks.

Brain Pericyte-Like Cells Induce Blood-Brain Barrier Properties

Figures 10A, 10B, 10C, 10D:
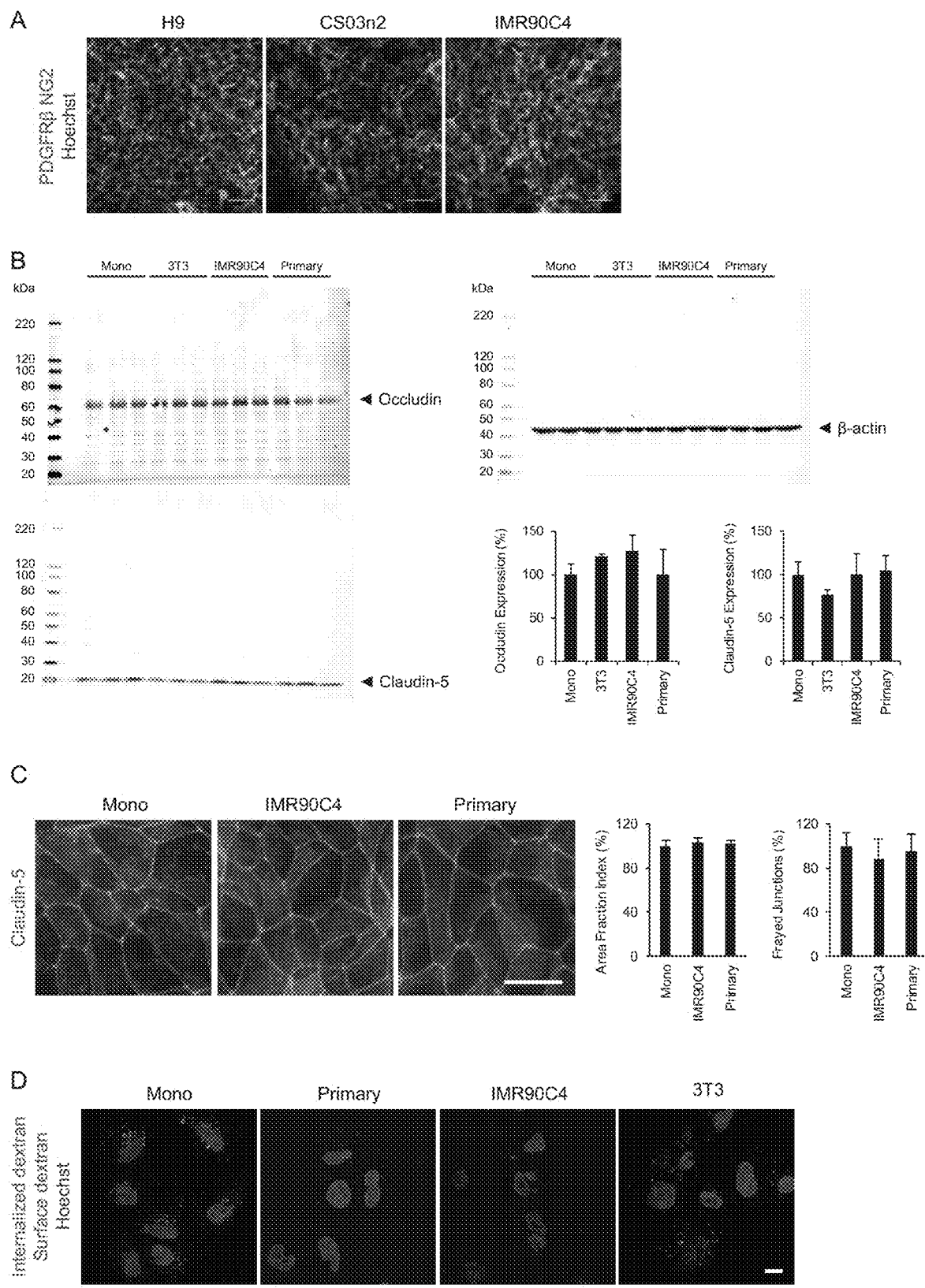
FIGS. 10A-10D. Supplemental analysis of BMEC/hPSC-derived pericyte-like cell co-cultures. A) PDGFRβ and NG2 immunocytochemistry of hPSC-derived pericyte-like cells following 48 hours of co-culture with iPSC-derived BMECs. Hoechst nuclear counter stain (blue) is also included. Images are representative of two independent differentiations. Scale bars: 100 µm. B) Western blot analysis of occludin and claudin-5 expression in iPSC-derived BMECs cultured alone or co-cultured with primary brain pericytes, MR90C4-derived pericyte-like cells, or 3T3s. Quantification of occludin and claudin-5 expression after normalized to β-actin signal and to monoculture expression levels. Plotted are the means ±SD from 3 Transwells from a single differentiation. No significant differences by ANOVA. C) Representative images of claudin-5 immunocytochemistry of BMECs cultured for 48 h in EC medium (Mono) or EC medium conditioned by primary brain pericytes or IMR90C4-derived pericyte-like cells. Scale bar: 25 µm. Quantification of claudin-5 area fraction index and frayed junctions. Plotted are the means ±SEM of 3 independent differentiations. No significant difference by ANOVA. D) Confocal microscopy of monocultured iPSC-derived BMECs incubated with Alexa 488-tagged 10 kDa dextran (green) with EC medium (Mono) or conditioned medium from primary brain pericytes, IMR90C4-derived pericyte-like cells, or 3T3s. Total dextran is depicted in green. Surface dextran was labeled with Alexa 647 (red), with little observed signal. Thus, the observed green signal is a result of internalized dextran. Hoechst nuclear counter stain (blue) is also included. Scale bar: 10 µm.

To investigate if hPSC-derived brain pericyte-like cells can recapitulate key BBB inducing properties that have been observed in vivo, such as reduction in tight junction abnormalities and transcytosis, we next co-cultured the pericyte-like cells with hPSC-derived BMECs generated as we previously described (56). When D22 brain pericyte-like cells were co-cultured with hPSC-derived BMECs, the BMEC barrier properties as measured by TEER were substantially elevated, while co-culture with a non-inducing cell type (3T3) yielded no barrier enhancement (FIG. 5A-B). TEER elevation by hPSC-derived brain-pericyte like cells was indistinguishable from that induced by primary human brain pericytes (FIG. 5B). The TEER increases were accompanied by a corresponding decrease in permeability to fluorescein, a hydrophilic, small molecule tracer (FIG. 5C). After BMEC co-culture, the brain pericyte-like cells remained NG2$^+$/PDGFRI3$^+$ (FIG. 10A), indicating their continued maintenance of mural identity. To determine tight junction changes that may drive the induction in BMEC barrier properties, the expression level and localization of tight junction proteins occludin and claudin-5 were evaluated in the BMECs. Expression levels of occludin and claudin-5 were unchanged by co-culture (FIG. 10B). In addition, quantitative immunocytochemical evaluation of occludin and claudin-5 indicated that the number of cells possessing continuous tight junctions was unchanged upon treatment with pericyte-conditioned medium (FIG. 5D-E; FIG. 10C). However, the percentage of cells with occludin tight junction abnormalities or fraying was substantially reduced by treatment with pericyte-conditioned medium (FIG. 5F), correlating with the reduced permeability, while claudin-5 fraying remained unchanged (FIG. 10C).

Next, the effects of brain pericyte-like cell co-culture on BMEC transcytosis properties were evaluated. To test non-specific molecular uptake and transcytosis in BMECs, a 10 kDa Alexa 488-tagged dextran was dosed into the apical Transwell chamber and accumulation into and transcytosis across the BMEC monolayer were quantified. After BMEC culture with medium conditioned by hPSC-derived brain pericyte-like cells, confocal imaging indicated a qualitative decrease in intracellular dextran uptake in punctate vesicular structures, similar to that observed with primary human brain pericytes; whereas, medium conditioned by 3T3 control cells had no effect (FIG. 10D). Indeed, quantification of dextran accumulation in BMECs co-cultured with brain pericyte-like cells or primary brain pericytes indicated that BMEC accumulation was reduced by about 30% (FIG. 5G). These differences in accumulation translated to a corresponding 30% decrease in 10 kDa dextran transcytosis upon pericyte co-culture (FIG. 5H). In contrast, when 10 kDa dextran transport was measured at 4° C., conditions that significantly inhibit vesicular transcytosis processes, pericyte co-culture did not affect dextran transport compared to 3T3s or hPSC-derived BMEC monoculture (FIG. 5I), indicating that the observed decreases in dextran transport could not be ascribed to differences in paracellular transport resulting from improved tight junction fidelity.

Figures 6A, 6B, 6C:
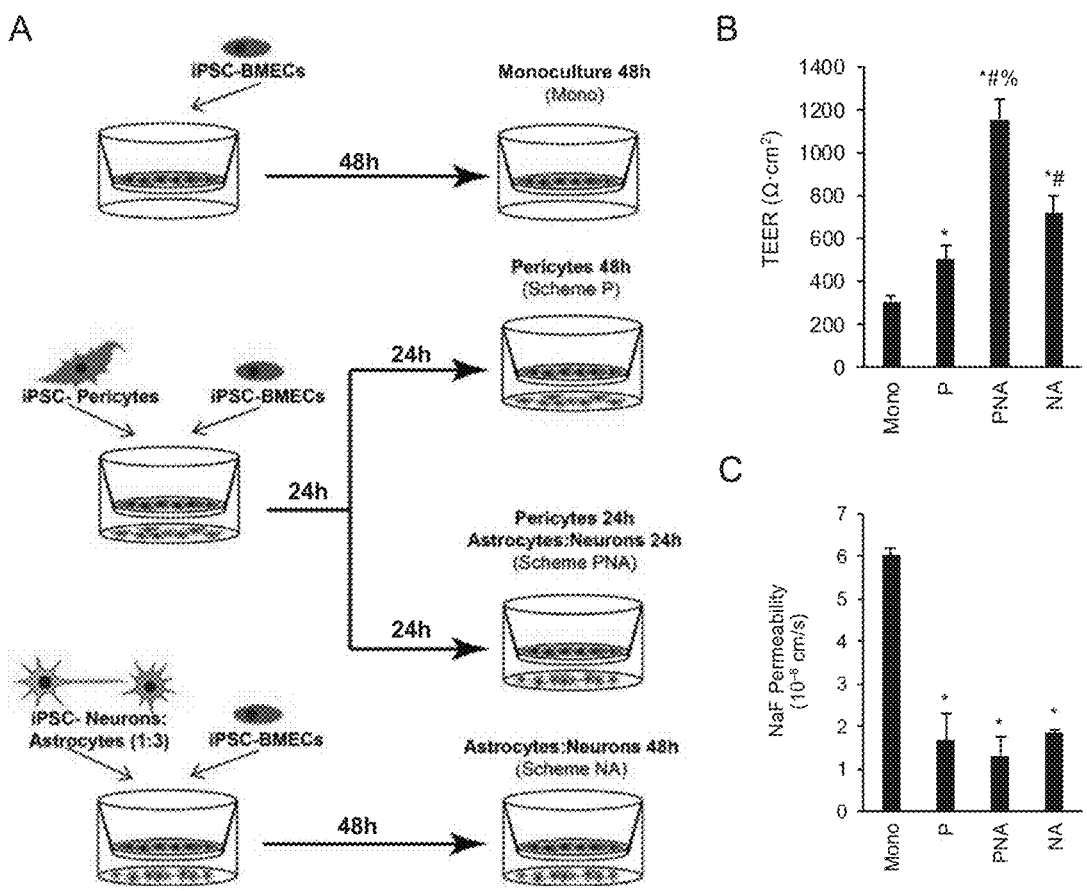
FIGS. 6A-6C.
Figure 11A:
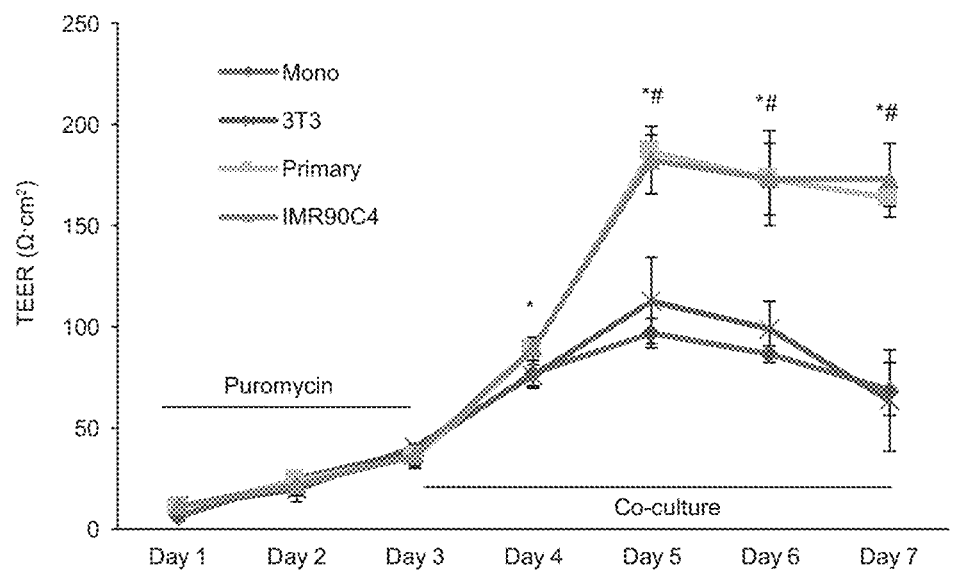
FIGS. 11A-11C. Measurement of the effects of hPSC-derived pericyte-like cells on primary rat BMEC phenotypes. A) TEER profile of primary rat BMECs either in monoculture or co-culture with primary brain pericytes, IMR90C4-derived pericyte-like cells, or 3T3s. Plotted are means ±SD of three Transwells from a single rat BMEC isolation. *P<0.05 IMR90C4-derived pericyte-like cell co-culture vs. monoculture; # P<0.05 primary pericyte co-culture vs. monoculture; ANOVA followed by Dunnett's test. B,C) Accumulation (B) or transcytosis (C) of Alexa 488-tagged 10 kDa dextran in primary rat BMECs following co-culture with cell types as described in A. All results normalized to BMEC monoculture control. Plotted are the means ±SD of 3 Transwells from a single rat BMEC isolation. *P<0.05 vs. monoculture; ANOVA followed by Dunnett's test.
Figure 11B:
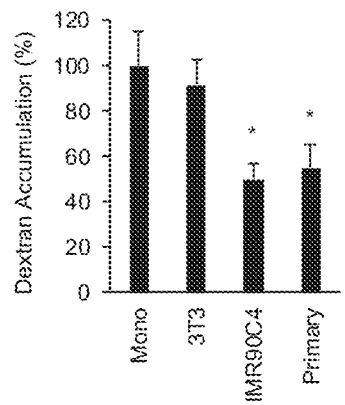
Figure 11C:
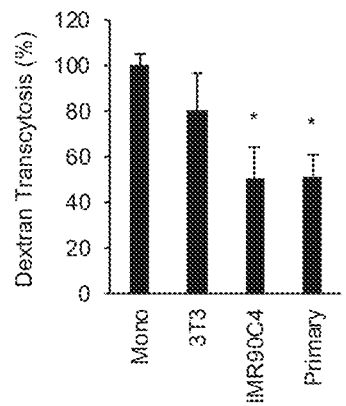

Finally, to confirm that the effects of hPSC-derived brain pericyte-like cells are not specific to BMECs derived from hPSCs, the induction of BBB barrier and transcytosis attributes was also evaluated in primary rat BMECs. Co-culture with IMR90C4-derived brain pericyte-like cells elevated the TEER in primary rat BMECs to the same level as observed with primary human brain pericytes (FIG. 11A). In addition, co-culture with brain pericyte-like cells also reduced accumulation and transcytosis of 10 kDa dextran in primary rat BMECs (FIG. 11B,C). In summary, these data indicate that hPSC-derived brain pericyte-like cells can induce BBB phenotypes including elevation of BMEC barrier tightness and reduction in transcytosis.

iPSC-Derived Brain Pericyte-Like Cells can be Integrated into an Isogenic NVU Model Previously, we demonstrated that sequential co-culture of iPSC-derived BMECs with primary pericytes and primary neural progenitor-derived astrocytes and neurons enhanced BMEC barrier tightness (30). Subsequently, iPSC-derived astrocytes and neurons were shown to induce barrier formation in iPSC-derived BMECs (34). Here, iPSC-derived brain pericyte-like cells were combined with iPSC-derived BMECs, astrocytes, and neurons to model the NVU. IMR90C4-derived BMECs were sequentially co-cultured with IMR90C4-derived brain pericyte-like cells and IMR90C4-derived astrocyte/neuron cultures (PNA) and compared to IMR90C4-derived BMEC monocultures or IMR90C4-derived BMECs co-cultured with pericytes (P) or astrocytes/neurons (NA) alone (FIG. 6A). All three co-culture conditions (P, NA, and PNA) significantly elevated TEER above monoculture (FIG. 6B). While neuron/astrocyte co-culture slightly elevated TEER above pericyte co-culture (720±84 $\Omega \cdot cm^2$ NA co-culture vs. 503±63 $\Omega \cdot cm^2$ P co-culture), the combination of pericyte and neuron/astrocyte co-culture treatments further elevated BMEC TEER (1156±94 $\Omega \cdot cm^2$ vs. NA and P co-culture) (FIG. 6B). All three co-culture conditions yielded a five-fold reduction in sodium fluorescein permeability compared to monoculture conditions but no appreciable differences were observed between separate co-culture treatment conditions (FIG. 6C), as has been reported previously for BMEC monolayers with TEER values exceeding 500-600 $\Omega \cdot cm^2$ (30, 34, 57). These data demonstrate that iPSC-derived brain pericyte-like cells can be readily combined with iPSC-derived BMECs, astrocytes and neurons to form an isogenic model of the human NVU.

Brain pericytes play essential roles in BBB formation and maintenance by regulating BMEC transcytosis, barrier fidelity, vascular structure and stability (5, 13, 14, 19-21). Here we report that mural cells can be differentiated from hPSC-derived NCSCs, and that these cells develop brain pericyte-like attributes. The brain pericyte-like cells can self-assemble with endothelial cells in vitro and impact their vascular network structure. Moreover, the brain pericyte-like cells induce BBB properties, including barrier tightening and reduction of transcytosis in BMECs. Finally, these cells can be incorporated into an isogenic iPSC-derived NVU model, with potential applications in patient-specific NVU modeling.

During embryonic development, NCSCs are first specified at the interface between the neural plate and non-neural ectoderm, and subsequently reside in the dorsal neural tube before migrating throughout the embryo and differentiating to diverse cell types (58). Previous NCSC differentiation protocols have relied on differentiating hPSCs to neuroectoderm and subsequently isolating NCSC subpopulations (41, 47), or have used a directed WNT activation and activin/nodal inhibition approach to obtain NCSCs (46, 59, 60). We chose to utilize the latter approach given its simplicity and potential for highly enriched NCSC populations. BMP signaling activation was previously shown to inhibit NCSC formation (46); however, the need to inhibit BMP signaling during NCSC differentiation has been variable (42, 46). Here, when the differentiation strategy was adapted to minimal E6 medium, inhibition of BMP signaling was necessary to efficiently direct hPSCs to p75-NGFR+/HNK1+ NCSCs. The NCSCs differentiated in E6-CSFD medium were a highly enriched population of multipotent cells having the capacity to form mesenchymal derivatives and peripheral neurons using multiple hPSC lines.

A common approach to differentiate mural cells from NCSCs is to supplement basal medium with PDGF-BB and TGFβ1 (41, 42, 47). Resultant cells have been shown to express calponin, SM22α, and α-SMA (41, 42, 47), but two key mural cell markers, PDGFRβ and NG2 were not previously examined. While differentiation of NCSCs in E6 medium yielded PDGFRβ+ cells, neither E6 medium nor E6 medium supplemented with PDGF-BB and TGFβ 1 generated cells expressing NG2. However, both calponin and SM22α were expressed even in the absence of growth factor supplementation. Instead, when E6 was supplemented with 10% FBS, the differentiating cells acquired NG2 and PDGFRβ expression, and thus were classified as forebrain lineage mural cells (40, 49). Recent work demonstrated pericyte differentiation from hPSC-derived cranial neural crest cells using PDGF-BB, however 2-5% FBS was included in the differentiation medium (37). Thus, it is possible that the observed pericyte differentiation is mediated at least partially by FBS, consistent with our observations. Alternatively, the requirement of PDGF-BB may reflect differences in initial neural crest phenotypes or basal media. While others have suggested the use of serum to drive mural cell differentiation from NCSC (46, 47), these studies generated cells that were smooth muscle actin positive. In contrast, we did not observe substantial α-SMA expression in the differentiated mural cells, even after extended culture. Brain pericytes lining higher order capillaries generally do not express α-SMA in vivo (40, 61, 62), although very recent evidence suggests that higher order pericytes may actually express low levels of α-SMA that are lost upon sample preparation (63). In addition, it is well known that upon fresh isolation, primary brain pericytes express α-SMA in 5-10% of cells, whereas after a few days in culture they become nearly uniformly α-SMA+ (38, 39), as also observed here with primary human brain pericytes, which expressed α-SMA. Thus, the lack of α-SMA expression in the differentiated brain pericyte-like cells better reflects the lack of α-SMA in brain pericytes in vivo. However, much like primary brain pericytes and previous reports with NCSC derived mural cells, we observed sustained expression of the contractile-related proteins calponin and SM22α. In addition, differentiation of mesenchymoangioblasts towards pericyte lineages yielded cells that expressed differential levels of calponin (64). Although SM22α is an early developmental marker of mural cells (65), a recent single cell transcriptomics study strongly suggests that murine brain capillary pericytes in vivo do not express calponin-encoding Cnn1 or SM22α-encoding Tagln (40). Additional transcript evaluation confirmed the brain signature of the pericyte-like cells (ZIC1, FOXF2) (54, 55). The brain pericyte-like cells also expressed transcripts for ABCC9 and KCNJ8, two additional markers that differentiate brain capillary pericytes from other mural cell types (40, 49), and these markers were further elevated over extended culture times. RNA-sequencing also indicated a transcriptome-wide similarity to primary human brain pericytes and expression of many genes identified as pericyte-enriched by single cell RNA-sequencing in mouse (40). Taken together, the hPSC-derived brain-pericyte like cells had marker profiles that suggested the generation of cells similar to brain pericytes.

While the marker expression suggested that the differentiation process generated brain pericyte-like cells, it is most important that the cells recapitulate key functional attributes of brain pericytes. When cultured with HUVECs or hBMECs, brain pericyte-like cells aligned along vascular cords and extended cell processes. Primary pericytes can stabilize endothelial cell cord formation in vitro (26). This phenotype was also observed with both primary human brain pericytes and hPSC-derived brain pericyte-like cell co-culture as indicated by reduced numbers of longer cords as has also been reported using hPSC-derived pericytes of mesenchymal origins (64). In addition to this more general pericyte phenotype, it was expected that a brain pericyte-like cell would impact the barrier and non-specific transcytosis properties of brain endothelial cells (13, 14). Indeed, BBB properties of both hPSC-derived BMECs and primary rat BMECs were substantially induced by co-culture with hPSC-derived brain pericyte-like cells, and these effects mimicked those induced by primary human brain pericytes. TEER was increased substantially as expected (13, 30). Correlating with this increased barrier function, pericyte co-culture decreased the number of frayed occludin tight junctions as seen previously for a variety of barrier inductive stimuli (29, 34, 66), but did not alter the expression levels of tight junction proteins occludin or claudin-5. These results mirror those in vivo where tight junction structure was altered by pericytes although the expression levels of tight junction proteins were not affected (13). We also demonstrated that non-specific cellular accumulation and transcytosis were downregulated in BMECs after co-culture with brain-pericyte like cells, and the effects were indistinguishable from those elicited by primary human brain pericytes. These phenotypes combined with the developmental origins and marker expression profile, along with the similarities to primary human brain pericytes, suggest that we have generated a novel hPSC-derived cell that can model human brain pericytes.

While many studies have utilized primary brain pericytes to enhance BMEC barrier properties, primary brain pericytes offer limited scalability, especially for human in vitro BBB models (28, 30, 67). In addition, limited primary cell availability essentially eliminates the possibility of using patient matched brain pericytes and BMECs that could be used for disease modeling applications. Here, we demonstrate the capability to differentiate brain like pericytes in a scalable fashion (~1000 brain pericyte-like cells per input stem cell). Moreover, the differentiation is reproducible amongst differentiations and across hPSC lines. Thus, the ability to derive brain pericyte-like cells from patient-derived iPSCs provides a unique tool for the study of patient-specific pericyte contributions to CNS disorders that have been suggested to have pericyte involvement such as stroke, epilepsy, demyelinating disease, and Alzheimer's disease (7, 10, 68-71). In addition, lineage-specific differences have been noted in hPSC-derived pericytes, motivating the use of pericytes from appropriate developmental origins for disease modeling applications (41). The brain pericyte-like cells can also be used in multicellular NVU models to capture the cellular crosstalk that is likely responsible for many disease processes at the BBB. To this end, we have demonstrated that it is possible to generate BMECs, neurons, astrocytes, and brain pericyte-like cells from a single iPSC cell line and combine them to form an isogenic NVU model having optimal TEER. These findings followed similar trends to our earlier reports where iPSC-derived BMEC properties were enhanced by co-culture with brain pericytes and neural progenitor cell-derived astrocytes and neurons from primary sources. We note, however, that this Transwell-based model lacks the potentially important contributions of cell-cell contact and fluid shear stress, motivating future efforts to integrate hPSC-derived NVU cell types into microfluidic or cell aggregate-based in vitro models (72, 73). It is likely that these multicellular NVU models will be used to uncover new mechanisms of BBB regulation in health and disease and assist in the therapeutic development process for CNS disorders.

Materials and Methods hPSC Maintenance

IMR90C4 and CS03n2 iPSCs and H9 hESCs were maintained on Matrigel coated plates in E8 medium, which is DMEM/F12 basal medium supplemented with L-ascorbic acid-2-phosphate magnesium (64 mg/L), sodium selenium (14 µg/L), FGF2 (100 µg/L), insulin (19.4 mg/L), NaHCO$_3$ (543 mg/L), transferrin (10.7 mg/L), and TGFβ1 (2 µg/L) and prepared according to Chen et al. (74). When cells reached ~70% confluence, cells were passaged using Versene to new Matrigel coated plates. For hPSCs used in BMEC differentiations, cells were maintained in mTeSR1 on Matrigel plates and passaged as previously described (75).

NCSC Differentiation

One day prior to initiating NCSC differentiation, hPSCs maintained in E8 medium were singularized using Accutase and seeded at $9.1 \times 10^4$ cells/cm$^2$ onto Matrigel coated plates with E8+10 µM Y27632. NCSC differentiation was initiated the next day by switching medium to E6, which is DMEM/F12 basal medium supplemented with L-ascorbic acid-2-phosphate magnesium (64 mg/L), sodium selenium (14 µg/L), insulin (19.4 mg/L), NaHCO$_3$ (543 mg/L), and transferrin (10.7 mg/L). E6 was supplemented with 22.5 mg/L heparin sodium salt from porcine mucosa to stabilize FGF2, 1 µM CHIR99021, 10 µM SB431542 (Tocris), 10 µg/L FGF2, and 1 µM dorsomorphin, hereafter labeled E6-CSFD. Cells were expanded by replacing E6-CSFD daily and passaging cells every time cells reached 100% confluence to fresh Matrigel coated plates. During passaging, cells were singularized using Accutase and replated at a splitting density of one 6-well to 6 new 6-wells in E6-CSFD medium. Cells were generally passaged without 10 µM Y27632. However, to increase IMR90C4 cell line survival during first passaging following NCSC differentiation initiation, IMR90C4 cells were replated in E6-CSFD+10 µM Y27632. Subsequent IMR90C4 NCSC expansion passages were replated without Y27632. Cells were typically passaged 2-3 days following NCSC differentiation initiation and subsequently passaged every 3-6 days depending on cell growth kinetics.

Magnetic Activated Cell Sorting of NCSCs

At D15 of E6-CSFD treatment, cells were dissociated using Accutase and labeled with 20 µL/10$^7$ cells NCSC microbeads (Miltenyi), 20 µL/10$^7$ cells FcR blocking reagent, and 60 µL/10$^7$ MACS buffer (0.5% BSA+2 mM EDTA in sterile PBS without Ca$^{2+}$/Mg$^{2+}$) at 4° C. for 15 minutes. Cells were washed in MACS buffer and resuspended in 500 µL MACS buffer/$2 \times 10^7$ cells. Cells were sorted through two LS columns (Miltenyi) according to manufacturer instructions and resuspended in E6-CSFD+10 µM Y27632 to appropriate density for specific NCSC lineage differentiations as described below.

NCSC Lineage Differentiations

For differentiation of peripheral neurons, after MACS sorting, hPSC-derived NCSCs were replated on Matrigel-coated plates and expanded for 14 days in E6-CSFD. These cells were replated on Matrigel-coated 12-well plates at $5 \times 10^4$ cells/cm$^2$ in E6-CSFD. The following day, the medium was switched to peripheral neuron medium composed of DMEM/F12, 1×N2 supplement, 10 ng/ml BDNF, 10 ng/ml GDNF, 10 ng/ml NT-3, 10 ng/ml NGF-β, 200 µM ascorbic acid (AA), and 0.5 mM cAMP, and replaced every 2 days for 2 weeks.

For differentiation of mesenchymal derivatives, after MACS sorting, hPSC-derived NCSCs were replated on noncoated polystyrene plates and expanded for 11 days in E6-CSFD. For adipogenesis, expanded hPSC-derived NCSCs were seeded at a density of 10,000 cells/cm$^2$ and treated with adipogenic medium composed of high-glucose DMEM, 10% FBS, 1% antibiotics, 1 µg/ml insulin, 0.5 mM 3-isobutyl-1-methylxanthine (IBMX), and 1 µM dexamethasone (Sigma-Aldrich). For osteogenesis, the seeding density was 5,000 cells/cm$^2$ and the cells were treated with osteogenic medium consisting of low-glucose DMEM, 10% FBS, 1% antibiotics, 50 µg/ml AA, 10 mM β-glycerophosphate, and 0.1 µM dexamethasone. For chondrogenesis, 250,000 NCSC were collected to form a high cell density pellet by centrifuged at 600 g for 5 minutes and treated with chondrogenic medium containing high-glucose DMEM, 1% antibiotics and ITS Premix (BD Bioscience), 40 µg/ml L-proline, 50 µg/ml AA, 0.9 mM sodium pyruvate (Sigma-Aldrich), 0.1 µM dexamethasone, and 10 ng/ml of freshly added transforming growth factor β1 (TGFβ1) (Peprotech). Medium was changed every 3 days for all three differentiation procedures.

To analyze adipogenic differentiation, cells were fixed in 4% of formaldehyde and stained with Oil Red O (Sigma-Aldrich) for lipid droplet formation. To analyze osteogenic differentiation, cells were fixed in 60% isopropanol and stained with Alizarin Red (Rowley Biochemical, Danvers, Mass., USA) to evaluate mineral deposition. Chondrogenic potential was assessed by Alcian blue staining. Cell pellets were first fixed in 4% formaldehyde for 2 hours. Next, the cell pellet was dehydrated by a series of increasing concentration of ethanol, infiltrated with xylene, and then embedded with paraffin. Embedded cell pellets were cut into 8 µm sections using a microtome and stained with Alcian blue (Polysciences, Warrington, Pa., USA) to determine the glycosaminoglycan (GAG) content.

Pericyte Differentiation Factor Identification

Following MACS sorting, NCSC were replated onto 48-well plates in E6-CSFD medium+10 µM Y27632. Cells were switched to mural cell differentiation medium the next day, expanded for six days, and stained for NG2/PDGFRβ expression. Cells were expanded on uncoated plates in E6 medium, E6 medium supplemented with 2 ng/mL TGFβ1+

20 ng/mL PDGF-BB, or E6 medium supplemented with 10% fetal bovine serum (FBS). Cells were also expanded in E6 supplemented with 10% FBS on gelatin-coated plates prepared by coating plates for at least 1 h at 37° C. with a 0.1% gelatin A solution dissolved in water.

Immunocytochemistry

Cells were fixed fifteen minutes at room temperature with either 4% paraformaldehyde (PFA) or 100% ice-cold methanol depending on antibody staining conditions. Cells were rinsed three times in PBS without $Ca^{2+}/Mg^{2+}$ and stored at 4° C. in PBS until ready to stain. After aspirating PBS, cells were blocked one hour in blocking buffer at room temperature and incubated overnight at 4° C. on a rocking platform with primary antibodies diluted in primary antibody staining buffer.

Antibodies and staining conditions are listed in Table 2. The following day, cells were washed three times with PBS and incubated with secondary antibodies diluted 1:200 in primary antibody staining buffer. Cells were probed one hour in the dark at room temperature on a rocking platform. Afterwards, secondary antibody staining buffer was aspirated, and cells were incubated five minutes with 4 μM Hoechst 33342 diluted in PBS. Cells were washed three times with PBS and stored at 4° C. in PBS in the dark until ready to image. Images were taken on Olympus epifluorescence and Nikon A1R-Si+ confocal microscopes.

were subsequently incubated in 100 μL primary antibody staining buffer with 1:500 Alexa-tagged isotype-specific goat secondary antibodies. Cells were washed as previously described and resuspended in 4% PFA for 15 minutes at room temperature. Cells were subsequently stored in wash buffer for up to 24 hours at 4° C. prior to running samples on cytometer.

Temporal RNA Analysis

Cells were harvested using Accutase, quenched in DMEM/F12, and spun down 5 minutes at 200 g. After removing the supernatant, cell pellets were snap frozen at −80° C. until ready for mRNA extraction. The RNeasy Mini Kit (Qiagen) was used to extract mRNA, including a cell lysate homogenization step on QIAshredder Columns (Qiagen), according to manufacturer instructions. DNA was removed on column using the RNase-free DNase Set (Qiagen). Extracted RNA was stored in nuclease-free water at −20° C. until ready to reverse transcribe to cDNA. RNA was reverse transcribed at a concentration of 250 ng/mL into cDNA using Omniscript reverse transcriptase kit (Qiagen) and Oligo(dT)$_{20}$ Primers (Life Technologies). Temporal gene expression analysis was conducted using 25 μL PCR reactions containing GoTaq Green Master Mix (Promega), 10 ng/reaction cDNA template, and 100 nM forward/reverse primers. PCR was run according to manufacturer protocols,

TABLE 2

Antibody Staining Conditions
Table 2: Antibody Staining Conditions

| Marker | Fixative | App. | Vendor (Clone/Catalog #, Species) | Dilution | Blocking Buffer | Staining Buffer |
|---|---|---|---|---|---|---|
| p75-NGFR | 4% PFA | ICC | Advanced Targeting Systems (ME20.4, Mouse IgG$_1$) | 1:1000 | 1% BSA | 1% BSA |
|  |  | Flow | Advanced Targeting Systems (ME20.4, Mouse IgG$_1$) | 0.2 μL/10$^6$ cells | N/A | PBS |
| HNK1 | 4% PFA | ICC | Sigma (C6608, Mouse IgM) | 1:300 | 1% BSA | 1% BSA |
|  |  | Flow | Sigma (C6608, Mouse IgM) | 0.2 μL/10$^6$ cells | N/A | PBS |
| AP2 | 4% PFA | ICC | DSHB (3B5, Mouse IgG$_{2B}$) | 1:50 | 1% BSA + 0.1% TX-100 | 1% BSA |
| Peripherin | 4% PFA | ICC | Millipore (AB1530, Rabbit Polyclonal) | 1:200 | 1% BSA + 0.1% TX-100 | 1% BSA |
| βIII-Tubulin | 4% PFA | ICC | Sigma (T8860, Mouse IgG$_{2b}$) | 1:500 | 1% BSA + 0.1% TX-100 | 1% BSA |
| NG2 | 4% PFA | ICC | Millipore (MAB2029, Mouse IgG$_{2a}$) | 1:100 | 5% goat serum + 0.4% TX-100 | PBS + 0.4% TX-100 |
|  |  | Flow | Millipore (MAB2029, Mouse IgG$_{2a}$) | 2 μL/10$^6$ cells | N/A | MACS Buffer |
| PDGFRβ | 4% PFA | ICC | Cell Signaling Technology (28E1, Rabbit Monoclonal) | 1:100 | 5% goat serum + 0.4% TX-100 | PBS + 0.4% TX-100 |
|  |  | Flow | BD Biosciences (28D4, Mouse IgG$_{2a}$) | 1.25 μL/10$^6$ cells | N/A | MACS Buffer |
| CNN1 | 4% PFA | ICC | Sigma (C2687, Mouse IgG$_1$) | 1:15000 | 3% BSA + 0.1% TX-100 | 3% BSA |
| SM22α | 4% PFA | ICC | Abcam (ab14106) | 1:1000 | 3% BSA + 0.1% TX-100 | 3% BSA |
| CD31 | 4% PFA | ICC | Thermo Fisher (RB-10333, Rabbit Polyclonal) | 1:25 | 5% goat serum + 0.4% TX-100 | PBS + 0.4% TX-100 |
| aSMA | 4% PFA | ICC | Lab Vision (MS-113-P) | 1:100 | 5% milk + 0.1% TX-100 | 5% milk |
| β-actin | N/A | WB | Cell Signaling Technology (13E5, Rabbit Monoclonal) | 1:1000 | TBST + 5% milk | TBST + 5% milk |
| Occludin | MeOH | ICC | Invitrogen (OC-3F10, Mouse IgG$_1$) | 1:200 | 10% goat serum | 10% goat serum |
|  | N/A | WB | Invitrogen (OC-3F10, Mouse IgG$_1$) | 1:500 | TBST + 5% milk | TBST + 5% milk |
| Claudin-5 | N/A | WB | Invitrogen (4C3C2, Mouse IgG$_1$) | 1:250 | TBST + 5% milk | TBST + 5% milk |
| CD13 | 4% PFA | ICC | R&D Systems (MAB3815, Mouse IgG$_{2a}$) | 1:50 | 10% goat serum | 10% goat serum |
| Desmin | MeOH | ICC | Thermo Fisher (RB-9014, Rabbit Polyclonal) | 1:50 | 10% goat serum | 10% goat serum |

Flow Cytometry

Cells were incubated 30 minutes on ice with primary antibody diluted in 100 μL/sample primary antibody staining buffer as indicated in Table 2. Cells were washed one time with cold PBS (p75-NGFR/HNK1 flow cytometry) or MACS buffer (NG2 and PDGFRβ flow cytometry). Cells and all reactions included a no template and mRNA control to verify no genomic DNA contamination or amplification. PCR primer sequences, annealing temperatures, and cycle times are listed in Table 3. PCR products were resolved on a 2% agarose gel, stained using ethidium bromide, and imaged on a ChemiDoc XRS+ System (Bio-Rad).

TABLE 3

DNA Probe Sequences and Running Conditions

| Gene | T$_a$ (° C.) | Cycles | Fwd Sequence | Rev Sequence |
|---|---|---|---|---|
| ABCC9 | 60 | 40 | 5'-TCA ACC TGG TCC CTC ATG TCT-3' (SEQ ID NO: 1) | 5'-CAG GAG AGC GAA TGT AAG AAT CC-3' (SEQ ID NO: 2) |
| ACTA2 | 60 | 30 | 5'-TGT TCC AGC CAT CCT TCA TC-3' (SEQ ID NO: 3) | 5'-GCA ATG CCA GGG TAC ATA GT-3' (SEQ ID NO: 4) |
| ANPEP | 49 | 40 | 5'-GAA GAG AAC TGG AGG AAG ATT CAG-3' (SEQ ID NO: 5) | 5'-CCA GGT TGA AGG CGT CAT TA-3' (SEQ ID NO: 6) |
| B3GAT1 | 58 | 35 | 5'-TCG CCT GGA CTG GAC TGG GG-3' (SEQ ID NO: 7) | 5'-TGG CCT TGG CCT CCC TCC TC-3' (SEQ ID NO: 8) |
| CNN1 | 53 | 40 | 5'-GTC CAC CCT GGC TTT-3' (SEQ ID NO: 9) | 5'-AAA CTT GTT GGT GCC CAT CT-3' (SEQ ID NO: 10) |
| CSPG4 | 54 | 35 | IDT DNA Hs.PT.58.39417158 Predesigned Probe | |
| FOXF2 | 52 | 40 | 5'-ACC AGA GCG TCT GTC AGG ATA TT-3' (SEQ ID NO: 11) | 5'-GTG ACT TGA ATC CGT CCC AGT TTC-3' (SEQ ID NO: 12) |
| GAPDH | 60 | 30 | 5-GAA GGT GAA GGT CGG AGT CAA CG-3' (SEQ ID NO: 13) | 5'-TCC TGG AAG ATG GTG ATG GGA T-3' (SEQ ID NO: 14) |
| KCNJ8 | 60 | 40 | 5'-GTG ATT GCC GTC CGA AAT GG-3' (SEQ ID NO: 15) | 5'-AGT TGG TGA ATA GGA ACC ACC T-3' (SEQ ID NO: 16) |
| NANOG | 58 | 30 | 5'-CGA AGA ATA GCA ATG GTG TGA CG-3' (SEQ ID NO: 17) | 5'-TTC CAA AGC AGC CTC CAA GT-3' (SEQ ID NO: 18) |
| NGFR | 60 | 30 | 5'-GTG GGA CAG AGT CTG GGT GT-3' (SEQ ID NO: 19) | 5'-AAG GAG GGG AGG TGA TAG GA-3' (SEQ ID NO: 20) |
| PDGFRB | 53 | 40 | 5'-GCT CAC CAT CAT CTC CCT TAT C-3' (SEQ ID NO: 21) | 5'-CTC ACA GAC TCA ATC ACC TTC C-3' (SEQ ID NO: 22) |
| POU5F1 | 58 | 30 | 5'-CAG TGC CCG AAA CCC ACA C-3' (SEQ ID NO: 23) | 5'-GGA GAC CCA GCA GCC TCA AA-3' (SEQ ID NO: 24) |
| SOX10 | 61 | 40 | 5'-ATA CGA CAC TGT CCC GGC CCT AAA-3' (SEQ ID NO: 25) | 5'-TTC TCC TCT GTC CAG CCT GTT CTC-3' (SEQ ID NO: 26) |
| SOX9 | 60 | 40 | 5'-AGC GAA CGC AACA TCA AGA C-3' (SEQ ID NO: 27) | 5'-CTG TAG GCG ATC TGT TGG GG-3' (SEQ ID NO: 28) |
| TAGLN | 51 | 40 | 5'-TCT TTG AAG GCA AAG ACA TGG-3' (SEQ ID NO: 29) | 5'-TTA TGC TCC TGC GCT TTC TT-3' (SEQ ID NO: 30) |
| TBX18 | 60 | 40 | 5'-CCC AGG ACT CCC TCC TAT GT-3' (SEQ ID NO: 31) | 5'-TAG GAA CCC TGA TGG GTC TG-3' (SEQ ID NO: 32) |
| TFAP2A | 50 | 30 | 5'-TCC CTG TCC AAG TCC AAC AGC AAT-3' (SEQ ID NO: 33) | 5'-AAA TTC GGT TTC GCA CAC GTA CCC-3' (SEQ ID NO: 34) |
| ZIC1 | 59 | 40 | 5'-TGG CCC GGA GCA GAG TAA T-3 (SEQ ID NO: 35) | 5'-CCC TGT GTG CGT CCT TTT G-3' (SEQ ID NO: 36) |

RNA-Sequencing

RNA was extracted from H9 hESCs, H9-derived NCSCs at D15, H9-derived NCSCs maintained for 40 additional days in E6-CSFD (D55), H9-derived pericyte-like cells at D19, D22, and D25 (three independent differentiations at the D25 time point), H9-derived pericyte-like cells maintained for 20 additional days in E6+10% FBS (D45), CS03n2-derived pericyte-like cells at D25, IMR90C4-derived pericyte-like cells at D25, and primary brain pericytes using the RNeasy Mini Kit (Qiagen) as described above. TruSeq stranded mRNA libraries were prepared, cDNA synthesized, pooled, and distributed over two sequencing lanes for samples sequenced on an Illumina HiSeq 2500 by the University of Wisconsin-Madison Biotechnology Center. Reads were mapped to the human genome (hg38) with HISAT2 (v2.1.0) and transcript abundances (fragments per kilobase of transcript per million mapped reads, FPKM) quantified with Cufflinks (v2.1.1). FPKM values from the two sequencing lanes for each sample were averaged. Hierarchical clustering was performed with Morpheus (software.broadinstute.ore/morpheus) using the one minus Pearson correlation with average linkage. Gene ontology (GO) analysis was performed using the PANTHER (76) online tool (pantherdb.org).

Matrigel Cord Formation Assay and Quantification

HEK293 fibroblasts and human umbilical vein endothelial cells (HUVECs) were maintained on tissue culture polystyrene flasks in DMEM+10% FBS. Immortalized human BMECs (hBMECs (77), a gift of Kwang Sik Kim and Monique Stins, Johns Hopkins University, Baltimore, Md.) were maintained in RPMI1640+10% FBS+10% NuSerum+1×MEM non-essential amino acids on flasks that had been coated with a solution of 1% rat tail collagen in 70% ethanol that was allowed to evaporate. 8-well glass chamber slides were coated with 200 µL/well concentrated growth factor reduced Matrigel and incubated at least one hour at 37° C. to set the Matrigel. HUVECs or hBMECs were plated at $2.2\times10^4$ cells/8-well chamber slide in 500 µL EGM-2 medium (Lonza) alone, with $6.6\times10^4$ HEK293 fibroblasts, primary brain pericytes, or hPSC-derived mural cells at D22 of the differentiation. Cells were incubated 24 hours at 37° C. to allow cord formation and bright field images taken on live cells at 24 hours following plating. Cords were subsequently fixed and stained according the immunocytochemistry methods listed above. Matrigel-associated cords were mounted onto glass slips and imaged using Olympus epifluorescence and Nikon A1R-Si+ confocal microscopes. Cord length and number of cords per field were quantified by hand using the ImageJ ROI Manager Tool and averaged over at least 3 independent fields per condition per differentiation.

BMEC Differentiation

IMR90C4 iPSCs were maintained in mTesR1 medium on Matrigel-coated plates and passaged as previously described. Three days prior to initiating a differentiation, cells were seeded at $9\times10^4$-$10^5$ cells/cm² onto Matrigel coated plates in mTeSR1+10 µM Y27632. Medium was replaced daily until cells reached >$2.6\times10^5$ cells/cm². Cell medium was replaced with Unconditioned Medium (UM), containing 392.5 mL DMEM/F12, 100 mL KOSR (Gibco), 5 mL 100×MEM non-essential amino acids (Gibco), 2.5 mL 100× Glutamax (Gibco), and 3.5 µL β-mercaptoethanol. Cells were replaced daily with UM for six days, and subsequently switched to EC medium, containing hESFM+ 1% platelet-poor plasma derived serum (PDS), and 20 ng/mL FGF2. Cells were incubated two days with EC medium without replacing medium. Cells were sub-cultured at D8 onto 4:1:5 collagen/fibronectin/water-coated Transwells or 5× diluted 4:1:5 collagen/fibronectin/water-coated plates as detailed by Stebbins et al. (75). Cell culture medium was replaced with EC without FGF2 24 hours after subculturing hPSC-derived BMECs onto filters.

BMEC/Pericyte Co-Culture

Primary brain pericytes, hPSC-derived pericyte-like cells, and 3T3s were separately seeded onto poly-L-lysine coated 12-well plates (primary brain pericytes) or uncoated plates (hPSC-derived early mural cells and 3T3s) when early mural cells reached first reached 80-100% confluence, typically 3-4 days after initiating serum treatment on hPSC-derived NCSC (D19-D20). Cells were plated on the same day at equivalent seeding densities of $5\times10^4$ cells/12-well in either DMEM+10% FBS (primary brain pericytes and 3T3s) or E6+10% FBS (hPSC-derived pericyte-like cells). Cells were dissociated with either 0.25% Trypsin/EDTA (primary brain pericytes and 3T3s) or Accutase (hPSC-derived pericyte-like cells). hPSC-derived brain pericyte-like cell medium was replaced daily with E6+10% FBS until D22 of the differentiation. Pericytes and 3T3s were fed with DMEM+ 10% FBS every two days until D22. At D22, cells were replaced with 1.5 mL EC medium above 12-well polystyrene transwell filters with a 0.4 µm pore size.

IMR90C4 iPSC-derived BMECs at D8 of the BMEC differentiation were sub-cultured onto Transwell filters at $1.1\times10^6$ cells/12-well filter as previously described (75). The high seeding density is intended to ensure a confluent monolayer suitable for TEER and permeability measurements. Cells were incubated two days in co-culture, with cell culture medium replaced at 24 hours after initiating co-culture with EC medium without FGF2. Transendothelial electrical resistance (TEER) was measured every 24 hours after initiating co-culture. 48 hours following co-culture, BMEC Transwell filters were transferred to a fresh 12-well plate for sodium fluorescein assays. Cell medium was replaced with 1.5 mL of EC medium without FGF2 in the basolateral chamber and 0.5 mL of the same medium with 10 µM sodium fluorescein in the apical chamber. Cells were incubated one hour on a rotating platform and basolateral chamber medium collected every 15 minutes during the hour incubation period. After 1 hour, cell culture medium for the apical chamber was collected to calculate sodium fluorescein permeability across BMEC monolayers following 48 hours of co-culture treatment. Fluorescence intensity was measured using a Tecan plate reader set to a 485 nm excitation and 530 nm emission settings. Permeability calculations were determined according to Stebbins et al. (75).

Transcytosis and Accumulation Assays

Following 48 hours of co-culture, BMEC-seeded transwells were transferred to an empty plate. We utilized a 10 kDa dextran tagged with Alexa-488 to quantify the level of intracellular accumulation and transcytosis. 10 µM dextran was suspended in 0.5 mL of EC medium without FGF2 onto the apical side of the transwell. To determine the level of transcytosis, following two hours of incubation in a 37° C. incubator (20% $O_2$, 5% $CO_2$) on a rotating platform, we collected 150 µL from the 1.5 mL of EC medium on the basolateral side of the transwell. Fluorescence intensity was measured using a Tecan plate reader set to a 495 nm excitation and 519 nm emission settings. To determine the level of accumulation (endocytosis) in the BMECs, we rinsed the transwells with cold PBS (2×) and lysed the cells with radioimmunoprecipitation assay (RIPA) buffer. Lysates were collected and analyzed on the plate reader. Fluorescence values were normalized to protein content/Transwell measured using the bicinchoninic acid (BCA) assay.

Tight Junction Image Analysis

BMECs were plated on 24-well plates in EC medium or EC medium conditioned by primary brain pericytes or hPSC-derived pericyte-like cells. After 48 h, BMECs were fixed and stained for occludin as described above. Images were acquired from 5 wells per experimental condition. To quantify tight junction continuity, images were blinded and the area fraction index determined using FIJI as previously described (78). Additionally, images were blinded and the number of frayed junctions (FIG. 4D) manually counted.

Isogenic Model of the Neurovascular Unit

BMECs were differentiated from iPSCs as previously described. Singularized BMECs were seeded onto collagen IV/fibronectin coated transwells at day 8 of the differentiation. hPSC-derived pericytes were seeded onto the bottom of the co-culture plate (~50,000 cells/cm²) in EC medium. We additionally investigated the cumulative effects of pericytes, neurons, and astrocytes. Neurons and astrocytes were differentiated from iPSCs as previously published (34). Initially, BMECs were placed in co-culture with pericytes for 24 hours in EC medium and then BMEC-Transwells were transferred to a co-culture plate with a mixture of neurons and astrocytes (1:3 ratio) for the duration of the experiment in EC medium without FGF2. We benchmarked our stem cell-derived BBB model (BMECs, pericyte-like cells (24 h), and neurons and astrocytes (24 h)) to a BBB co-culture model absent of pericyte-like cells (neurons and astrocytes only). TEER and sodium fluorescein permeability assays were conducted on BMEC-Transwells.

Statistics

All experiments were conducted using at least three technical replicates (e.g. three 6-wells or Transwells) from the same differentiation. All experiments were replicated (independent differentiations) at least three times except where otherwise indicated. Data are presented as mean±SD of technical replicates from a representative differentiation or as mean±SEM of pooled data from several independent differentiations. Statistical significance was evaluated using one-way analysis of variance (ANOVA) followed by post-hoc tests controlling for multiple comparisons: Dunnett's test for comparison of experimental groups to control, and Tukey's test for comparison between all experimental groups. $P<0.05$ was considered statistically significant.

Western Blotting

BMECs were cultured on Transwells alone or co-cultured with hPSC-derived pericyte-like cells, primary brain pericytes, or 3T3s as previously described. After 48 h of co-culture, BMECs were washed once with PBS and lysed with RIPA buffer+Halt protease inhibitor cocktail. The BCA assay was used to determine protein concentration. Proteins were resolved on 4-12% Tris-glycine gels and transferred to nitrocellulose membranes, which were blocked in Tris-buffered saline+0.1% Tween-20 (TBST)+5% nonfat dry milk for 1 h, and incubated with primary antibodies (Table 2) overnight at 4° C. Membranes were washed with TBST (5×) and incubated with donkey anti-mouse or donkey anti-rabbit IRDye 800CW secondary antibodies (LI-COR) for 1 h. Membranes were washed with TBST (5×) and imaged using a LI-COR Odyssey.

Visualization of Dextran Accumulation iPSC-derived BMECs were seeded onto glass bottom plates at a density of $10^5$ cells/cm$^2$ and cultured for 48 h in EC medium or EC medium conditioned by 3T3s, primary pericytes, or IMR90C4-derived pericyte-like cells. Medium was subsequently replaced with EC medium+10 µM Alexa 488-tagged 10 kDa dextran. Following 2 h of dextran incubation, cells were fixed in 4% PFA for fifteen minutes, followed by three washes in PBS. Cells were blocked in 10% goat serum in PBS for 30 minutes at room temperature. Cells were incubated with Anti-Alexa 488 antibody (1:100 in PBS; Life Technologies 11094) overnight at 4° C. on a rocking platform. Following three washes in PBS, cells were incubated with Alexa 647 secondary antibody (1:200 in PBS) for one hour at room temperature on a rocking platform. Nuclei were labeled with Hoechst and cells were rinsed three times in PBS. Cells were visualized on a Nikon A1R-Si+ confocal microscope. The lack of permeabilization allows internalized dextran to visualize only with Alexa 488, while extracellular (surface) dextran is also labeled with Alexa 647.

Primary Rat BMEC/Pericyte Co-Culture

All animal studies were conducted using protocols approved by the University of Wisconsin-Madison Animal Care and Use Committee following NIH guidelines for care and use of laboratory animals. Adult male Sprague-Dawley rat (Harlan Inc., Indianapolis, Ind.) brain capillaries were isolated, minced and digested in collagenase type-2 (0.7 mg/mL) and DNase I (39 U/mL). Purified microvessels were isolated following centrifugation in 20% bovine serum albumin and further digested in collagenase/dispase (1 mg/mL) and DNase I. To purify the population a 33% Percoll gradient was utilized. Capillaries were collected and plated onto collagen IV/fibronectin-coated Transwells. Capillaries were cultured in DMEM supplemented with 1 ng/mL FGF2, 1 µg/mL heparin, 20% PDS, 2 mM L-glutamine, and 1% antibiotic-antimitotic solution. Pure populations were obtained by treating the cells with puromycin (4 µg/mL) for 2 days following seeding. Four days following isolation, rat BMEC-seeded Transwells were transferred onto plates containing IMR90C4-derived pericyte-like cells, primary brain pericytes, or 3T3s (described previously) and co-cultured in EC medium containing 1% PDS.

REFERENCES

1. A. R. Jones, E. V. Shusta, Blood-brain barrier transport of therapeutics via receptor-mediation. *Pharm. Res.* 24, 1759-1771 (2007).
2. J. M. Lajoie, E. V. Shusta, Targeting receptor-mediated transport for delivery of biologics across the blood-brain barrier. *Annu. Rev. Pharmacol. Toxicol.* 55, 613-31 (2015).
3. Y. J. Yu, R. J. Watts, Developing therapeutic antibodies for neurodegenerative disease. *Neurotherapeutics.* 10, 459-72 (2013).
4. B. V Zlokovic, Neurovascular pathways to neurodegeneration in Alzheimer's disease and other disorders. *Nat. Rev. Neurosci.* 12, 723-38 (2011).
5. R. D. Bell et al., Pericytes control key neurovascular functions and neuronal phenotype in the adult brain and during brain aging. *Neuron.* 68, 409-427 (2010).
6. A. P. Sagare, R. D. Bell, B. V Zlokovic, Neurovascular Dysfunction and Faulty Amyloid β-Peptide Clearance in Alzheimer Disease. *Cold Spring Harb. Perspect. Med.* 2, a011452 (2012).
7. A. P. Sagare et al., Pericyte loss influences Alzheimer-like neurodegeneration in mice. *Nat. Commun.* 4, 1-14 (2013).
8. Z. Zhao et al., Central role for PICALM in amyloid-β blood-brain barrier transcytosis and clearance. *Nat. Neurosci.* 18, 978-987 (2015).
9. E. a Winkler et al., GLUT1 reductions exacerbate Alzheimer's disease vasculo-neuronal dysfunction and degeneration. *Nat. Neurosci.* 18, 521-530 (2015).
10. M. R. Halliday et al., Accelerated pericyte degeneration and blood-brain barrier breakdown in apolipoprotein E4 carriers with Alzheimer's disease. *J. Cereb. Blood Flow Metab.* 36, 1-9 (2015).
11. B. Obermeier, R. Daneman, R. M. Ransohoff, Development, maintenance and disruption of the blood-brain barrier. *Nat. Med.* (2013), doi:10.1038/nm. 3407.
12. W. A. Banks, From blood-brain barrier to blood-brain interface: new opportunities for CNS drug delivery. *Nat. Rev. Drug Discov.* 15, 275-292 (2016).
13. R. Daneman, L. Zhou, A. A. Kebede, B. A. Barres, Pericytes are required for blood-brain barrier integrity during embryogenesis. *Nature.* 468, 562-566 (2010).
14. A. Armulik et al., Pericytes regulate the blood-brain barrier. *Nature.* 468, 557-561 (2010).
15. N. J. Abbott, L. Rönnbäck, E. Hansson, Astrocyte-endothelial interactions at the blood-brain barrier. *Nat. Rev. Neurosci.* (2006), doi:10.1038/nrn1824.
16. G. Savettieri et al., Neurons and ECM regulate occludin localization in brain endothelial cells. *Neuroreport.* 11, 1081-1084 (2000).
17. G. Schiera et al., Synergistic effects of neurons and astrocytes on the differentiation of brain capillary endothelial cells in culture. *J. Cell. Mol. Med.* 7, 165-70 (2003).
18. G. Schiera et al., Permeability properties of a three-cell type in vitro model of blood-brain barrier. *J. Cell. Mol. Med.* 9, 373-9 (2005).

19. C. M. Peppiatt, C. Howarth, P. Mobbs, D. Attwell, Bidirectional control of CNS capillary diameter by pericytes. *Nature.* 443, 700-704 (2006).
20. L. Diaz-Flores et al., Pericytes. Morphofunction, interactions and pathology in a quiescent and activated mesenchymal cell niche. *Histol. Histopathol.* 24, 909-969 (2009).
21. N. B. Hamilton, D. Attwell, C. N. Hall, Pericyte-mediated regulation of capillary diameter: a component of neurovascular coupling in health and disease. *Front. Neuroenergetics.* 2, 1-14 (2010).
22. P. Saharinen et al., Angiopoietins assemble distinct Tie2 signalling complexes in endothelial cell-cell and cell-matrix contacts. *Nat. Cell Biol.* 10, 527-537 (2008).
23. A. N. Stratman, K. M. Malotte, R. D. Mahan, M. J. Davis, G. E. Davis, Pericyte recruitment during vasculogenic tube assembly stimulates endothelial basement membrane matrix formation. *Blood.* 114, 5091-5101 (2009).
24. R. J. Van Geest, I. Klaassen, I. M. C. Vogels, C. J. F. Van Noorden, R. O. Schlingemann, Differential TGF-β Signaling in Retinal Vascular Cells: A Role in Diabetic Retinopathy? *Investig. Opthalmology Vis. Sci.* 51, 1857 (2010).
25. A. Ben-Zvi et al., Mfsd2a is critical for the formation and function of the blood-brain barrier. *Nature.* 509, 507-11 (2014).
26. R. J. Bodnar, M. E. Rodgers, W. C. W. Chen, A. Wells, Pericyte Regulation of Vascular Remodeling Through the CXC Receptor 3. *Arterioscler. Thromb. Vasc. Biol.* 33, 2818-2829 (2013).
27. R. Cecchelli et al., A stable and reproducible human blood-brain barrier model derived from hematopoietic stem cells. *PLoS One.* 9 (2014), doi:10.1371/journal.pone.0099733.
28. S. Nakagawa et al., Pericytes from Brain Microvessels Strengthen the Barrier Integrity in Primary Cultures of Rat Brain Endothelial Cells. *Cell. Mol. Neurobiol.* 27, 687-694 (2007).
29. S. Nakagawa et al., A new blood-brain barrier model using primary rat brain endothelial cells, pericytes and astrocytes. *Neurochem. Int.* 54, 253-263 (2009).
30. E. S. Lippmann, A. Al-Ahmad, S. M. Azarin, S. P. Palecek, E. V Shusta, A retinoic acid-enhanced, multicellular human blood-brain barrier model derived from stem cell sources. *Sci. Rep.* 4, 4160 (2014).
31. P. A. Clark et al., Analysis of cancer-targeting alkylphosphocholine analogue permeability characteristics using a human induced pluripotent stem cell blood-brain barrier model. *Mol. Pharm.* 13, 3341-3349 (2016).
32. G. D. Vatine et al., Modeling Psychomotor Retardation using iPSCs from MCT8-Deficient Patients Indicates a Prominent Role for the Blood-Brain Barrier. *Cell Stem Cell,* 1-13 (2016).
33. R. G. Lim et al., Huntington's Disease iPSC-Derived Brain Microvascular Endothelial Cells Reveal WNT-Mediated Angiogenic and Blood-Brain Barrier Deficits. *Cell Rep.* 19, 1365-1377 (2017).
34. S. G. Canfield et al., An isogenic blood-brain barrier model comprising brain endothelial cells, astrocytes, and neurons derived from human induced pluripotent stem cells. *J. Neurochem.* 140, 874-888 (2017).
35. A. Appelt-Menzel et al., Establishment of a Human Blood-Brain Barrier Co-culture Model Mimicking the Neurovascular Unit Using Induced Pluri- and Multipotent Stem Cells. *Stem Cell Reports.* 8, 894-906 (2017).
36. M. Ribecco-Lutkiewicz et al., A novel human induced pluripotent stem cell blood-brain barrier model: Applicability to study antibody-triggered receptor-mediated transcytosis. *Sci. Rep.* 8, 1-17 (2018).
37. C. Griffin, R. Bajpai, Neural crest-derived human cranial pericytes model primary forebrain pericytes and predict disease-specific cranial vasculature defects. *SSRN* (2018).
38. R. J. Boado, W. M. Pardridge, Differential expression of alpha-actin mRNA and immunoreactive protein in brain microvascular pericytes and smooth muscle cells. *J. Neurosci. Res.* 39, 430-5 (1994).
39. P. Dore-Duffy, K. Cleary, in *Methods in molecular biology* (Clifton, N.J.) (2011), vol. 686, pp. 49-68.
40. M. Vanlandewijck et al., A molecular atlas of cell types and zonation in the brain vasculature. *Nature.* 554, 475-480 (2018).
41. C. Cheung, A. S. Bernardo, M. W. B. Trotter, R. A. Pedersen, S. Sinha, Generation of human vascular smooth muscle subtypes provides insight into embryological origin-dependent disease susceptibility. *Nat. Biotechnol.* 30, 165-173 (2012).
42. C. Cheung, Y. Y. T. Goh, J. Zhang, C. Wu, E. Guccione, Modeling cerebrovascular pathophysiology in amyloid-β metabolism using neural-crest-derived smooth muscle cells. *Cell Rep.* 9, 391-401 (2014).
43. H. C. Etchevers, C. Vincent, N. M. Le Douarin, G. F. Couly, The cephalic neural crest provides pericytes and smooth muscle cells to all blood vessels of the face and forebrain. *Development.* 128, 1059-1068 (2001).
44. J. Korn, B. Christ, R. Kurz, H. Kurz, Neuroectodermal origin of brain pericytes and vascular smooth muscle cells. *J. Comp. Neurol.* 442, 78-88 (2002).
45. G. Lee et al., Isolation and directed differentiation of neural crest stem cells derived from human embryonic stem cells. *Nat. Biotechnol.* 25 (2007), doi:10.1038/nbt1365.
46. L. Menendez et al., Wnt signaling and a Smad pathway blockade direct the differentiation of human pluripotent stem cells to multipotent neural crest cells. *Proc. Natl. Acad. Sci.* 109, 9220-9220 (2012).
47. A. Wang et al., Derivation of Smooth Muscle Cells with Neural Crest Origin from Human Induced Pluripotent Stem Cells. *Cells Tissues Organs.* 195, 5-14 (2012).
48. L. Menendez et al., Directed differentiation of human pluripotent cells to neural crest stem cells. *Nat. Protoc.* 8, 203-212 (2013).
49. L. He et al., Analysis of the brain mural cell transcriptome. *Sci. Rep.* 6, 35108 (2016).
50. A. Armulik, A. Abramsson, C. Betsholtz, Endothelial/pericyte interactions. *Circ. Res.* 97, 512-523 (2005).
51. A. Armulik, G. Genové, C. Betsholtz, Pericytes: Developmental, Physiological, and Pathological Perspectives, Problems, and Promises. *Dev. Cell.* 21, 193-215 (2011).
52. V. V. Orlova et al., Functionality of endothelial cells and pericytes from human pluripotent stem cells demonstrated in cultured vascular plexus and zebrafish xenografts. *Arterioscler. Thromb. Vasc. Biol.* 34, 177-186 (2014).
53. N. Guimarães-Camboa et al., Pericytes of Multiple Organs Do Not Behave as Mesenchymal Stem Cells In Vivo. *Cell Stem Cell.* 20, 345-359.e5 (2017).
54. A. Reyahi et al., Foxf2 Is Required for Brain Pericyte Differentiation and Development and Maintenance of the Blood-Brain Barrier. *Dev. Cell.* 34, 19-32 (2015).
55. R. Daneman et al., The mouse blood-brain barrier transcriptome: A new resource for understanding the development and function of brain endothelial cells. *PLoS One.* 5, 1-16 (2010).

56. E. S. Lippmann et al., Derivation of Blood-Brain Barrier Endothelial Cells from Human Pluripotent Stem Cells. *Nat. Biotechnol.* 30, 783-791 (2012).
57. J. L. Mantle, L. Min, K. H. Lee, Minimum Transendothelial Electrical Resistance Thresholds for the Study of Small and Large Molecule Drug Transport in a Human in Vitro Blood-Brain Barrier Model. *Mol. Pharm.* 13, 4191-4198 (2016).
58. X. Huang, J. P. Saint-Jeannet, Induction of the neural crest and the opportunities of life on the edge. *Dev. Biol.* 275, 1-11 (2004).
59. G. Lee, S. M. Chambers, M. J. Tomishima, L. Studer, Derivation of neural crest cells from human pluripotent stem cells. *Nat. Protoc.* 5, 688-701 (2010).
60. C. Cheung, A. S. Bernardo, R. A. Pedersen, S. Sinha, Directed differentiation of embryonic origin-specific vascular smooth muscle subtypes from human pluripotent stem cells. *Nat. Protoc.* 9, 929-38 (2014).
61. R. A. Hill et al., Regional Blood Flow in the Normal and Ischemic Brain Is Controlled by Arteriolar Smooth Muscle Cell Contractility and Not by Capillary Pericytes. *Neuron.* 87, 95-110 (2015).
62. H. S. Wei et al., Erythrocytes Are Oxygen-Sensing Regulators of the Cerebral Microcirculation. *Neuron.* 91, 851-862 (2016).
63. L. Alarcon-Martinez et al., Capillary pericytes express α-smooth muscle actin, which requires prevention of filamentous-actin depolymerization for detection. *Elife.* 7, 1-17 (2018).
64. A. Kumar et al., Specification and Diversification of Pericytes and Smooth Muscle Cells from Mesenchymoangioblasts. *Cell Rep.* 19, 1902-1916 (2017).
65. J. C. L. Zhang et al., Analysis of SM22☐-De cient Mice Reveals Unanticipated Insights into Smooth Muscle Cell Differentiation and Function. *Society.* 21, 1336-1344 (2001).
66. A. R. Calabria, C. Weidenfeller, A. R. Jones, H. E. De Vries, E. V Shusta, Puromycin-purified rat brain microvascular endothelial cell cultures exhibit improved barrier properties in response to glucocorticoid induction, 922-933 (2006).
67. S. Dohgu et al., Brain pericytes contribute to the induction and up-regulation of blood-brain barrier functions through transforming growth factor-beta production. *Brain Res.* 1038, 208-215 (2005).
68. R. Muramatsu et al., Prostacyclin prevents pericyte loss and demyelination induced by lysophosphatidylcholine in the central nervous system. *J. Biol. Chem.* 290, 11515-11525 (2015).
69. R. Garbelli et al., PDGFRβ+ cells in human and experimental neuro-vascular dysplasia and seizures. *Neuroscience.* 306, 18-27 (2015).
70. S. Milesi et al., Redistribution of PDGFRβ cells and NG2DsRed pericytes at the cerebrovasculature after status epilepticus. *Neurobiol. Dis.* 71, 151-158 (2014).
71. E. Gonul et al., Early pericyte response to brain hypoxia in cats: An ultrastructural study. *Microvasc. Res.* 64, 116-119 (2002).
72. Y. I. Wang, H. E. *Abaci*, M. L. Shuler, Microfluidic blood-brain barrier model provides in vivo-like barrier properties for drug permeability screening. *Biotechnol. Bioeng.* 114, 184-194 (2017).
73. T. Park et al., Hypoxia-enhanced Blood-Brain Barrier Chip recapitulates human barrier function, drug penetration, and antibody shuttling properties. *bioRxiv* (2018), doi:10.1101/482463.
74. G. Chen et al., Chemically defined conditions for human iPS cell derivation and culture. *Nat. Methods.* 8, 424-429 (2011).
75. M. J. Stebbins et al., Differentiation and characterization of human pluripotent stem cell-derived brain microvascular endothelial cells. *Methods.* 101, 93-102 (2016).
76. H. Mi et al., PANTHER version 11: Expanded annotation data from Gene Ontology and Reactome pathways, and data analysis tool enhancements. *Nucleic Acids Res.* 45, D183-D189 (2017).
77. M. F. Stins, J. Badger, K. Sik, Bacterial invasion and transcytosis in transfected human brain microvascular endothelial cells, 19-28 (2001).
78. M. J. Stebbins et al., Activation of RARα, RARγ, or RXRα Increases Barrier Tightness in Human Induced Pluripotent Stem Cell-Derived Brain Endothelial Cells. *Biotechnol. J.* 1700093, 1700093 (2017).

We claim:

1. A method of creating a population of brain pericyte-like cells, wherein the cells express pericyte markers but do not express α-smooth muscle actin (α-SMA) and wherein the cells are generated from human pluripotent stem cells (hPSC), comprising the steps of
   a. culturing hPSC in culture medium supplemented with CHIR99021, SB431542, fibroblast growth factor 2, and dorsomorphin for about 15 days to produce p75-nerve growth factor receptor (NGFR)+ human natural killer-1 (HNK-1)+ neural crest stem cells (NCSCs),
   b. sorting p75-NGFR⁺ cells and re-plating the p75-NGFR⁺ cells to produce an enriched population of p75-NGFR⁺NCSCs,
   c. culturing the cells of step (b) in medium with an addition of serum for about 11 days, and
   d. isolating cells that express pericyte markers calponin 1 (CNN1), neuron-glial antigen 2 (NG2), and platelet-derived growth factor receptor beta (PDGFRB) but do not express α-SMA to produce population of brain pericyte-like cells.

2. The method of claim 1, wherein the NCSCs of step (b) are p75-NGFR⁺HNK-1⁺AP-2⁺ NCCs.

3. The method of claim 1, wherein the population of cells express one or more transcripts of pericyte markers selected from the group consisting of chondroitin sulfate proteoglycan 4 (CSPG4), PDGFRB, CNN1, transgelin (TAGLN), alanyl aminopeptidase (ANPEP), T-box transcription factor 18 (TBX18), ATP binding cassette subfamily C member 9 (ABCC9) and potassium inwardly rectifying channel subfamily J member 8 (KCNJ8).

4. The method of claims 1, wherein the method produces the brain pericyte-like cell population that is at least 90% NG2⁺PDGFRB⁺.

* * * * *

UNITED STATES PATENT AND TRADEMARK OFFICE
CERTIFICATE OF CORRECTION

PATENT NO. : 11,643,636 B2  
APPLICATION NO. : 16/507586  
DATED : May 9, 2023  
INVENTOR(S) : Eric V. Shusta et al.

Page 1 of 1

It is certified that error appears in the above-identified patent and that said Letters Patent is hereby corrected as shown below:

In the Specification

Column 13, Line 13, "NGFRIINK$^+$AP-2$^+$" should be --NGFR$^+$HNK$^+$AP-2$^+$--.

Signed and Sealed this
Twenty-fourth Day of October, 2023

Katherine Kelly Vidal  
*Director of the United States Patent and Trademark Office*